US012799219B2

(12) United States Patent
Zhou et al.

(10) Patent No.: US 12,799,219 B2
(45) Date of Patent: Nov. 17, 2026

(54) ENGINEERED IMMUNE CELL EXPRESSING NK INHIBITORY MOLECULE AND USE THEREOF

(71) Applicant: NANJING BIOHENG BIOTECH CO., LTD, Nanjing (CN)

(72) Inventors: Yali Zhou, Nanjing (CN); Gong Chen, Nanjing (CN); Xiaoyan Jiang, Nanjing (CN); Jiangtao Ren, Nanjing (CN); Xiaohong He, Nanjing (CN); Yanbin Wang, Nanjing (CN); Lu Han, Nanjing (CN)

(73) Assignee: IMVIVA BIOSCIENCES LIMITED, Grand Cayman (KY)

( * ) Notice: Subject to any disclaimer, the term of this patent is extended or adjusted under 35 U.S.C. 154(b) by 1064 days.

(21) Appl. No.: 17/910,007

(22) PCT Filed: Jun. 10, 2021

(86) PCT No.: PCT/CN2021/099314

§ 371 (c)(1),
(2) Date: Sep. 8, 2022

(87) PCT Pub. No.: WO2021/249462

PCT Pub. Date: Dec. 16, 2021

(65) Prior Publication Data

US 2023/0242661 A1 Aug. 3, 2023

(30) Foreign Application Priority Data

Jun. 11, 2020 (CN) ......................... 202010527572.0
Nov. 3, 2020 (CN) ......................... 202011209420.2

(51) Int. Cl.

| | |
|---|---|
| ***C07K 16/28*** | (2006.01) |
| ***A61K 40/11*** | (2025.01) |
| ***A61K 40/42*** | (2025.01) |
| ***C07K 14/705*** | (2006.01) |
| ***C12N 5/0783*** | (2010.01) |

(52) U.S. Cl.

CPC .......... *C07K 16/2896* (2013.01); *A61K 40/11* (2025.01); *A61K 40/421* (2025.01); *A61K 40/4224* (2025.01); *C07K 14/7051* (2013.01); *C07K 14/70539* (2013.01); *C12N 5/0636* (2013.01); *C12N 5/0646* (2013.01); *C07K 2317/565* (2013.01); *C07K 2319/02* (2013.01); *C07K 2319/03* (2013.01)

(58) Field of Classification Search

CPC ............ C07K 16/2896; C07K 14/7051; C07K 14/70539; C07K 2317/565; C07K 2319/02; C07K 2319/03; A61K 40/11; A61K 40/421; A61K 40/4224; A61K 38/00; A61K 40/50; A61K 35/15; A61K 40/30; C12N 5/0636; C12N 5/0646

See application file for complete search history.

(56) References Cited

U.S. PATENT DOCUMENTS

| | | | | |
|---|---|---|---|---|
| 2009/0208416 A1* | 8/2009 | Moretta | ........... G01N 33/56966 435/375 |
| 2018/0360884 A1 | 12/2018 | Adusumilli | |
| 2023/0242661 A1 | 8/2023 | Zhou et al. | |

FOREIGN PATENT DOCUMENTS

| | | | | |
|---|---|---|---|---|
| CN | 107573419 A | 1/2018 | |
| CN | 109694854 A | 4/2019 | |
| CN | 110352068 A | 10/2019 | |
| CN | 110616186 A | 12/2019 | |
| CN | 110863013 A | 3/2020 | |
| EP | 4112721 A1 | 1/2023 | |
| JP | 2011510047 A | 3/2011 | |
| JP | 2017502690 A | 1/2017 | |
| JP | 2018507685 A | 3/2018 | |
| JP | 2020510101 A | 4/2020 | |
| WO | WO-2008084106 A1 * | 7/2008 | ............. A61P 35/00 |
| WO | 2015142675 A2 | 9/2015 | |
| WO | WO 2017/040301 * | 3/2017 | ............ C07K 16/28 |
| WO | 2019112899 A2 | 6/2019 | |
| WO | 2019195541 A1 | 10/2019 | |
| WO | 2020097188 A1 | 5/2020 | |
| WO | 2021226543 A2 | 11/2021 | |
| WO | 2021249462 A1 | 12/2021 | |
| WO | 2022095802 A1 | 5/2022 | |

(Continued)

OTHER PUBLICATIONS

Lee et al. (PNAS, 95: 5199-5204, 1998).*
Reighard et al., "Therapeutic Targeting of Follicular T Cells withChimeric Antigen Receptor-Expressing NaturalKiller Cells", Cell Reports Medicine, 1, 100003, Apr. 21, 2020, 26 pages.
Office Action with regard to the counterpart JP Patent Application No. 2022-549899 issued Aug. 7, 2023.
European Search Report with regard to the counterpart EP Patent Application No. 21821147.2 dated Mar. 11, 2023.
International Search Report and Written Opinion (and English Translation of ISR) with regard to PCT/CN2021/099314 mailed Sep. 8, 2021.
English Abstract for CN107573419 retrieved on Espacenet on Aug. 4, 2022.

(Continued)

*Primary Examiner* — Nelson B Moseley, II
(74) *Attorney, Agent, or Firm* — BCF LLP

(57) ABSTRACT

Provided is an NK inhibitory molecule, which includes one or more NK inhibitory ligands, a transmembrane domain and a co-stimulatory domain, wherein the NK inhibitory ligand specifically binds to NK inhibitory receptors to inhibit the killing of NK cells against the engineered immune cells expressing the NK inhibitory molecule. Also provided is an engineered immune cell expressing the NK inhibitory molecule of the present invention, wherein the expression of at least one MHC-related gene is suppressed or silenced. Further provided is the use of the engineered immune cell in the treatment of cancers, infections or autoimmune diseases. Compared to the traditional engineered immune cells, the engineered immune cell can significantly inhibit the killing effect of NK cells in a subject, thereby reducing the risk of HvGD.

16 Claims, 8 Drawing Sheets

Specification includes a Sequence Listing.

(56) References Cited

FOREIGN PATENT DOCUMENTS

WO 2022179620 A1 9/2022

OTHER PUBLICATIONS

English Abstract for CN110352068 retrieved on Espacenet on Aug. 4, 2022.
English Abstract for CN110863013 retrieved on Espacenet on Aug. 4, 2022.
English Abstract for CN109694854 retrieved on Espacenet on Aug. 4, 2022.
Office Action issued on May 30, 2025 in respect of the counterpart JP patent application No. 2024109827, including its English translation.
Office Action issued on May 28, 2024 in respect of the counterpart AU patent application No. 2021286676.
Office Action issued on Sep. 3, 2023 in respect of the counterpart CA patent application No. 3171344.

* cited by examiner

SEQUENCE LISTING

```
<160> NUMBER OF SEQ ID NOS: 196

<210> SEQ ID NO 1
<211> LENGTH: 119
<212> TYPE: PRT
<213> ORGANISM: Artificial sequence
<220> FEATURE:
<223> OTHER INFORMATION: mNKG2A scFv-VH

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95

Thr Arg His Gly Asp Tyr Pro Arg Phe Phe Asp Val Trp Gly Ala Gly
            100                 105                 110

Thr Thr Val Thr Val Ser Ser
        115


<210> SEQ ID NO 2
<211> LENGTH: 357
<212> TYPE: DNA
<213> ORGANISM: Artificial sequence
<220> FEATURE:
<223> OTHER INFORMATION: mNKG2A scFv-VH

<400> SEQUENCE: 2

gaagttcaac tggtagagtc agggggcgga ttggtaaagc cgggggggctc tctgaagctg      60

tcatgcgccg catctgggtt taccttcagt tcttacgcta tgagttgggt tcgccagtct     120

cccgaaaaga gattggagtg ggtagcggaa attagttcag gcggaagcta cacgtattac     180

cccgatacag tcacgggacg gtttaccatt tcccgcgata atgccaagaa cacgctgtac     240

ctcgagatca gctctttgcg gagcgaggat actgcgatgt attactgcac ccgacacgga     300

gattatccga gatttttga tgtatgggga gcgggaacga cagttaccgt ctccagc         357


<210> SEQ ID NO 3
<211> LENGTH: 107
<212> TYPE: PRT
<213> ORGANISM: Artificial sequence
<220> FEATURE:
<223> OTHER INFORMATION: mNKG2A scFv-VL

<400> SEQUENCE: 3

Gln Ile Val Leu Thr Gln Ser Pro Ala Leu Met Ser Ala Ser Pro Gly
1               5                   10                  15
```

-continued

```
Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys Arg
            100                 105
```

<210> SEQ ID NO 4
<211> LENGTH: 321
<212> TYPE: DNA
<213> ORGANISM: Artificial sequence
<220> FEATURE:
<223> OTHER INFORMATION: mNKG2A scFv-VL

<400> SEQUENCE: 4

```
cagatagtgc tgacacaaag cccagcactt atgtccgcat ccccaggaga aaaagtaacg      60

atgacttgta gcgctagttc tagtgtgagt tatatatact ggtatcagca gaaaccgaga     120

agtagtccga agccctggat ctatctcaca agcaatttgg ccagtggagt gcccgcgcgg     180

ttcagcggaa gtggcagcgg cacttcttac agcctcacta taagcagtat ggaagccgag     240

gacgcggcaa cgtattattg ccaacagtgg tccggcaatc cttatacttt tggtggcggt     300

acgaaactgg agatcaaacg c                                               321
```

<210> SEQ ID NO 5
<211> LENGTH: 119
<212> TYPE: PRT
<213> ORGANISM: Artificial sequence
<220> FEATURE:
<223> OTHER INFORMATION: hNKG2A scFv-VH

<400> SEQUENCE: 5

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Lys Ser Trp Val Arg Gln Ala Pro Gly Lys Gly Leu Glu Trp Val
        35                  40                  45

Ser Glu Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Pro Arg Phe Phe Asp Val Trp Gly Gln Gly
            100                 105                 110

Thr Thr Val Thr Val Ser Ser
        115
```

<210> SEQ ID NO 6
<211> LENGTH: 357
<212> TYPE: DNA

<213> ORGANISM: Artificial sequence
<220> FEATURE:
<223> OTHER INFORMATION: hNKG2A scFv-VH

<400> SEQUENCE: 6
gaagtccaac ttgttgaaag cggagggggg cttgtaaagc caggtggttc tctccgcttg 60
agttgtgccg cttctggctt taccttctct tcttacgcta aatcttgggt tcgccaggct 120
cccggtaagg gtctggagtg ggtcagcgaa atctcttctg gggctcccta cacctactat 180
gccgattctg tgaaggggcg gttcaccata agccgcgaca acgcaaagaa cagcctctac 240
cttcagatga acagcctgcg cgcagaggac acagcagtct attactgcgc tcgacatggg 300
gattatccta gatttttga cgtctggggc caaggcacta ccgttaccgt aagcagc 357

<210> SEQ ID NO 7
<211> LENGTH: 107
<212> TYPE: PRT
<213> ORGANISM: Artificial sequence
<220> FEATURE:
<223> OTHER INFORMATION: hNKG2A scFv-VL

<400> SEQUENCE: 7

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Trp Ser Gly Asn Pro Tyr
85 90 95

Thr Phe Gly Gln Gly Thr Lys Leu Glu Ile Lys
100 105

<210> SEQ ID NO 8
<211> LENGTH: 321
<212> TYPE: DNA
<213> ORGANISM: Artificial sequence
<220> FEATURE:
<223> OTHER INFORMATION: hNKG2A scFv-VL

<400> SEQUENCE: 8
gaaatagttt tgacacaatc cccagcaacc ctttctctgt caccaggtga gagagctacg 60
ttgtcttgca gtgcgagttc cagcgtctct tcctacatct actggtacca gcagaagccc 120
gggcaggccc ctcgattgct catatacctg acatccaatc tggcatctgg aataccagca 180
cggttctctg gctcaggtag cggtacagac tttaccctga caatctcttc cctggaaccc 240
gaggactttg ccgtgtacta ctgccaacaa tggtctggga atccatatac tttcgggcag 300
gggacaaaac ttgaaatcaa g 321

<210> SEQ ID NO 9
<211> LENGTH: 25
<212> TYPE: PRT
<213> ORGANISM: Artificial sequence
<220> FEATURE:
<223> OTHER INFORMATION: CD8alpha transmembrane domain

<400> SEQUENCE: 9

Ile Tyr Ile Trp Ala Pro Leu Ala Gly Thr Cys Gly Val Leu Leu Leu
1 5 10 15

Ser Leu Val Ile Thr Leu Tyr Cys Lys
20 25

<210> SEQ ID NO 10
<211> LENGTH: 75
<212> TYPE: DNA
<213> ORGANISM: Artificial sequence
<220> FEATURE:
<223> OTHER INFORMATION: CD8alpha transmembrane domain

<400> SEQUENCE: 10
atctacatct gggcgccctt ggccgggact tgtggggtcc ttctcctgtc actggttatc 60
accctttact gcaaa 75

<210> SEQ ID NO 11
<211> LENGTH: 27
<212> TYPE: PRT
<213> ORGANISM: Artificial sequence
<220> FEATURE:
<223> OTHER INFORMATION: CD28transmembrane domain

<400> SEQUENCE: 11

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 12
<211> LENGTH: 81
<212> TYPE: DNA
<213> ORGANISM: Artificial sequence
<220> FEATURE:
<223> OTHER INFORMATION: CD28transmembrane domain

<400> SEQUENCE: 12
ttttgggtcc tcgtcgtagt tggaggggta cttgcctgtt atagcctcct ggttaccgta 60
gcatttatta tattctgggt g 81

<210> SEQ ID NO 13
<211> LENGTH: 41
<212> TYPE: PRT
<213> ORGANISM: Artificial sequence
<220> FEATURE:
<223> OTHER INFORMATION: CD28co-stimulatory domain

<400> SEQUENCE: 13

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 14
<211> LENGTH: 123
<212> TYPE: DNA
<213> ORGANISM: Artificial sequence
<220> FEATURE:
<223> OTHER INFORMATION: CD28co-stimulatory domain

<400> SEQUENCE: 14
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 15
<211> LENGTH: 40
<212> TYPE: PRT
<213> ORGANISM: Artificial sequence
<220> FEATURE:
<223> OTHER INFORMATION: 4-1BB co-stimulatory domain

<400> SEQUENCE: 15

Arg Gly Arg Lys Lys Leu Leu Tyr Ile Phe Lys Gln Pro Phe Met Arg
1 5 10 15

Pro Val Gln Thr Thr Gln Glu Glu Asp Gly Cys Ser Cys Arg Phe Pro
20 25 30

Glu Glu Glu Glu Gly Gly Cys Glu
35 40

<210> SEQ ID NO 16
<211> LENGTH: 120
<212> TYPE: DNA
<213> ORGANISM: Artificial sequence
<220> FEATURE:
<223> OTHER INFORMATION: 4-1BB co-stimulatory domain

<400> SEQUENCE: 16
cggggcagaa agaaactcct gtatatattc aaacaaccat ttatgagacc agtacaaact 60
actcaagagg aagatggctg tagctgccga tttccagaag aagaagaagg aggatgtgaa 120

<210> SEQ ID NO 17
<211> LENGTH: 113
<212> TYPE: PRT
<213> ORGANISM: Artificial sequence
<220> FEATURE:
<223> OTHER INFORMATION: CD3zeta signaling domain

<400> SEQUENCE: 17

Leu Arg Val Lys Phe Ser Arg Ser Ala Asp Ala Pro Ala Tyr Gln Gln
1 5 10 15

Gly Gln Asn Gln Leu Tyr Asn Glu Leu Asn Leu Gly Arg Arg Glu Glu
20 25 30

Tyr Asp Val Leu Asp Lys Arg Arg Gly Arg Asp Pro Glu Met Gly Gly
35 40 45

Lys Pro Arg Arg Lys Asn Pro Gln Glu Gly Leu Tyr Asn Glu Leu Gln
50 55 60

Lys Asp Lys Met Ala Glu Ala Tyr Ser Glu Ile Gly Met Lys Gly Glu
65 70 75 80

Arg Arg Arg Gly Lys Gly His Asp Gly Leu Tyr Gln Gly Leu Ser Thr
85 90 95

Ala Thr Lys Asp Thr Tyr Asp Ala Leu His Met Gln Ala Leu Pro Pro
100 105 110

Arg

<210> SEQ ID NO 18
<211> LENGTH: 339
<212> TYPE: DNA
<213> ORGANISM: Artificial sequence
<220> FEATURE:
<223> OTHER INFORMATION: CD3zeta signaling domain

<400> SEQUENCE: 18
ctgagagtga agttcagcag gagcgcagac gcccccgcgt accagcaggg ccagaaccag 60
ctctataacg agctcaatct aggacgaaga gaggagtacg atgttttgga caagagacgt 120
ggccgggacc ctgagatggg gggaaagccg agaaggaaga accctcagga aggcctgtac 180
aatgaactgc agaaagataa gatggcggag gcctacagtg agattgggat gaaaggcgag 240
cgccggaggg gcaaggggca cgatggcctt taccagggtc tcagtacagc caccaaggac 300
acctacgacg cccttcacat gcaggccctg ccccctcgc 339

<210> SEQ ID NO 19
<211> LENGTH: 114
<212> TYPE: PRT
<213> ORGANISM: Artificial sequence
<220> FEATURE:
<223> OTHER INFORMATION: CD3zeta signaling domain mutant

<400> SEQUENCE: 19

Leu Arg Val Lys Phe Ser Arg Ser Ala Asp Ala Pro Ala Tyr Gln Gln
1 5 10 15

Gly Gln Asn Gln Leu Phe Asn Glu Leu Asn Leu Gly Arg Arg Glu Glu
20 25 30

Phe Asp Val Leu Asp Lys Arg Arg Gly Arg Asp Pro Glu Met Gly Gly
35 40 45

Lys Pro Gln Arg Arg Lys Asn Pro Gln Glu Gly Leu Tyr Asn Glu Leu
50 55 60

Gln Lys Asp Lys Met Ala Glu Ala Tyr Ser Glu Ile Gly Met Lys Gly
65 70 75 80

Glu Arg Arg Arg Gly Lys Gly His Asp Gly Leu Phe Gln Gly Leu Ser
85 90 95

Thr Ala Thr Lys Asp Thr Phe Asp Ala Leu His Met Gln Ala Leu Pro
100 105 110

Pro Arg

<210> SEQ ID NO 20
<211> LENGTH: 342
<212> TYPE: DNA
<213> ORGANISM: Artificial sequence
<220> FEATURE:
<223> OTHER INFORMATION: CD3zeta signaling domain mutant

<400> SEQUENCE: 20
ctgagagtga agttcagcag gagcgcagac gcccccgcgt accagcaggg ccagaaccag 60
ctctttaacg agctcaatct aggacgaaga gaggagttcg atgttttgga caagagacgt 120
ggccgggacc ctgagatggg gggaaagccg cagagaagga agaaccctca ggaaggcctg 180
tacaatgaac tgcagaaaga taagatggcg gaggcctaca gtgagattgg gatgaaaggc 240
gagcgccgga ggggcaaggg gcacgatggc cttttccagg gtctcagtac agccaccaag 300
gacacctttg acgcccttca catgcaggcc ctgccccctc gc 342

<210> SEQ ID NO 21
<211> LENGTH: 20
<212> TYPE: PRT
<213> ORGANISM: Artificial sequence
<220> FEATURE:
<223> OTHER INFORMATION: B2M signal peptide

<400> SEQUENCE: 21

Met Ser Arg Ser Val Ala Leu Ala Val Leu Ala Leu Leu Ser Leu Ser
1 5 10 15

Gly Leu Glu Ala
20

<210> SEQ ID NO 22
<211> LENGTH: 60
<212> TYPE: DNA
<213> ORGANISM: Artificial sequence
<220> FEATURE:
<223> OTHER INFORMATION: B2M signal peptide

<400> SEQUENCE: 22
atgtcccgct ctgttgcttt ggctgtgctg gcccttttgt cccttagcgg actggaggcc 60

<210> SEQ ID NO 23
<211> LENGTH: 21
<212> TYPE: PRT
<213> ORGANISM: Artificial sequence
<220> FEATURE:
<223> OTHER INFORMATION: CD8alpha signal peptide

<400> SEQUENCE: 23

Met Ala Leu Pro Val Thr Ala Leu Leu Leu Pro Leu Ala Leu Leu Leu
1 5 10 15

His Ala Ala Arg Pro
20

<210> SEQ ID NO 24
<211> LENGTH: 63
<212> TYPE: DNA
<213> ORGANISM: Artificial sequence
<220> FEATURE:
<223> OTHER INFORMATION: CD8alpha signal peptide

<400> SEQUENCE: 24
atggccttac cagtgaccgc cttgctcctg ccgctggcct tgctgctcca cgccgccagg 60
ccg 63

<210> SEQ ID NO 25
<211> LENGTH: 45
<212> TYPE: PRT
<213> ORGANISM: Artificial sequence
<220> FEATURE:
<223> OTHER INFORMATION: CD8alpha hinge region

<400> SEQUENCE: 25

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 26
<211> LENGTH: 135
<212> TYPE: DNA
<213> ORGANISM: Artificial sequence
<220> FEATURE:
<223> OTHER INFORMATION: CD8alpha hinge region

<400> SEQUENCE: 26

```
accacgacgc cagcgccgcg accaccaaca ccggcgccca ccatcgcgtc gcagcccctg     60

tccctgcgcc cagaggcgtg ccggccagcg gcgggggggcg cagtgcacac gagggggctg    120

gacttcgcct gtgat                                                     135


<210> SEQ ID NO 27
<211> LENGTH: 39
<212> TYPE: PRT
<213> ORGANISM: Artificial sequence
<220> FEATURE:
<223> OTHER INFORMATION: CD28 hinge region

<400> SEQUENCE: 27

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 28
<211> LENGTH: 117
<212> TYPE: DNA
<213> ORGANISM: Artificial sequence
<220> FEATURE:
<223> OTHER INFORMATION: CD28 hinge region

<400> SEQUENCE: 28

attgaagtta tgtatcctcc tccttaccta gacaatgaga agagcaatgg aaccattatc     60

catgtgaaag ggaaacacct ttgtccaagt cccctatttc ccggaccttc taagccc       117


<210> SEQ ID NO 29
<211> LENGTH: 12
<212> TYPE: PRT
<213> ORGANISM: Artificial sequence
<220> FEATURE:
<223> OTHER INFORMATION: IgG4 hinge region

<400> SEQUENCE: 29

Glu Ser Lys Tyr Gly Pro Pro Cys Pro Pro Cys Pro
1               5                   10


<210> SEQ ID NO 30
<211> LENGTH: 36
<212> TYPE: DNA
<213> ORGANISM: Artificial sequence
<220> FEATURE:
<223> OTHER INFORMATION: IgG4 hinge region

<400> SEQUENCE: 30

gaaagcaaat acgggccgcc gtgtccaccc tgtccg                               36


<210> SEQ ID NO 31
<211> LENGTH: 284
<212> TYPE: PRT
<213> ORGANISM: Artificial sequence
<220> FEATURE:
<223> OTHER INFORMATION: HLA-E extracellular region

<400> SEQUENCE: 31

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
```

```
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala Gly Ser His Thr Leu Gln
                85                  90                  95

Trp Met His Gly Cys Glu Leu Gly Pro Asp Gly Arg Phe Leu Arg Gly
            100                 105                 110

Tyr Glu Gln Phe Ala Tyr Asp Gly Lys Asp Tyr Leu Thr Leu Asn Glu
        115                 120                 125

Asp Leu Arg Ser Trp Thr Ala Val Asp Thr Ala Ala Gln Ile Ser Glu
    130                 135                 140

Gln Lys Ser Asn Asp Ala Ser Glu Ala Glu His Gln Arg Ala Tyr Leu
145                 150                 155                 160

Glu Asp Thr Cys Val Glu Trp Leu His Lys Tyr Leu Glu Lys Gly Lys
                165                 170                 175

Glu Thr Leu Leu His Leu Glu Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Gln Asp Gly Glu Gly His
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Val Thr Leu
            260                 265                 270

Arg Trp Lys Pro Ala Ser Gln Pro Thr Ile Pro Ile
        275                 280


<210> SEQ ID NO 32
<211> LENGTH: 852
<212> TYPE: DNA
<213> ORGANISM: Artificial sequence
<220> FEATURE:
<223> OTHER INFORMATION: HLA-E extracellular region

<400> SEQUENCE: 32

ggctcccact ctttgaagta cttccacacc agcgtgagca ggccgggcag gggtgaacca     60

agatttataa gtgttgggta tgtggacgat acacaatttg tgcgctttga taacgacgcg    120

gcttctcctc gaatggtgcc ccgcgcccct tggatggaac aagagggttc tgagtattgg    180

gatagggaaa cccgctccgc ccgagataca gcccagatct ttagagttaa cttgcgaaca    240

ctcagaggtt attataacca gagcgaggca ggttcacaca ccctccagtg gatgcacggg    300

tgtgagcttg gtcctgatgg ccgctttctc cggggttacg agcaatttgc ttatgatggg    360

aaggattatc ttacactcaa cgaggatctt cgatcctgga ccgcagtgga caccgcagcg    420

cagatttctg aacagaagtc caatgacgcg tcagaggcag aacaccaacg ggcgtatctg    480

gaagatacct gtgttgagtg gctgcataaa tacctcgaga aggaaaaaga gacgcttctc    540

catctcgaac cgcctaaaac tcacgtaact catcacccta taagtgacca cgaagccacg    600
```

ttgaggtgtt gggctctcgg tttttaccct gctgaaatca cactgacttg gcagcaggat 660
ggggagggcc acacccagga tacagaactc gttgaaactc gaccagcagg agacgggacg 720
tttcaaaagt gggccgcggt agtggttcct agtggtgagg aacagcggta cacttgccat 780
gttcaacacg aggggcttcc ggagccagtt accctccgat ggaaaccggc gtcacagcct 840
acaataccga tt 852

<210> SEQ ID NO 33
<211> LENGTH: 284
<212> TYPE: PRT
<213> ORGANISM: Artificial sequence
<220> FEATURE:
<223> OTHER INFORMATION: HLA-E extracellular region mutant

<400> SEQUENCE: 33

Gly Ser His Ser Leu Lys Tyr Phe His Thr Ser Val Ser Arg Pro Gly
1 5 10 15

Arg Gly Glu Pro Arg Phe Ile Ser Val Gly Tyr Val Asp Asp Thr Gln
20 25 30

Phe Val Arg Phe Asp Asn Asp Ala Ala Ser Pro Arg Met Val Pro Arg
35 40 45

Ala Pro Trp Met Glu Gln Glu Gly Ser Glu Tyr Trp Asp Arg Glu Thr
50 55 60

Arg Ser Ala Arg Asp Thr Ala Gln Ile Phe Arg Val Asn Leu Arg Thr
65 70 75 80

Leu Arg Gly Cys Tyr Asn Gln Ser Glu Ala Gly Ser His Thr Leu Gln
85 90 95

Trp Met His Gly Cys Glu Leu Gly Pro Asp Gly Arg Phe Leu Arg Gly
100 105 110

Tyr Glu Gln Phe Ala Tyr Asp Gly Lys Asp Tyr Leu Thr Leu Asn Glu
115 120 125

Asp Leu Arg Ser Trp Thr Ala Val Asp Thr Ala Ala Gln Ile Ser Glu
130 135 140

Gln Lys Ser Asn Asp Ala Ser Glu Ala Glu His Gln Arg Ala Tyr Leu
145 150 155 160

Glu Asp Thr Cys Val Glu Trp Leu His Lys Tyr Leu Glu Lys Gly Lys
165 170 175

Glu Thr Leu Leu His Leu Glu Pro Pro Lys Thr His Val Thr His His
180 185 190

Pro Ile Ser Asp His Glu Ala Thr Leu Arg Cys Trp Ala Leu Gly Phe
195 200 205

Tyr Pro Ala Glu Ile Thr Leu Thr Trp Gln Gln Asp Gly Glu Gly His
210 215 220

Thr Gln Asp Thr Glu Leu Val Glu Thr Arg Pro Ala Gly Asp Gly Thr
225 230 235 240

Phe Gln Lys Trp Ala Ala Val Val Val Pro Ser Gly Glu Glu Gln Arg
245 250 255

Tyr Thr Cys His Val Gln His Glu Gly Leu Pro Glu Pro Val Thr Leu
260 265 270

Arg Trp Lys Pro Ala Ser Gln Pro Thr Ile Pro Ile
275 280

<210> SEQ ID NO 34
<211> LENGTH: 852
<212> TYPE: DNA

<213> ORGANISM: Artificial sequence
<220> FEATURE:
<223> OTHER INFORMATION: HLA-E extracellular region mutant

<400> SEQUENCE: 34

```
ggctcccact ccttgaagta tttccacact tccgtgtccc ggcccggccg cggggagccc     60

cgcttcatct ctgtgggcta cgtggacgac acccagttcg tgcgcttcga caacgacgcc    120

gcgagtccga ggatggtgcc gcgggcgccg tggatggagc aggaggggtc agagtattgg    180

gaccgggaga cacggagcgc cagggacacc gcacagattt tccgagtgaa tctgcggacg    240

ctgcgcggct gctacaatca gagcgaggcc gggtctcaca ccctgcagtg gatgcatggc    300

tgcgagctgg ggcccgacgg gcgcttcctc cgcgggtatg aacagttcgc ctacgacggc    360

aaggattatc tcaccctgaa tgaggacctg cgctcctgga ccgcggtgga cacggcggct    420

cagatctccg agcaaaagtc aaatgatgcc tctgaggcgg agcaccagag agcctacctg    480

gaagacacat gcgtggagtg gctccacaaa tacctggaga aggggaagga gacgctgctt    540

cacctggagc ccccaaagac acacgtgact caccacccca tctctgacca tgaggccacc    600

ctgaggtgct gggccctggg cttctaccct gcggagatca cactgacctg gcagcaggat    660

ggggagggcc atacccagga cacggagctc gtggagacca ggcctgcagg ggatggaacc    720

ttccagaagt gggcagctgt ggtggtgcct tctggagagg agcagagata cacgtgccat    780

gtgcagcatg aggggctacc cgagcccgtc accctgagat ggaagccggc ttcccagccc    840

accatcccca tc                                                        852
```

<210> SEQ ID NO 35
<211> LENGTH: 283
<212> TYPE: PRT
<213> ORGANISM: Artificial sequence
<220> FEATURE:
<223> OTHER INFORMATION: HLA-G extracellular region

<400> SEQUENCE: 35

```
Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
    50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Ser Ser His Thr Leu Gln
                85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
    130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175
```

```
Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
    210                 215                 220

Thr Gln Asp Val Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Met Leu
            260                 265                 270

Arg Trp Lys Gln Ser Ser Leu Pro Thr Ile Pro
        275                 280
```

<210> SEQ ID NO 36
<211> LENGTH: 849
<212> TYPE: DNA
<213> ORGANISM: Artificial sequence
<220> FEATURE:
<223> OTHER INFORMATION: HLA-G extracellular region

<400> SEQUENCE: 36

```
ggctcccact ccatgaggta tttcagcgcc gccgtgtccc ggcccggccg cggggagccc     60

cgcttcatcg ccatgggcta cgtggacgac acgcagttcg tgcggttcga cagcgactcg    120

gcgtgtccga ggatggagcc gcgggcgccg tgggtggagc aggaggggcc ggagtattgg    180

gaagaggaga cacggaacac caaggcccac gcacagactg acagaatgaa cctgcagacc    240

ctgcgcggct actacaacca gagcgaggcc agttctcaca ccctccagtg gatgattggc    300

tgcgacctgg ggtccgacgg acgcctcctc cgcgggtatg aacagtatgc ctacgatggc    360

aaggattacc tcgccctgaa cgaggacctg cgctcctgga ccgcagcgga cactgcggct    420

cagatctcca agcgcaagtg tgaggcggcc aatgtggctg aacaaaggag agcctacctg    480

gagggcacgt gcgtggagtg gctccacaga tacctggaga acgggaagga gatgctgcag    540

cgcgcggacc cccccaagac acacgtgacc caccaccctg tctttgacta tgaggccacc    600

ctgaggtgct gggccctggg cttctaccct gcggagatca tactgacctg gcagcgggat    660

ggggaggacc agacccagga cgtggagctc gtggagacca ggcctgcagg ggatggaacc    720

ttccagaagt gggcagctgt ggtggtgcct tctggagagg agcagagata cacgtgccat    780

gtgcagcatg aggggctgcc ggagcccctc atgctgagat ggaagcagtc ttccctgccc    840

accatcccc                                                            849
```

<210> SEQ ID NO 37
<211> LENGTH: 99
<212> TYPE: PRT
<213> ORGANISM: Artificial sequence
<220> FEATURE:
<223> OTHER INFORMATION: B2M

<400> SEQUENCE: 37

```
Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45
```

```
Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 38
<211> LENGTH: 297
<212> TYPE: DNA
<213> ORGANISM: Artificial sequence
<220> FEATURE:
<223> OTHER INFORMATION: synonymous B2M

<400> SEQUENCE: 38

atccagagga ccccgaagat ccaggtttat tctcggcatc ctgccgaaaa tggaaaaagc      60

aattttctca actgttatgt gtctggattt cacccatctg acatagaggt tgaccttctt     120

aagaatggcg agagaatcga gaaggtcgaa cattcagact tgagcttcag caaggattgg     180

agcttttatc ttctttatta tactgaattt actcccactg aaaaggatga atacgcctgc     240

agggtaaacc atgtaacact cagtcagcca aagatcgtaa aatgggaccg agacatg        297


<210> SEQ ID NO 39
<211> LENGTH: 689
<212> TYPE: PRT
<213> ORGANISM: Artificial sequence
<220> FEATURE:
<223> OTHER INFORMATION: E-cadherin EC1-EC5

<400> SEQUENCE: 39

Trp Leu Cys Gln Glu Pro Glu Pro Cys His Pro Gly Phe Asp Ala Glu
1               5                   10                  15

Ser Tyr Thr Phe Thr Val Pro Arg Arg His Leu Glu Arg Gly Arg Val
            20                  25                  30

Leu Gly Arg Val Asn Phe Glu Asp Cys Thr Gly Arg Gln Arg Thr Ala
        35                  40                  45

Tyr Phe Ser Leu Asp Thr Arg Phe Lys Val Gly Thr Asp Gly Val Ile
    50                  55                  60

Thr Val Lys Arg Pro Leu Arg Phe His Asn Pro Gln Ile His Phe Leu
65                  70                  75                  80

Val Tyr Ala Trp Asp Ser Thr Tyr Arg Lys Phe Ser Thr Lys Val Thr
                85                  90                  95

Leu Asn Thr Val Gly His His His Arg Pro Pro Pro His Gln Ala Ser
            100                 105                 110

Val Ser Gly Ile Gln Ala Glu Leu Leu Thr Phe Pro Asn Ser Ser Pro
        115                 120                 125

Gly Leu Arg Arg Gln Lys Arg Asp Trp Val Ile Pro Pro Ile Ser Cys
    130                 135                 140

Pro Glu Asn Glu Lys Gly Pro Phe Pro Lys Asn Leu Val Gln Ile Lys
145                 150                 155                 160

Ser Asn Lys Asp Lys Glu Gly Lys Val Phe Tyr Ser Ile Thr Gly Gln
                165                 170                 175

Gly Ala Asp Thr Pro Pro Val Gly Val Phe Ile Ile Glu Arg Glu Thr
            180                 185                 190

Gly Trp Leu Lys Val Thr Glu Pro Leu Asp Arg Glu Arg Ile Ala Thr
```

```
        195                 200                 205

Tyr Thr Leu Phe Ser His Ala Val Ser Ser Asn Gly Asn Ala Val Glu
    210                 215                 220

Asp Pro Met Glu Ile Leu Ile Thr Val Thr Asp Gln Asn Asp Asn Lys
225                 230                 235                 240

Pro Glu Phe Thr Gln Glu Val Phe Lys Gly Ser Val Met Glu Gly Ala
                245                 250                 255

Leu Pro Gly Thr Ser Val Met Glu Val Thr Ala Thr Asp Ala Asp Asp
            260                 265                 270

Asp Val Asn Thr Tyr Asn Ala Ala Ile Ala Tyr Thr Ile Leu Ser Gln
        275                 280                 285

Asp Pro Glu Leu Pro Asp Lys Asn Met Phe Thr Ile Asn Arg Asn Thr
    290                 295                 300

Gly Val Ile Ser Val Val Thr Thr Gly Leu Asp Arg Glu Ser Phe Pro
305                 310                 315                 320

Thr Tyr Thr Leu Val Val Gln Ala Ala Asp Leu Gln Gly Glu Gly Leu
                325                 330                 335

Ser Thr Thr Ala Thr Ala Val Ile Thr Val Thr Asp Thr Asn Asp Asn
            340                 345                 350

Pro Pro Ile Phe Asn Pro Thr Thr Tyr Lys Gly Gln Val Pro Glu Asn
        355                 360                 365

Glu Ala Asn Val Val Ile Thr Thr Leu Lys Val Thr Asp Ala Asp Ala
    370                 375                 380

Pro Asn Thr Pro Ala Trp Glu Ala Val Tyr Thr Ile Leu Asn Asp Asp
385                 390                 395                 400

Gly Gly Gln Phe Val Val Thr Thr Asn Pro Val Asn Asn Asp Gly Ile
                405                 410                 415

Leu Lys Thr Ala Lys Gly Leu Asp Phe Glu Ala Lys Gln Gln Tyr Ile
            420                 425                 430

Leu His Val Ala Val Thr Asn Val Val Pro Phe Glu Val Ser Leu Thr
        435                 440                 445

Thr Ser Thr Ala Thr Val Thr Val Asp Val Leu Asp Val Asn Glu Ala
    450                 455                 460

Pro Ile Phe Val Pro Pro Glu Lys Arg Val Glu Val Ser Glu Asp Phe
465                 470                 475                 480

Gly Val Gly Gln Glu Ile Thr Ser Tyr Thr Ala Gln Glu Pro Asp Thr
                485                 490                 495

Phe Met Glu Gln Lys Ile Thr Tyr Arg Ile Trp Arg Asp Thr Ala Asn
            500                 505                 510

Trp Leu Glu Ile Asn Pro Asp Thr Gly Ala Ile Ser Thr Arg Ala Glu
        515                 520                 525

Leu Asp Arg Glu Asp Phe Glu His Val Lys Asn Ser Thr Tyr Thr Ala
    530                 535                 540

Leu Ile Ile Ala Thr Asp Asn Gly Ser Pro Val Ala Thr Gly Thr Gly
545                 550                 555                 560

Thr Leu Leu Leu Ile Leu Ser Asp Val Asn Asp Asn Ala Pro Ile Pro
                565                 570                 575

Glu Pro Arg Thr Ile Phe Phe Cys Glu Arg Asn Pro Lys Pro Gln Val
            580                 585                 590

Ile Asn Ile Ile Asp Ala Asp Leu Pro Pro Asn Thr Ser Pro Phe Thr
        595                 600                 605

Ala Glu Leu Thr His Gly Ala Ser Ala Asn Trp Thr Ile Gln Tyr Asn
    610                 615                 620
```

```
Asp Pro Thr Gln Glu Ser Ile Ile Leu Lys Pro Lys Met Ala Leu Glu
625                 630                 635                 640

Val Gly Asp Tyr Lys Ile Asn Leu Lys Leu Met Asp Asn Gln Asn Lys
                645                 650                 655

Asp Gln Val Thr Thr Leu Glu Val Ser Val Cys Asp Cys Glu Gly Ala
            660                 665                 670

Ala Gly Val Cys Arg Lys Ala Gln Pro Val Glu Ala Gly Leu Gln Ile
        675                 680                 685

Pro


<210> SEQ ID NO 40
<211> LENGTH: 2067
<212> TYPE: DNA
<213> ORGANISM: Artificial sequence
<220> FEATURE:
<223> OTHER INFORMATION: E-cadherin EC1-EC5

<400> SEQUENCE: 40

tggctttgcc aggagccaga accctgtcat cctggcttcg atgcggagtc atacacgttt     60

accgtgccac gaagacatct cgagagggga agagtcctcg ggcgcgtgaa ctttgaagac    120

tgtacggggc gccaacggac tgcatatttc tccctcgaca cgagattcaa ggtcggcaca    180

gacggcgtaa ttacagtaaa acgcccgctt agattccata accctcagat acatttcttg    240

gtctatgcgt gggatagtac ctatcggaag ttttcaacaa aggtaacact taataccgta    300

ggtcatcatc atagaccccc tccgcaccaa gcgtctgtgt ctggcattca ggcggaattg    360

ttgaccttcc caaactcttc accggggctg aggcgccaaa aacgagactg ggtcatcccg    420

cctattagct gtccagagaa tgaaaaagga cccttcccta aaaaccttgt acagattaaa    480

tctaataagg acaaagaggg taaggttttt tacagtatta cgggccaggg tgctgacacc    540

ccaccggtag gcgtattcat catcgagaga gaaaccggtt ggctcaaagt gactgagcca    600

ctcgacagag agagaattgc aacttacacc cttttcagtc acgcggtttc aagcaacgga    660

aatgcagtgg aagaccccat ggagattctc atcaccgtga cagatcaaaa tgataacaaa    720

cctgaattta cccaggaggt gtttaaaggg agcgtaatgg aaggtgcact tcctggtacg    780

tctgttatgg aagtaactgc cacagatgct gatgatgacg taaacaccta taatgctgcc    840

atagcctaca cgatcctgag tcaagatccc gaactgcccg acaaaaatat gttcacaata    900

aatcgcaaca caggggtgat atccgttgtt acgaccggct tggatcggga gtcttttcca    960

acttatacgc tcgttgtaca agcggcggac ttgcaagggg aaggactcag tacgaccgcc   1020

acagcagtaa taaccgttac cgatacaaat gacaaccctc caatcttcaa tccaactacg   1080

tacaaaggac aggtgcctga gaacgaggca aacgttgtca ttacaacgct taaagtcacc   1140

gatgctgatg ctccgaatac cccggcatgg gaggctgtgt acactattct gaatgatgat   1200

ggcggtcagt ttgtggtaac tacgaacccc gtcaacaacg acggaatcct caaaacagct   1260

aagggattgg atttcgaggc taagcaacaa tatatccttc atgtggcagt aacgaacgtg   1320

gtaccctttg aagtatccct tactacttca accgctacag tcactgttga cgtcctcgat   1380

gttaacgagg cacctatctt cgttcctcca gagaaacgcg tggaagtaag tgaggacttc   1440

ggcgttgggc aagaaattac gtcttataca gctcaagagc ctgatacatt tatggagcaa   1500

aagatcacat accgcatttg gagagatacg gcaaactggc tcgaaataaa tcctgatacg   1560

ggagcaataa gcacacgggc tgagttggac cgagaggatt ttgaacacgt caagaactcc   1620
```

```
acgtatacgg ccttgatcat cgcgactgat aatgggagtc ctgtggcaac aggaacgggc   1680

accctcttgt tgatcttgtc tgatgttaat gacaacgcgc caatcccaga accgaggacc   1740

atcttctttt gtgaaagaaa cccaaagccc caagtgataa acatcattga cgccgatctg   1800

ccaccaaaca cgtccccctt tacagccgag cttacacatg gggcgtcagc aaattggacg   1860

attcaataca acgaccctac gcaagaatca ataattctta agccaaaaat ggcgttggaa   1920

gtcggggact ataagatcaa cctgaagctc atggacaacc agaataaaga ccaagtaacg   1980

acacttgaag tctcagtttg tgattgcgag gggcggctgg gagtttgtcg gaaggcccaa   2040

cctgttgaag ccggcttgca gataccg                                       2067
```

```
<210> SEQ ID NO 41
<211> LENGTH: 356
<212> TYPE: PRT
<213> ORGANISM: Artificial sequence
<220> FEATURE:
<223> OTHER INFORMATION: E-cadherin EC1-EC2

<400> SEQUENCE: 41

Trp Leu Cys Gln Glu Pro Glu Pro Cys His Pro Gly Phe Asp Ala Glu
1               5                   10                  15

Ser Tyr Thr Phe Thr Val Pro Arg Arg His Leu Glu Arg Gly Arg Val
            20                  25                  30

Leu Gly Arg Val Asn Phe Glu Asp Cys Thr Gly Arg Gln Arg Thr Ala
        35                  40                  45

Tyr Phe Ser Leu Asp Thr Arg Phe Lys Val Gly Thr Asp Gly Val Ile
    50                  55                  60

Thr Val Lys Arg Pro Leu Arg Phe His Asn Pro Gln Ile His Phe Leu
65                  70                  75                  80

Val Tyr Ala Trp Asp Ser Thr Tyr Arg Lys Phe Ser Thr Lys Val Thr
                85                  90                  95

Leu Asn Thr Val Gly His His His Arg Pro Pro Pro His Gln Ala Ser
            100                 105                 110

Val Ser Gly Ile Gln Ala Glu Leu Leu Thr Phe Pro Asn Ser Ser Pro
        115                 120                 125

Gly Leu Arg Arg Gln Lys Arg Asp Trp Val Ile Pro Pro Ile Ser Cys
    130                 135                 140

Pro Glu Asn Glu Lys Gly Pro Phe Pro Lys Asn Leu Val Gln Ile Lys
145                 150                 155                 160

Ser Asn Lys Asp Lys Glu Gly Lys Val Phe Tyr Ser Ile Thr Gly Gln
                165                 170                 175

Gly Ala Asp Thr Pro Pro Val Gly Val Phe Ile Ile Glu Arg Glu Thr
            180                 185                 190

Gly Trp Leu Lys Val Thr Glu Pro Leu Asp Arg Glu Arg Ile Ala Thr
        195                 200                 205

Tyr Thr Leu Phe Ser His Ala Val Ser Ser Asn Gly Asn Ala Val Glu
    210                 215                 220

Asp Pro Met Glu Ile Leu Ile Thr Val Thr Asp Gln Asn Asp Asn Lys
225                 230                 235                 240

Pro Glu Phe Thr Gln Glu Val Phe Lys Gly Ser Val Met Glu Gly Ala
                245                 250                 255

Leu Pro Gly Thr Ser Val Met Glu Val Thr Ala Thr Asp Ala Asp Asp
            260                 265                 270

Asp Val Asn Thr Tyr Asn Ala Ala Ile Ala Tyr Thr Ile Leu Ser Gln
        275                 280                 285
```

```
Asp Pro Glu Leu Pro Asp Lys Asn Met Phe Thr Ile Asn Arg Asn Thr
    290                 295                 300

Gly Val Ile Ser Val Val Thr Thr Gly Leu Asp Arg Glu Ser Phe Pro
305                 310                 315                 320

Thr Tyr Thr Leu Val Val Gln Ala Ala Asp Leu Gln Gly Glu Gly Leu
                325                 330                 335

Ser Thr Thr Ala Thr Ala Val Ile Thr Val Thr Asp Thr Asn Asp Asn
            340                 345                 350

Pro Pro Ile Phe
        355
```

<210> SEQ ID NO 42
<211> LENGTH: 1068
<212> TYPE: DNA
<213> ORGANISM: Artificial sequence
<220> FEATURE:
<223> OTHER INFORMATION: E-cadherin EC1-EC2

<400> SEQUENCE: 42

```
tggttgtgcc aggaacccga gccttgccat cccggattcg atgcagagtc atatacattt      60

acggtacccc gccgacatct ggagcgaggg cgggttctcg ggagagttaa ctttgaagac     120

tgcaccggca ggcagcggac cgcctacttt tcattggata cgcgattcaa agtcggcacc     180

gatggcgtca taaccgttaa acggccactg cgcttccata atccacaaat tcatttcctc     240

gtatacgcat gggacagtac ttatcgcaag ttcagcacaa aagttacact taatacggta     300

gggcatcacc acaggcctcc accccaccag gcttcagtga gtggcataca ggctgaactc     360

ctgacatttc caaattcttc acccggactc agaagacaaa agcgcgactg ggtcattcca     420

cctatttcct gtccagagaa cgaaaaaggg ccgttcccga aaaatctggt tcaaattaaa     480

agtaacaaag ataaagaggg taaagtgttt tacagtataa ccggccaggg cgccgatact     540

cctcccgtcg ggtctttat catcgaacgg gaaactggtt ggcttaaagt aacagaaccc      600

ctcgataggg aacggatagc aacgtataca ctgttcagtc atgcagttag cagcaatggc     660

aacgcagtag aagaccctat ggaaatcctc attactgtta ctgaccaaaa tgataacaag     720

cccgagttta cacaggaggt attcaagggc tcagtaatgg agggcgcgct tccagggacc     780

agtgttatgg aggtaactgc gaccgatgcg gatgacgatg tgaacacgta caacgctgcg     840

atagcctata ccattttgtc acaggatcct gaactcccgg acaaaaacat gttcacaata     900

aaccggaaca caggagtcat atcagtggtg actacaggcc ttgaccgcga atcctttcct     960

acgtatactc tcgtggtcca agcggcagat ctgcaaggtg aagggctgag tacaacggcc    1020

actgccgtaa ttactgtcac cgacactaat gacaatccac ccatattc                 1068
```

<210> SEQ ID NO 43
<211> LENGTH: 20
<212> TYPE: RNA
<213> ORGANISM: Artificial sequence
<220> FEATURE:
<223> OTHER INFORMATION: TRAC sgRNA

<400> SEQUENCE: 43

```
agagucucuc agcugguaca                                                  20
```

<210> SEQ ID NO 44
<211> LENGTH: 20
<212> TYPE: RNA
<213> ORGANISM: Artificial sequence
<220> FEATURE:
<223> OTHER INFORMATION: B2M sgRNA

<400> SEQUENCE: 44
ggguagcgcg agcacagcua 20

<210> SEQ ID NO 45
<211> LENGTH: 19
<212> TYPE: RNA
<213> ORGANISM: Artificial sequence
<220> FEATURE:
<223> OTHER INFORMATION: RFX5 sgRNA

<400> SEQUENCE: 45
ggguugcgga uccaccuau 19

<210> SEQ ID NO 46
<211> LENGTH: 9
<212> TYPE: PRT
<213> ORGANISM: Artificial sequence
<220> FEATURE:
<223> OTHER INFORMATION: presenting peptide

<400> SEQUENCE: 46

Val Met Ala Pro Arg Thr Leu Ile Leu
1 5

<210> SEQ ID NO 47
<211> LENGTH: 9
<212> TYPE: PRT
<213> ORGANISM: Artificial sequence
<220> FEATURE:
<223> OTHER INFORMATION: presenting peptide

<400> SEQUENCE: 47

Val Met Ala Pro Arg Thr Leu Phe Leu
1 5

<210> SEQ ID NO 48
<211> LENGTH: 9
<212> TYPE: PRT
<213> ORGANISM: Artificial sequence
<220> FEATURE:
<223> OTHER INFORMATION: presenting peptide

<400> SEQUENCE: 48

Val Met Ala Pro Leu Thr Leu Ile Leu
1 5

<210> SEQ ID NO 49
<211> LENGTH: 9
<212> TYPE: PRT
<213> ORGANISM: Artificial sequence
<220> FEATURE:
<223> OTHER INFORMATION: presenting peptide

<400> SEQUENCE: 49

Val Met Ala Pro Arg Ile Leu Ile Leu
1 5

<210> SEQ ID NO 50
<211> LENGTH: 9
<212> TYPE: PRT
<213> ORGANISM: Artificial sequence
<220> FEATURE:
<223> OTHER INFORMATION: presenting peptide

<400> SEQUENCE: 50

Val Met Ala Pro Gln Ser Leu Leu Leu
5

<210> SEQ ID NO 51
<211> LENGTH: 9
<212> TYPE: PRT
<213> ORGANISM: Artificial sequence
<220> FEATURE:
<223> OTHER INFORMATION: presenting peptide

<400> SEQUENCE: 51

Gln Met Arg Pro Val Ser Arg Val Leu
5

<210> SEQ ID NO 52
<211> LENGTH: 9
<212> TYPE: PRT
<213> ORGANISM: Artificial sequence
<220> FEATURE:
<223> OTHER INFORMATION: presenting peptide

<400> SEQUENCE: 52

Gly Met Lys Phe Asp Arg Gly Tyr Ile
5

<210> SEQ ID NO 53
<211> LENGTH: 9
<212> TYPE: PRT
<213> ORGANISM: Artificial sequence
<220> FEATURE:
<223> OTHER INFORMATION: presenting peptide

<400> SEQUENCE: 53

Ala Ile Ser Pro Arg Thr Leu Asn Ala
5

<210> SEQ ID NO 54
<211> LENGTH: 195
<212> TYPE: PRT
<213> ORGANISM: Artificial sequence
<220> FEATURE:
<223> OTHER INFORMATION: KLRG1

<400> SEQUENCE: 54

Met Thr Asp Ser Val Ile Tyr Ser Met Leu Glu Leu Pro Thr Ala Thr
1 5 10 15

Gln Ala Gln Asn Asp Tyr Gly Pro Gln Gln Lys Ser Ser Ser Ser Arg
20 25 30

Pro Ser Cys Ser Cys Leu Val Ala Ile Ala Leu Gly Leu Leu Thr Ala
35 40 45

Val Leu Leu Ser Val Leu Leu Tyr Gln Trp Ile Leu Cys Gln Gly Ser
50 55 60

Asn Tyr Ser Thr Cys Ala Ser Cys Pro Ser Cys Pro Asp Arg Trp Met
65 70 75 80

Lys Tyr Gly Asn His Cys Tyr Tyr Phe Ser Val Glu Glu Lys Asp Trp
85 90 95

Asn Ser Ser Leu Glu Phe Cys Leu Ala Arg Asp Ser His Leu Leu Val
100 105 110

Ile Thr Asp Asn Gln Glu Met Ser Leu Leu Gln Val Phe Leu Ser Glu
115 120 125

Ala Phe Cys Trp Ile Gly Leu Arg Asn Asn Ser Gly Trp Arg Trp Glu

```
    130                 135                 140

Asp Gly Ser Pro Leu Asn Phe Ser Arg Ile Ser Ser Asn Ser Phe Val
145                 150                 155                 160

Gln Thr Cys Gly Ala Ile Asn Lys Asn Gly Leu Gln Ala Ser Ser Cys
                165                 170                 175

Glu Val Pro Leu His Trp Val Cys Lys Lys Cys Pro Phe Ala Asp Gln
            180                 185                 190

Ala Leu Phe
        195


<210> SEQ ID NO 55
<211> LENGTH: 108
<212> TYPE: PRT
<213> ORGANISM: Artificial sequence
<220> FEATURE:
<223> OTHER INFORMATION: KIR scFv VL

<400> SEQUENCE: 55

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg
            100                 105


<210> SEQ ID NO 56
<211> LENGTH: 123
<212> TYPE: PRT
<213> ORGANISM: Artificial sequence
<220> FEATURE:
<223> OTHER INFORMATION: KIR scFv VH

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120
```

<210> SEQ ID NO 57
<211> LENGTH: 246
<212> TYPE: PRT
<213> ORGANISM: Artificial sequence
<220> FEATURE:
<223> OTHER INFORMATION: KIR scFv

<400> SEQUENCE: 57

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Val Thr Leu Ser Leu Ser Pro Gly Glu Arg Ala Thr Leu Ser
145                 150                 155                 160

Cys Arg Ala Ser Gln Ser Val Ser Ser Tyr Leu Ala Trp Tyr Gln Gln
                165                 170                 175

Lys Pro Gly Gln Ala Pro Arg Leu Leu Ile Tyr Asp Ala Ser Asn Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Asn Trp Met Tyr Thr Phe Gly Gln Gly Thr
225                 230                 235                 240

Lys Leu Glu Ile Lys Arg
                245
```

<210> SEQ ID NO 58
<211> LENGTH: 109
<212> TYPE: PRT
<213> ORGANISM: Artificial sequence
<220> FEATURE:
<223> OTHER INFORMATION: KIR scFv VL

<400> SEQUENCE: 58

```
Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Met Tyr
85 90 95

Thr Phe Gly Gln Gly Thr Lys Leu Glu Ile Lys Arg Thr
100 105

<210> SEQ ID NO 59
<211> LENGTH: 123
<212> TYPE: PRT
<213> ORGANISM: Artificial sequence
<220> FEATURE:
<223> OTHER INFORMATION: KIR scFv VH

<400> SEQUENCE: 59

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Phe Tyr
20 25 30

Ala Ile Ser Trp Val Arg Gln Ala Pro Gly Gln Gly Leu Glu Trp Met
35 40 45

Gly Gly Phe Ile Pro Ile Phe Gly Ala Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Asp Asp Thr Ala Val Tyr Tyr Cys
85 90 95

Ala Arg Ile Pro Ser Gly Ser Tyr Tyr Tyr Asp Tyr Asp Met Asp Val
100 105 110

Trp Gly Gln Gly Thr Thr Val Thr Val Ser Ser
115 120

<210> SEQ ID NO 60
<211> LENGTH: 247
<212> TYPE: PRT
<213> ORGANISM: Artificial sequence
<220> FEATURE:
<223> OTHER INFORMATION: KIR scFv

<400> SEQUENCE: 60

Glu Ile Val Leu Thr Gln Ser Pro Val Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Met Tyr
85 90 95

Thr Phe Gly Gln Gly Thr Lys Leu Glu Ile Lys Arg Thr Gly Gly Gly
100 105 110

Gly Ser Gly Gly Gly Gly Ser Gly Gly Gly Gly Ser Gln Val Gln Leu
115 120 125

Val Gln Ser Gly Ala Glu Val Lys Lys Pro Gly Ser Ser Val Lys Val

```
    130                 135                 140

Ser Cys Lys Ala Ser Gly Gly Thr Phe Ser Phe Tyr Ala Ile Ser Trp
145                 150                 155                 160

Val Arg Gln Ala Pro Gly Gln Gly Leu Glu Trp Met Gly Gly Phe Ile
                165                 170                 175

Pro Ile Phe Gly Ala Ala Asn Tyr Ala Gln Lys Phe Gln Gly Arg Val
            180                 185                 190

Thr Ile Thr Ala Asp Glu Ser Thr Ser Thr Ala Tyr Met Glu Leu Ser
        195                 200                 205

Ser Leu Arg Ser Asp Asp Thr Ala Val Tyr Tyr Cys Ala Arg Ile Pro
    210                 215                 220

Ser Gly Ser Tyr Tyr Tyr Asp Tyr Asp Met Asp Val Trp Gly Gln Gly
225                 230                 235                 240

Thr Thr Val Thr Val Ser Ser
                245


<210> SEQ ID NO 61
<211> LENGTH: 107
<212> TYPE: PRT
<213> ORGANISM: Artificial sequence
<220> FEATURE:
<223> OTHER INFORMATION: LIR1 scFv-1 VL

<400> SEQUENCE: 61

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Tyr Ser Trp Pro Tyr
                85                  90                  95

Thr Phe Gly Gly Gly Thr Lys Leu Glu Ile Lys
            100                 105


<210> SEQ ID NO 62
<211> LENGTH: 118
<212> TYPE: PRT
<213> ORGANISM: Artificial sequence
<220> FEATURE:
<223> OTHER INFORMATION: LIR1 scFv-1 VH

<400> SEQUENCE: 62

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Leu Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Leu Pro Ser
    50                  55                  60

Leu Lys Ser Gln Leu Thr Ile Ser Lys Asp Thr Ser Arg Asn Gln Val
65                  70                  75                  80
```

```
Phe Leu Lys Ile Thr Ser Val Asp Thr Ala Asp Thr Ala Thr Tyr Tyr
                85                  90                  95

Cys Ala Arg Thr Glu Leu Gly Arg Gly Asp Tyr Trp Gly Gln Gly Thr
            100                 105                 110

Ser Val Ala Val Ser Ser
        115


<210> SEQ ID NO 63
<211> LENGTH: 243
<212> TYPE: PRT
<213> ORGANISM: Artificial sequence
<220> FEATURE:
<223> OTHER INFORMATION: LIR1 scFv-2

<400> SEQUENCE: 63

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Tyr Ser Trp Pro Tyr
                85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Gln Val Thr
        115                 120                 125

Leu Lys Glu Ser Gly Pro Gly Ile Leu Lys Pro Ser Gln Thr Leu Ser
    130                 135                 140

Leu Thr Cys Ser Phe Ser Gly Phe Ser Leu Ser Thr Ser Gly Leu Gly
145                 150                 155                 160

Val Gly Trp Ile Arg Gln Pro Ser Gly Lys Gly Leu Glu Trp Leu Ala
                165                 170                 175

His Ile Trp Trp Asp Asp Asp Lys Tyr Tyr Leu Pro Ser Leu Lys Ser
            180                 185                 190

Gln Leu Thr Ile Ser Lys Asp Thr Ser Arg Asn Gln Val Phe Leu Lys
        195                 200                 205

Ile Thr Ser Val Asp Thr Ala Asp Thr Ala Thr Tyr Tyr Cys Ala Arg
    210                 215                 220

Thr Glu Leu Gly Arg Gly Asp Tyr Trp Gly Gln Gly Thr Ser Val Ala
225                 230                 235                 240

Val Ser Ser


<210> SEQ ID NO 64
<211> LENGTH: 121
<212> TYPE: PRT
<213> ORGANISM: Artificial sequence
<220> FEATURE:
<223> OTHER INFORMATION: LIR1 scFv-2 VL

<400> SEQUENCE: 64

Glu Val Gln Leu Gln Gln Ser Gly Thr Val Leu Pro Arg Pro Gly Ala
1               5                   10                  15
```

Ser Val Lys Met Ser Cys Lys Ala Ser Gly Tyr Ser Phe Thr Asn Tyr
20 25 30

Trp Met His Trp Val Lys Gln Arg Pro Gly Gln Gly Leu Glu Trp Ile
35 40 45

Gly Ala Ile Tyr Pro Gly Asn Ser Asp Thr Ser Tyr Asn Gln Lys Phe
50 55 60

Glu Gly Lys Ala Lys Leu Thr Ala Val Thr Ser Ala Ser Thr Ala Tyr
65 70 75 80

Met Glu Leu Ser Ser Leu Thr Asn Glu Asp Ser Ala Val Tyr Tyr Cys
85 90 95

Thr Thr Tyr Asp Gly Tyr Tyr Ser Ala Trp Phe Ala Tyr Trp Gly Gln
100 105 110

Gly Thr Leu Val Thr Val Ser Ala Ala
115 120

<210> SEQ ID NO 65
<211> LENGTH: 108
<212> TYPE: PRT
<213> ORGANISM: Artificial sequence
<220> FEATURE:
<223> OTHER INFORMATION: LIR1 scFv-2 VH

<400> SEQUENCE: 65

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Thr Gly
50 55 60

Ser Gly Ser Gly Thr Asp Phe Thr Phe Thr Ile Ser Ser Val Gln Ala
65 70 75 80

Glu Asp Leu Ala Leu Tyr Tyr Cys Gln Gln His Tyr Ser Pro Pro Trp
85 90 95

Thr Phe Gly Gly Gly Thr Lys Leu Glu Ile Lys Arg
100 105

<210> SEQ ID NO 66
<211> LENGTH: 244
<212> TYPE: PRT
<213> ORGANISM: Artificial sequence
<220> FEATURE:
<223> OTHER INFORMATION: LIR1 scFv-2

<400> SEQUENCE: 66

Glu Val Gln Leu Gln Gln Ser Gly Thr Val Leu Pro Arg Pro Gly Ala
1 5 10 15

Ser Val Lys Met Ser Cys Lys Ala Ser Gly Tyr Ser Phe Thr Asn Tyr
20 25 30

Trp Met His Trp Val Lys Gln Arg Pro Gly Gln Gly Leu Glu Trp Ile
35 40 45

Gly Ala Ile Tyr Pro Gly Asn Ser Asp Thr Ser Tyr Asn Gln Lys Phe
50 55 60

Glu Gly Lys Ala Lys Leu Thr Ala Val Thr Ser Ala Ser Thr Ala Tyr
65 70 75 80

Met Glu Leu Ser Ser Leu Thr Asn Glu Asp Ser Ala Val Tyr Tyr Cys
85 90 95

Thr Thr Tyr Asp Gly Tyr Tyr Ser Ala Trp Phe Ala Tyr Trp Gly Gln
100 105 110

Gly Thr Leu Val Thr Val Ser Ala Ala Gly Gly Gly Gly Ser Gly Gly
115 120 125

Gly Gly Ser Gly Gly Gly Gly Ser Asp Ile Val Met Thr Gln Ser His
130 135 140

Lys Phe Met Ser Thr Ser Val Gly Asp Arg Val Ser Ile Thr Cys Lys
145 150 155 160

Ala Ser Gln Asp Val Ser Thr Ala Val Ala Trp Tyr Gln Gln Lys Pro
165 170 175

Gly Gln Ser Pro Lys Leu Leu Ile Tyr Ser Ala Ser Tyr Arg Tyr Thr
180 185 190

Gly Val Pro Asp Arg Phe Thr Gly Ser Gly Ser Gly Thr Asp Phe Thr
195 200 205

Phe Thr Ile Ser Ser Val Gln Ala Glu Asp Leu Ala Leu Tyr Tyr Cys
210 215 220

Gln Gln His Tyr Ser Pro Pro Trp Thr Phe Gly Gly Gly Thr Lys Leu
225 230 235 240

Glu Ile Lys Arg

<210> SEQ ID NO 67
<211> LENGTH: 124
<212> TYPE: PRT
<213> ORGANISM: Artificial sequence
<220> FEATURE:
<223> OTHER INFORMATION: NKG2A scFv VH

<400> SEQUENCE: 67

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Arg Ile Asp Pro Tyr Asp Ser Glu Thr His Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Gly Gly Tyr Asp Phe Asp Val Gly Thr Leu Tyr Trp Phe Phe
100 105 110

Asp Val Trp Gly Gln Gly Thr Thr Val Thr Val Ser
115 120

<210> SEQ ID NO 68
<211> LENGTH: 107
<212> TYPE: PRT
<213> ORGANISM: Artificial sequence
<220> FEATURE:
<223> OTHER INFORMATION: NKG2A scFv VL

<400> SEQUENCE: 68

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Tyr
20 25 30

```
Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105


<210> SEQ ID NO 69
<211> LENGTH: 246
<212> TYPE: PRT
<213> ORGANISM: Artificial sequence
<220> FEATURE:
<223> OTHER INFORMATION: NKG2A scFv

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Val Gln
        115                 120                 125

Ser Gly Ala Glu Val Lys Lys Pro Gly Ala Ser Val Lys Val Ser Cys
    130                 135                 140

Lys Ala Ser Gly Tyr Thr Phe Thr Ser Tyr Trp Met Asn Trp Val Arg
145                 150                 155                 160

Gln Ala Pro Gly Gln Gly Leu Glu Trp Met Gly Arg Ile Asp Pro Tyr
                165                 170                 175

Asp Ser Glu Thr His Tyr Ala Gln Lys Leu Gln Gly Arg Val Thr Met
            180                 185                 190

Thr Thr Asp Thr Ser Thr Ser Thr Ala Tyr Met Glu Leu Arg Ser Leu
        195                 200                 205

Arg Ser Asp Asp Thr Ala Val Tyr Tyr Cys Ala Arg Gly Gly Tyr Asp
    210                 215                 220

Phe Asp Val Gly Thr Leu Tyr Trp Phe Phe Asp Val Trp Gly Gln Gly
225                 230                 235                 240

Thr Thr Val Thr Val Ser
                245


<210> SEQ ID NO 70
<211> LENGTH: 223
<212> TYPE: PRT
<213> ORGANISM: Artificial sequence
```

<220> FEATURE:
<223> OTHER INFORMATION: PDL1 extracellular region

<400> SEQUENCE: 70

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu
    210                 215                 220
```

<210> SEQ ID NO 71
<211> LENGTH: 201
<212> TYPE: PRT
<213> ORGANISM: Artificial sequence
<220> FEATURE:
<223> OTHER INFORMATION: PDL2 extracellular region

<400> SEQUENCE: 71

```
Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
```

115 120 125

Tyr Pro Leu Ala Glu Val Ser Trp Pro Asn Val Ser Val Pro Ala Asn
130 135 140

Thr Ser His Ser Arg Thr Pro Glu Gly Leu Tyr Gln Val Thr Ser Val
145 150 155 160

Leu Arg Leu Lys Pro Pro Pro Gly Arg Asn Phe Ser Cys Val Phe Trp
165 170 175

Asn Thr His Val Arg Glu Leu Thr Leu Ala Ser Ile Asp Leu Gln Ser
180 185 190

Gln Met Glu Pro Arg Thr His Pro Thr
195 200

<210> SEQ ID NO 72
<211> LENGTH: 11
<212> TYPE: PRT
<213> ORGANISM: Artificial Sequence
<220> FEATURE:
<223> OTHER INFORMATION: NKG2A scFv CDR-L1

<400> SEQUENCE: 72

Ser Ala Ser Ser Ser Val Ser Ser Tyr Ile Tyr
1 5 10

<210> SEQ ID NO 73
<211> LENGTH: 7
<212> TYPE: PRT
<213> ORGANISM: Artificial Sequence
<220> FEATURE:
<223> OTHER INFORMATION: NKG2A scFv CDR-L2

<400> SEQUENCE: 73

Leu Thr Ser Asn Leu Ala Ser
5

<210> SEQ ID NO 74
<211> LENGTH: 9
<212> TYPE: PRT
<213> ORGANISM: Artificial Sequence
<220> FEATURE:
<223> OTHER INFORMATION: NKG2A scFv CDR-L3

<400> SEQUENCE: 74

Gln Gln Trp Ser Gly Asn Pro Tyr Thr
1 5

<210> SEQ ID NO 75
<211> LENGTH: 7
<212> TYPE: PRT
<213> ORGANISM: Artificial Sequence
<220> FEATURE:
<223> OTHER INFORMATION: NKG2A scFv CDR-H1

<400> SEQUENCE: 75

Gly Phe Thr Phe Ser Ser Tyr
5

<210> SEQ ID NO 76
<211> LENGTH: 6
<212> TYPE: PRT
<213> ORGANISM: Artificial Sequence
<220> FEATURE:
<223> OTHER INFORMATION: NKG2A scFv CDR-H2

<400> SEQUENCE: 76

Ser Ser Gly Gly Ser Tyr
5

<210> SEQ ID NO 77
<211> LENGTH: 10
<212> TYPE: PRT
<213> ORGANISM: Artificial Sequence
<220> FEATURE:
<223> OTHER INFORMATION: NKG2A scFv CDR-H3

<400> SEQUENCE: 77

His Gly Asp Tyr Pro Arg Phe Phe Asp Val
1 5 10

<210> SEQ ID NO 78
<211> LENGTH: 11
<212> TYPE: PRT
<213> ORGANISM: Artificial Sequence
<220> FEATURE:
<223> OTHER INFORMATION: NKG2A scFv CDR-L1

<400> SEQUENCE: 78

Arg Ala Ser Glu Asn Ile Tyr Ser Tyr Leu Ala
1 5 10

<210> SEQ ID NO 79
<211> LENGTH: 7
<212> TYPE: PRT
<213> ORGANISM: Artificial Sequence
<220> FEATURE:
<223> OTHER INFORMATION: NKG2A scFv CDR-L2

<400> SEQUENCE: 79

Asn Ala Lys Thr Leu Ala Glu
5

<210> SEQ ID NO 80
<211> LENGTH: 9
<212> TYPE: PRT
<213> ORGANISM: Artificial Sequence
<220> FEATURE:
<223> OTHER INFORMATION: NKG2A scFv CDR-L3

<400> SEQUENCE: 80

Gln His His Tyr Gly Thr Pro Arg Thr
1 5

<210> SEQ ID NO 81
<211> LENGTH: 7
<212> TYPE: PRT
<213> ORGANISM: Artificial Sequence
<220> FEATURE:
<223> OTHER INFORMATION: NKG2A scFv CDR-H1

<400> SEQUENCE: 81

Gly Tyr Thr Phe Thr Ser Tyr
5

<210> SEQ ID NO 82
<211> LENGTH: 6
<212> TYPE: PRT
<213> ORGANISM: Artificial Sequence
<220> FEATURE:
<223> OTHER INFORMATION: NKG2A scFv CDR-H2

<400> SEQUENCE: 82

Asp Pro Tyr Asp Ser Glu

5

<210> SEQ ID NO 83
<211> LENGTH: 16
<212> TYPE: PRT
<213> ORGANISM: Artificial Sequence
<220> FEATURE:
<223> OTHER INFORMATION: NKG2A scFv CDR-H3

<400> SEQUENCE: 83

Gly Gly Tyr Asp Phe Asp Val Gly Thr Leu Tyr Trp Phe Phe Asp Val
1 5 10 15

<210> SEQ ID NO 84
<211> LENGTH: 11
<212> TYPE: PRT
<213> ORGANISM: Artificial Sequence
<220> FEATURE:
<223> OTHER INFORMATION: KIR scFv CDR-L1

<400> SEQUENCE: 84

Arg Ala Ser Gln Ser Val Ser Ser Tyr Leu Ala
1 5 10

<210> SEQ ID NO 85
<211> LENGTH: 7
<212> TYPE: PRT
<213> ORGANISM: Artificial Sequence
<220> FEATURE:
<223> OTHER INFORMATION: KIR scFv CDR-L2

<400> SEQUENCE: 85

Asp Ala Ser Asn Arg Ala Thr
5

<210> SEQ ID NO 86
<211> LENGTH: 9
<212> TYPE: PRT
<213> ORGANISM: Artificial Sequence
<220> FEATURE:
<223> OTHER INFORMATION: KIR scFv CDR-L3

<400> SEQUENCE: 86

Gln Gln Arg Ser Asn Trp Met Tyr Thr
1 5

<210> SEQ ID NO 87
<211> LENGTH: 7
<212> TYPE: PRT
<213> ORGANISM: Artificial Sequence
<220> FEATURE:
<223> OTHER INFORMATION: KIR scFv CDR-H1

<400> SEQUENCE: 87

Gly Gly Thr Phe Ser Phe Tyr
5

<210> SEQ ID NO 88
<211> LENGTH: 6
<212> TYPE: PRT
<213> ORGANISM: Artificial Sequence
<220> FEATURE:
<223> OTHER INFORMATION: KIR scFv CDR-H2

<400> SEQUENCE: 88

Ile Pro Ile Phe Gly Ala
1 5

<210> SEQ ID NO 89
<211> LENGTH: 14
<212> TYPE: PRT
<213> ORGANISM: Artificial Sequence
<220> FEATURE:
<223> OTHER INFORMATION: KIR scFv CDR-H3

<400> SEQUENCE: 89

Ile Pro Ser Gly Ser Tyr Tyr Tyr Asp Tyr Asp Met Asp Val
1 5 10

<210> SEQ ID NO 90
<211> LENGTH: 11
<212> TYPE: PRT
<213> ORGANISM: Artificial Sequence
<220> FEATURE:
<223> OTHER INFORMATION: LIR1 scFv-1 CDR-L1

<400> SEQUENCE: 90

Arg Ala Ser Gln Ser Ile Gly Thr Asn Ile His
1 5 10

<210> SEQ ID NO 91
<211> LENGTH: 7
<212> TYPE: PRT
<213> ORGANISM: Artificial Sequence
<220> FEATURE:
<223> OTHER INFORMATION: LIR1 scFv-1 CDR-L2

<400> SEQUENCE: 91

Tyr Ala Ser Glu Ser Ile Ser
5

<210> SEQ ID NO 92
<211> LENGTH: 9
<212> TYPE: PRT
<213> ORGANISM: Artificial Sequence
<220> FEATURE:
<223> OTHER INFORMATION: LIR1 scFv-1 CDR-L3

<400> SEQUENCE: 92

Gln Gln Ser Tyr Ser Trp Pro Tyr Thr
1 5

<210> SEQ ID NO 93
<211> LENGTH: 9
<212> TYPE: PRT
<213> ORGANISM: Artificial Sequence
<220> FEATURE:
<223> OTHER INFORMATION: LIR1 scFv-1 CDR-H1

<400> SEQUENCE: 93

Gly Phe Ser Leu Ser Thr Ser Gly Leu
5

<210> SEQ ID NO 94
<211> LENGTH: 5
<212> TYPE: PRT
<213> ORGANISM: Artificial Sequence
<220> FEATURE:
<223> OTHER INFORMATION: LIR1 scFv-1 CDR-H2

<400> SEQUENCE: 94

Trp Trp Asp Asp Asp
5

<210> SEQ ID NO 95
<211> LENGTH: 8
<212> TYPE: PRT
<213> ORGANISM: Artificial Sequence
<220> FEATURE:
<223> OTHER INFORMATION: LIR1 scFv-1 CDR-H3

<400> SEQUENCE: 95

Thr Glu Leu Gly Arg Gly Asp Tyr
1               5

<210> SEQ ID NO 96
<211> LENGTH: 7
<212> TYPE: PRT
<213> ORGANISM: Artificial Sequence
<220> FEATURE:
<223> OTHER INFORMATION: LIR1 scFv-2 CDR-L1

<400> SEQUENCE: 96

Gly Tyr Ser Phe Thr Asn Tyr
1               5

<210> SEQ ID NO 97
<211> LENGTH: 6
<212> TYPE: PRT
<213> ORGANISM: Artificial Sequence
<220> FEATURE:
<223> OTHER INFORMATION: LIR1 scFv-2 CDR-L2

<400> SEQUENCE: 97

Tyr Pro Gly Asn Ser Asp
                5

<210> SEQ ID NO 98
<211> LENGTH: 11
<212> TYPE: PRT
<213> ORGANISM: Artificial Sequence
<220> FEATURE:
<223> OTHER INFORMATION: LIR1 scFv-2 CDR-L3

<400> SEQUENCE: 98

Tyr Asp Gly Tyr Tyr Ser Ala Trp Phe Ala Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: LIR1 scFv-2 CDR-H1

<400> SEQUENCE: 99

Lys Ala Ser Gln Asp Val Ser Thr Ala Val Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: LIR1 scFv-2 CDR-H2

<400> SEQUENCE: 100

Ser Ala Ser Tyr Arg Tyr Thr
                5

<210> SEQ ID NO 101
<211> LENGTH: 9
<212> TYPE: PRT
<213> ORGANISM: Artificial Sequence
<220> FEATURE:
<223> OTHER INFORMATION: LIR1 scFv-2 CDR-H3

<400> SEQUENCE: 101

```
Gln Gln His Tyr Ser Pro Pro Trp Thr
                5
```

<210> SEQ ID NO 102
<211> LENGTH: 15
<212> TYPE: PRT
<213> ORGANISM: Artificial Sequence
<220> FEATURE:
<223> OTHER INFORMATION: SIGLEC7 scFv-1 CDR-L1

<400> SEQUENCE: 102

```
Arg Ala Ser Gln Ser Val Ser Thr Ser Ser His Ser Tyr Leu His
1               5                   10                  15
```

<210> SEQ ID NO 103
<211> LENGTH: 7
<212> TYPE: PRT
<213> ORGANISM: Artificial Sequence
<220> FEATURE:
<223> OTHER INFORMATION: SIGLEC7 scFv-1 CDR-L2

<400> SEQUENCE: 103

```
Tyr Ala Ser Asn Leu Ala Ser
                5
```

<210> SEQ ID NO 104
<211> LENGTH: 9
<212> TYPE: PRT
<213> ORGANISM: Artificial Sequence
<220> FEATURE:
<223> OTHER INFORMATION: SIGLEC7 scFv-1 CDR-L3

<400> SEQUENCE: 104

```
Gln His Ser Trp Glu Ile Pro Tyr Thr
1               5
```

<210> SEQ ID NO 105
<211> LENGTH: 7
<212> TYPE: PRT
<213> ORGANISM: Artificial Sequence
<220> FEATURE:
<223> OTHER INFORMATION: SIGLEC7 scFv-1 CDR-H1

<400> SEQUENCE: 105

```
Gly Phe Asn Phe Lys Asp Thr
1               5
```

<210> SEQ ID NO 106
<211> LENGTH: 6
<212> TYPE: PRT
<213> ORGANISM: Artificial Sequence
<220> FEATURE:
<223> OTHER INFORMATION: SIGLEC7 scFv-1 CDR-H2

<400> SEQUENCE: 106

```
Asp Pro Ala Asn Gly Asn
                5
```

<210> SEQ ID NO 107

<211> LENGTH: 9
<212> TYPE: PRT
<213> ORGANISM: Artificial Sequence
<220> FEATURE:
<223> OTHER INFORMATION: SIGLEC7 scFv-1 CDR-H3

<400> SEQUENCE: 107

```
Gly Trp Asp Gly Tyr Tyr Phe Asp Cys
                5
```

<210> SEQ ID NO 108
<211> LENGTH: 111
<212> TYPE: PRT
<213> ORGANISM: Artificial Sequence
<220> FEATURE:
<223> OTHER INFORMATION: SIGLEC7 scFv-1 VL

<400> SEQUENCE: 108

```
Asp Ile Val Leu Thr Gln Ser Pro Ala Ser Leu Val Val Ser Leu Gly
1               5                   10                  15

Leu Arg Ala Thr Ile Ser Cys Arg Ala Ser Gln Ser Val Ser Thr Ser
            20                  25                  30

Ser His Ser Tyr Leu His Trp Tyr Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Ala Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

<210> SEQ ID NO 109
<211> LENGTH: 118
<212> TYPE: PRT
<213> ORGANISM: Artificial Sequence
<220> FEATURE:
<223> OTHER INFORMATION: SIGLEC7 scFv-1 VH

<400> SEQUENCE: 109

```
Glu Val Gln Leu Gln Gln Ser Gly Ala Glu Leu Val Lys Pro Gly Ala
1               5                   10                  15

Ser Val Lys Leu Ser Cys Thr Val Ser Gly Phe Asn Phe Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Ser Lys Phe
    50                  55                  60

Gln Asp Lys Ala Thr Ile Thr Ala Asp Thr Ser Ser Asn Thr Val Tyr
65                  70                  75                  80

Met Gln Leu Ser Ser Leu Thr Ser Glu Asp Thr Ala Val Tyr Tyr Cys
                85                  90                  95

Thr Arg Gly Trp Asp Gly Tyr Tyr Phe Asp Cys Trp Gly Gln Gly Thr
            100                 105                 110

Thr Leu Thr Val Ser Ser
        115
```

<210> SEQ ID NO 110
<211> LENGTH: 244

<212> TYPE: PRT
<213> ORGANISM: Artificial Sequence
<220> FEATURE:
<223> OTHER INFORMATION: SIGLEC7 scFv-1

<400> SEQUENCE: 110

Asp Ile Val Leu Thr Gln Ser Pro Ala Ser Leu Val Val Ser Leu Gly
1 5 10 15

Leu Arg Ala Thr Ile Ser Cys Arg Ala Ser Gln Ser Val Ser Thr Ser
20 25 30

Ser His Ser Tyr Leu His Trp Tyr Gln Gln Lys Pro Gly Gln Pro Pro
35 40 45

Lys Leu Leu Ile Lys Tyr Ala Ser Asn Leu Ala Ser Gly Val Pro Ala
50 55 60

Arg Phe Ser Gly Ser Gly Ser Gly Ala Asp Phe Thr Leu Asn Ile His
65 70 75 80

Pro Val Glu Glu Glu Asp Thr Ala Thr Tyr Tyr Cys Gln His Ser Trp
85 90 95

Glu Ile Pro Tyr Thr Phe Gly Gly Gly Thr Lys Leu Glu Ile Lys Gly
100 105 110

Gly Gly Gly Ser Gly Gly Gly Gly Ser Gly Gly Gly Gly Ser Glu Val
115 120 125

Gln Leu Gln Gln Ser Gly Ala Glu Leu Val Lys Pro Gly Ala Ser Val
130 135 140

Lys Leu Ser Cys Thr Val Ser Gly Phe Asn Phe Lys Asp Thr Tyr Ile
145 150 155 160

His Trp Val Lys Gln Arg Pro Glu Gln Gly Leu Glu Trp Ile Gly Arg
165 170 175

Ile Asp Pro Ala Asn Gly Asn Thr Lys Tyr Ala Ser Lys Phe Gln Asp
180 185 190

Lys Ala Thr Ile Thr Ala Asp Thr Ser Ser Asn Thr Val Tyr Met Gln
195 200 205

Leu Ser Ser Leu Thr Ser Glu Asp Thr Ala Val Tyr Tyr Cys Thr Arg
210 215 220

Gly Trp Asp Gly Tyr Tyr Phe Asp Cys Trp Gly Gln Gly Thr Thr Leu
225 230 235 240

Thr Val Ser Ser

<210> SEQ ID NO 111
<211> LENGTH: 12
<212> TYPE: PRT
<213> ORGANISM: Artificial Sequence
<220> FEATURE:
<223> OTHER INFORMATION: KLRG1 scFv-1 CDR-L1

<400> SEQUENCE: 111

Arg Ala Ser Ser Ser Val Ser Ser Asn Tyr Leu His
1 5 10

<210> SEQ ID NO 112
<211> LENGTH: 7
<212> TYPE: PRT
<213> ORGANISM: Artificial Sequence
<220> FEATURE:
<223> OTHER INFORMATION: KLRG1 scFv-1 CDR-L2

<400> SEQUENCE: 112

Ser Thr Ser Asn Leu Ala Ser
5

<210> SEQ ID NO 113
<211> LENGTH: 9
<212> TYPE: PRT
<213> ORGANISM: Artificial Sequence
<220> FEATURE:
<223> OTHER INFORMATION: KLRG1 scFv-1 CDR-L3

<400> SEQUENCE: 113

Gln Gln Tyr Ser Gly Tyr Pro Leu Thr
1 5

<210> SEQ ID NO 114
<211> LENGTH: 7
<212> TYPE: PRT
<213> ORGANISM: Artificial Sequence
<220> FEATURE:
<223> OTHER INFORMATION: KLRG1 scFv-1 CDR-H1

<400> SEQUENCE: 114

Gly Tyr Thr Phe Thr Ser Tyr
1 5

<210> SEQ ID NO 115
<211> LENGTH: 6
<212> TYPE: PRT
<213> ORGANISM: Artificial Sequence
<220> FEATURE:
<223> OTHER INFORMATION: KLRG1 scFv-1 CDR-H2

<400> SEQUENCE: 115

Tyr Pro Gly Arg Ser Asn
5

<210> SEQ ID NO 116
<211> LENGTH: 9
<212> TYPE: PRT
<213> ORGANISM: Artificial Sequence
<220> FEATURE:
<223> OTHER INFORMATION: KLRG1 scFv-1 CDR-H3

<400> SEQUENCE: 116

Asp Ala Thr Val Glu Pro Leu Pro Tyr
5

<210> SEQ ID NO 117
<211> LENGTH: 108
<212> TYPE: PRT
<213> ORGANISM: Artificial Sequence
<220> FEATURE:
<223> OTHER INFORMATION: KLRG1 scFv-1 VL

<400> SEQUENCE: 117

Glu Asn Val Leu Thr Gln Ser Pro Ala Ile Met Ser Ala Ser Pro Gly
1 5 10 15

Glu Lys Val Thr Met Thr Cys Arg Ala Ser Ser Ser Val Ser Ser Asn
20 25 30

Tyr Leu His Trp Tyr Gln Gln Lys Ser Gly Ala Ser Pro Lys Ile Trp
35 40 45

Ile Tyr Ser Thr Ser Asn Leu Ala Ser Ala Val Pro Ala Arg Phe Ser
50 55 60

Gly Ser Gly Ser Gly Thr Ser Tyr Ser Leu Thr Ile Ser Ser Val Glu
65 70 75 80

Ala Glu Asp Ala Ala Thr Tyr Tyr Cys Gln Gln Tyr Ser Gly Tyr Pro 85 90 95

Leu Thr Phe Gly Gly Gly Thr Lys Leu Glu Ile Lys
100 105

<210> SEQ ID NO 118
<211> LENGTH: 118
<212> TYPE: PRT
<213> ORGANISM: Artificial Sequence
<220> FEATURE:
<223> OTHER INFORMATION: KLRG1 scFv-1 VH

<400> SEQUENCE: 118

Gln Val Gln Leu Gln Gln Pro Gly Ala Glu Phe Val Lys Pro Gly Ala
1 5 10 15

Ser Val Lys Leu Ser Cys Lys Ala Ser Gly Tyr Thr Phe Thr Ser Tyr
20 25 30

Trp Ile His Trp Met Lys Gln Arg Pro Gly Gln Gly Leu Glu Trp Ile
35 40 45

Gly Asn Ile Tyr Pro Gly Arg Ser Asn Asn Asn Tyr Asn Glu Lys Phe
50 55 60

Lys Asn Arg Ala Thr Leu Thr Val Asp Thr Ser Ser Ser Thr Ala Tyr
65 70 75 80

Met Gln Phe Arg Ser Leu Thr Ser Asp Asp Ser Ala Val Tyr Tyr Cys
85 90 95

Ala Arg Asp Ala Thr Val Glu Pro Leu Pro Tyr Trp Gly Gln Gly Thr
100 105 110

Leu Val Thr Val Ser Ala
115

<210> SEQ ID NO 119
<211> LENGTH: 241
<212> TYPE: PRT
<213> ORGANISM: Artificial Sequence
<220> FEATURE:
<223> OTHER INFORMATION: KLRG1 scFv-1

<400> SEQUENCE: 119

Gln Val Gln Leu Gln Gln Pro Gly Ala Glu Phe Val Lys Pro Gly Ala
1 5 10 15

Ser Val Lys Leu Ser Cys Lys Ala Ser Gly Tyr Thr Phe Thr Ser Tyr
20 25 30

Trp Ile His Trp Met Lys Gln Arg Pro Gly Gln Gly Leu Glu Trp Ile
35 40 45

Gly Asn Ile Tyr Pro Gly Arg Ser Asn Asn Asn Tyr Asn Glu Lys Phe
50 55 60

Lys Asn Arg Ala Thr Leu Thr Val Asp Thr Ser Ser Ser Thr Ala Tyr
65 70 75 80

Met Gln Phe Arg Ser Leu Thr Ser Asp Asp Ser Ala Val Tyr Tyr Cys
85 90 95

Ala Arg Asp Ala Thr Val Glu Pro Leu Pro Tyr Trp Gly Gln Gly Thr
100 105 110

Leu Val Thr Val Ser Ala Gly Gly Gly Gly Ser Gly Gly Gly Gly Ser
115 120 125

Gly Gly Gly Gly Ser Glu Asn Val Leu Thr Gln Ser Pro Ala Ile Met
130 135 140

Ser Ala Ser Pro Gly Glu Lys Val Thr Met Thr Cys Arg Ala Ser Ser
145 150 155 160

Ser Val Ser Ser Asn Tyr Leu His Trp Tyr Gln Gln Lys Ser Gly Ala
165 170 175

Ser Pro Lys Ile Trp Ile Tyr Ser Thr Ser Asn Leu Ala Ser Ala Val
180 185 190

Pro Ala Arg Phe Ser Gly Ser Gly Ser Gly Thr Ser Tyr Ser Leu Thr
195 200 205

Ile Ser Ser Val Glu Ala Glu Asp Ala Ala Thr Tyr Tyr Cys Gln Gln
210 215 220

Tyr Ser Gly Tyr Pro Leu Thr Phe Gly Gly Gly Thr Lys Leu Glu Ile
225 230 235 240

Lys

<210> SEQ ID NO 120
<211> LENGTH: 20
<212> TYPE: PRT
<213> ORGANISM: Artificial Sequence
<220> FEATURE:
<223> OTHER INFORMATION: PDL1 transmembrane domain

<400> SEQUENCE: 120

Val Ile Leu Gly Ala Ile Leu Leu Cys Leu Gly Val Ala Leu Thr Phe
1 5 10 15

Ile Phe Arg Leu
20

<210> SEQ ID NO 121
<211> LENGTH: 18
<212> TYPE: PRT
<213> ORGANISM: Artificial Sequence
<220> FEATURE:
<223> OTHER INFORMATION: PDL1 signal peptide

<400> SEQUENCE: 121

Met Arg Ile Phe Ala Val Phe Ile Phe Met Thr Tyr Trp His Leu Leu
1 5 10 15

Asn Ala

<210> SEQ ID NO 122
<211> LENGTH: 11
<212> TYPE: PRT
<213> ORGANISM: Artificial Sequence
<220> FEATURE:
<223> OTHER INFORMATION: SIGLEC7 scFv-2 CDR-L1

<400> SEQUENCE: 122

Ser Ala Ser Gln Gly Ile Thr Asn Tyr Leu Asn
1 5 10

<210> SEQ ID NO 123
<211> LENGTH: 7
<212> TYPE: PRT
<213> ORGANISM: Artificial Sequence
<220> FEATURE:
<223> OTHER INFORMATION: SIGLEC7 scFv-2 CDR-L2

<400> SEQUENCE: 123

Tyr Thr Ser Ile Leu His Ser
5

<210> SEQ ID NO 124
<211> LENGTH: 9
<212> TYPE: PRT
<213> ORGANISM: Artificial Sequence
<220> FEATURE:
<223> OTHER INFORMATION: SIGLEC7 scFv-2 CDR-L3

<400> SEQUENCE: 124

Gln Gln Tyr Ser Lys Pro Pro Tyr Thr
1               5

<210> SEQ ID NO 125
<211> LENGTH: 7
<212> TYPE: PRT
<213> ORGANISM: Artificial Sequence
<220> FEATURE:
<223> OTHER INFORMATION: SIGLEC7 scFv-2 CDR-H1

<400> SEQUENCE: 125

Gly Phe Thr Phe Ser Asn Tyr
1               5

<210> SEQ ID NO 126
<211> LENGTH: 8
<212> TYPE: PRT
<213> ORGANISM: Artificial Sequence
<220> FEATURE:
<223> OTHER INFORMATION: SIGLEC7 scFv-2 CDR-H2

<400> SEQUENCE: 126

Arg Leu Lys Ser Asp Asn Tyr Ala
                5

<210> SEQ ID NO 127
<211> LENGTH: 8
<212> TYPE: PRT
<213> ORGANISM: Artificial Sequence
<220> FEATURE:
<223> OTHER INFORMATION: SIGLEC7 scFv-2 CDR-H3

<400> SEQUENCE: 127

Gly Asp Tyr Asp Ile Phe Ala Tyr
                5

<210> SEQ ID NO 128
<211> LENGTH: 107
<212> TYPE: PRT
<213> ORGANISM: Artificial Sequence
<220> FEATURE:
<223> OTHER INFORMATION: SIGLEC7 scFv-2 VL

<400> SEQUENCE: 128

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Pro Pro Tyr
                85                  90                  95

Thr Phe Gly Gly Gly Thr Lys Leu Glu Ile Lys
            100                 105

```
<210> SEQ ID NO 129
<211> LENGTH: 119
<212> TYPE: PRT
<213> ORGANISM: Artificial Sequence
<220> FEATURE:
<223> OTHER INFORMATION: SIGLEC7 scFv-2 VH

<400> SEQUENCE: 129

Glu Val Lys Leu Glu Glu Ser Gly Gly Gly Leu Val Gln Pro Gly Gly
1               5                   10                  15

Ser Met Lys Val Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Glu Gly Asp Tyr Asp Ile Phe Ala Tyr Trp Gly Gln Gly
            100                 105                 110

Thr Leu Val Thr Val Ser Ala
        115


<210> SEQ ID NO 130
<211> LENGTH: 241
<212> TYPE: PRT
<213> ORGANISM: Artificial Sequence
<220> FEATURE:
<223> OTHER INFORMATION: SIGLEC7 scFv-2

<400> SEQUENCE: 130

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Pro Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Glu Val Lys Leu Glu Glu
        115                 120                 125

Ser Gly Gly Gly Leu Val Gln Pro Gly Gly Ser Met Lys Val Ser Cys
    130                 135                 140

Val Ala Ser Gly Phe Thr Phe Ser Asn Tyr Trp Met Asn Trp Val Arg
145                 150                 155                 160

Gln Ser Pro Glu Lys Gly Leu Glu Trp Val Ala Gln Ile Arg Leu Lys
                165                 170                 175

Ser Asp Asn Tyr Ala Thr His Tyr Ala Glu Ser Val Lys Gly Arg Phe
            180                 185                 190
```

Thr Ile Ser Arg Asp Asp Ser Lys Ser Ser Val Tyr Leu Gln Met Asn
195 200 205

Asn Leu Arg Ala Glu Asp Thr Gly Ile Tyr Tyr Cys Thr Glu Gly Asp
210 215 220

Tyr Asp Ile Phe Ala Tyr Trp Gly Gln Gly Thr Leu Val Thr Val Ser
225 230 235 240

Ala

<210> SEQ ID NO 131
<211> LENGTH: 15
<212> TYPE: PRT
<213> ORGANISM: Artificial Sequence
<220> FEATURE:
<223> OTHER INFORMATION: SIGLEC7 scFv-3 CDR-L1

<400> SEQUENCE: 131

Arg Ala Ser Gln Ser Val Ser Ser Ser Ser Tyr Ser Tyr Met His
1 5 10 15

<210> SEQ ID NO 132
<211> LENGTH: 7
<212> TYPE: PRT
<213> ORGANISM: Artificial Sequence
<220> FEATURE:
<223> OTHER INFORMATION: SIGLEC7 scFv-3 CDR-L2

<400> SEQUENCE: 132

Tyr Ala Ser Asn Leu Lys Ser
5

<210> SEQ ID NO 133
<211> LENGTH: 9
<212> TYPE: PRT
<213> ORGANISM: Artificial Sequence
<220> FEATURE:
<223> OTHER INFORMATION: SIGLEC7 scFv-3 CDR-L3

<400> SEQUENCE: 133

Gln His Ser Trp Glu Ile Pro Pro Thr
1 5

<210> SEQ ID NO 134
<211> LENGTH: 9
<212> TYPE: PRT
<213> ORGANISM: Artificial Sequence
<220> FEATURE:
<223> OTHER INFORMATION: SIGLEC7 scFv-3 CDR-H1

<400> SEQUENCE: 134

Gly Phe Ser Leu Ser Thr Phe Gly Met
1 5

<210> SEQ ID NO 135
<211> LENGTH: 5
<212> TYPE: PRT
<213> ORGANISM: Artificial Sequence
<220> FEATURE:
<223> OTHER INFORMATION: SIGLEC7 scFv-3 CDR-H2

<400> SEQUENCE: 135

Trp Trp Asp Asp Asp
5

<210> SEQ ID NO 136
<211> LENGTH: 9

<212> TYPE: PRT
<213> ORGANISM: Artificial Sequence
<220> FEATURE:
<223> OTHER INFORMATION: SIGLEC7 scFv-3 CDR-H3

<400> SEQUENCE: 136

Val Glu Arg Gly Tyr Pro Leu Asp His
5

<210> SEQ ID NO 137
<211> LENGTH: 111
<212> TYPE: PRT
<213> ORGANISM: Artificial Sequence
<220> FEATURE:
<223> OTHER INFORMATION: SIGLEC7 scFv-3 VL

<400> SEQUENCE: 137

Asp Ile Val Leu Thr Gln Ser Pro Ala Ser Leu Ala Val Ser Leu Gly
1 5 10 15

Gln Arg Ala Thr Ile Ser Cys Arg Ala Ser Gln Ser Val Ser Ser Ser
20 25 30

Ser Tyr Ser Tyr Met His Trp Tyr Gln Gln Lys Pro Gly Gln Pro Pro
35 40 45

Lys Leu Leu Ile Lys Tyr Ala Ser Asn Leu Lys Ser Gly Val Pro Ala
50 55 60

Arg Phe Ser Gly Ser Gly Ser Gly Thr Asp Phe Thr Leu Thr Ile His
65 70 75 80

Pro Val Glu Glu Glu Asp Thr Ala Thr Tyr Tyr Cys Gln His Ser Trp
85 90 95

Glu Ile Pro Pro Thr Phe Gly Gly Gly Thr Lys Leu Glu Ile Lys
100 105 110

<210> SEQ ID NO 138
<211> LENGTH: 119
<212> TYPE: PRT
<213> ORGANISM: Artificial Sequence
<220> FEATURE:
<223> OTHER INFORMATION: SIGLEC7 scFv-3 VH

<400> SEQUENCE: 138

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Phe
20 25 30

Gly Met Gly Val Gly Trp Ile Arg Gln Pro Ser Gly Lys Gly Leu Glu
35 40 45

Trp Leu Ala His Ile Trp Trp Asp Asp Asp Lys Tyr Tyr His Pro Ala
50 55 60

Leu Lys Ser Arg Leu Thr Ile Ser Lys Asp Thr Ser Asn Asn Gln Val
65 70 75 80

Phe Leu Lys Ile Ala Asn Val Asp Thr Ala Glu Thr Ala Thr Phe Tyr
85 90 95

Cys Ala Arg Val Glu Arg Gly Tyr Pro Leu Asp His Trp Gly Gln Gly
100 105 110

Thr Thr Leu Arg Val Ser Ser
115

<210> SEQ ID NO 139
<211> LENGTH: 245
<212> TYPE: PRT

<213> ORGANISM: Artificial Sequence
<220> FEATURE:
<223> OTHER INFORMATION: SIGLEC7 scFv-3

<400> SEQUENCE: 139

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Ser Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Lys Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Glu Glu Asp Thr Ala Thr Tyr Tyr Cys Gln His Ser Trp
                85                  90                  95

Glu Ile Pro Pro Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Thr Leu Lys Glu Ser Gly Pro Gly Ile Leu Gln Pro Ser Gln Thr Leu
    130                 135                 140

Ser Leu Thr Cys Ser Phe Ser Gly Phe Ser Leu Ser Thr Phe Gly Met
145                 150                 155                 160

Gly Val Gly Trp Ile Arg Gln Pro Ser Gly Lys Gly Leu Glu Trp Leu
                165                 170                 175

Ala His Ile Trp Trp Asp Asp Asp Lys Tyr Tyr His Pro Ala Leu Lys
            180                 185                 190

Ser Arg Leu Thr Ile Ser Lys Asp Thr Ser Asn Asn Gln Val Phe Leu
        195                 200                 205

Lys Ile Ala Asn Val Asp Thr Ala Glu Thr Ala Thr Phe Tyr Cys Ala
    210                 215                 220

Arg Val Glu Arg Gly Tyr Pro Leu Asp His Trp Gly Gln Gly Thr Thr
225                 230                 235                 240

Leu Arg Val Ser Ser
                245
```

<210> SEQ ID NO 140
<211> LENGTH: 10
<212> TYPE: PRT
<213> ORGANISM: Artificial Sequence
<220> FEATURE:
<223> OTHER INFORMATION: SIGLEC7 scFv-4 CDR-L1

<400> SEQUENCE: 140

```
Ala Ser Gln Asp Val Ser Thr Ala Val Ala
1               5                   10
```

<210> SEQ ID NO 141
<211> LENGTH: 7
<212> TYPE: PRT
<213> ORGANISM: Artificial Sequence
<220> FEATURE:
<223> OTHER INFORMATION: SIGLEC7 scFv-4 CDR-L2

<400> SEQUENCE: 141

```
Trp Thr Ser Thr Arg His Thr
                5
```

<210> SEQ ID NO 142
<211> LENGTH: 9
<212> TYPE: PRT
<213> ORGANISM: Artificial Sequence
<220> FEATURE:
<223> OTHER INFORMATION: SIGLEC7 scFv-4 CDR-L3

<400> SEQUENCE: 142

His Gln Gln Tyr Ser Thr Pro Pro Thr
1 5

<210> SEQ ID NO 143
<211> LENGTH: 7
<212> TYPE: PRT
<213> ORGANISM: Artificial Sequence
<220> FEATURE:
<223> OTHER INFORMATION: SIGLEC7 scFv-4 CDR-H1

<400> SEQUENCE: 143

Gly Tyr Thr Phe Thr Ser Tyr
1 5

<210> SEQ ID NO 144
<211> LENGTH: 6
<212> TYPE: PRT
<213> ORGANISM: Artificial Sequence
<220> FEATURE:
<223> OTHER INFORMATION: SIGLEC7 scFv-4 CDR-H2

<400> SEQUENCE: 144

Asp Pro Ser Val Ser Tyr
5

<210> SEQ ID NO 145
<211> LENGTH: 10
<212> TYPE: PRT
<213> ORGANISM: Artificial Sequence
<220> FEATURE:
<223> OTHER INFORMATION: SIGLEC7 scFv-4 CDR-H3

<400> SEQUENCE: 145

Trp Ser Lys Asp Tyr Tyr Gly Met Asp Tyr
1 5 10

<210> SEQ ID NO 146
<211> LENGTH: 107
<212> TYPE: PRT
<213> ORGANISM: Artificial Sequence
<220> FEATURE:
<223> OTHER INFORMATION: SIGLEC7 scFv-4 VL

<400> SEQUENCE: 146

Asp Ile Val Leu Thr Gln Ser His Lys Phe Met Ser Thr Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Gln Ser Pro Lys Leu Leu Ile
35 40 45

Tyr Trp Thr Ser Thr Arg His Thr Gly Val Pro Asp Arg Phe Thr Gly
50 55 60

Ser Gly Ser Gly Thr Asp His Thr Leu Thr Ile Ser Ser Val Gln Ala
65 70 75 80

Glu Asp Leu Ala Leu Tyr Tyr Cys His Gln Gln Tyr Ser Thr Pro Pro

```
                85                  90                  95

Thr Phe Gly Gly Gly Thr Lys Leu Glu Ile Lys
            100                 105


<210> SEQ ID NO 147
<211> LENGTH: 119
<212> TYPE: PRT
<213> ORGANISM: Artificial Sequence
<220> FEATURE:
<223> OTHER INFORMATION: SIGLEC7 scFv-4 VH

<400> SEQUENCE: 147

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Val Ser Tyr Thr Glu Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Ser Lys Asp Tyr Tyr Gly Met Asp Tyr Trp Gly Gln Gly
            100                 105                 110

Thr Ser Val Thr Val Ser Ser
        115


<210> SEQ ID NO 148
<211> LENGTH: 241
<212> TYPE: PRT
<213> ORGANISM: Artificial Sequence
<220> FEATURE:
<223> OTHER INFORMATION: SIGLEC7 scFv-4

<400> SEQUENCE: 148

Asp Ile Val Leu Thr Gln Ser His Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp His Thr Leu Thr Ile Ser Ser Val Gln Ala
65                  70                  75                  80

Glu Asp Leu Ala Leu Tyr Tyr Cys His Gln Gln Tyr Ser Thr Pro Pro
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Gln
        115                 120                 125

Pro Gly Ala Glu Leu Val Lys Pro Gly Ala Ser Val Lys Leu Ser Cys
    130                 135                 140

Lys Ala Ser Gly Tyr Thr Phe Thr Ser Tyr Trp Met Gln Trp Val Lys
145                 150                 155                 160
```

```
Gln Arg Pro Gly Gln Gly Leu Glu Trp Ile Gly Glu Ile Asp Pro Ser
                165                 170                 175

Val Ser Tyr Thr Glu Tyr Asn Gln Lys Phe Lys Gly Lys Ala Thr Leu
            180                 185                 190

Thr Val Asp Thr Ser Ser Ser Thr Ala Tyr Met Gln Leu Ser Ser Leu
        195                 200                 205

Thr Ser Glu Asp Ser Ala Val Tyr Phe Cys Ala Arg Trp Ser Lys Asp
    210                 215                 220

Tyr Tyr Gly Met Asp Tyr Trp Gly Gln Gly Thr Ser Val Thr Val Ser
225                 230                 235                 240

Ser


<210> SEQ ID NO 149
<211> LENGTH: 12
<212> TYPE: PRT
<213> ORGANISM: Artificial Sequence
<220> FEATURE:
<223> OTHER INFORMATION: KLRG1 scFv-2 CDR-L1

<400> SEQUENCE: 149

Ser Val Ser Ser Ser Ile Ser Ser Ser Asn Leu His
1               5                   10


<210> SEQ ID NO 150
<211> LENGTH: 7
<212> TYPE: PRT
<213> ORGANISM: Artificial Sequence
<220> FEATURE:
<223> OTHER INFORMATION: KLRG1 scFv-2 CDR-L2

<400> SEQUENCE: 150

Gly Thr Ser Asn Leu Ala Ser
                5


<210> SEQ ID NO 151
<211> LENGTH: 9
<212> TYPE: PRT
<213> ORGANISM: Artificial Sequence
<220> FEATURE:
<223> OTHER INFORMATION: KLRG1 scFv-2 CDR-L3

<400> SEQUENCE: 151

Gln Gln Trp Ser Ser Tyr Pro Leu Thr
1               5


<210> SEQ ID NO 152
<211> LENGTH: 7
<212> TYPE: PRT
<213> ORGANISM: Artificial Sequence
<220> FEATURE:
<223> OTHER INFORMATION: KLRG1 scFv-2 CDR-H1

<400> SEQUENCE: 152

Gly Tyr Thr Phe Thr Ser Tyr
1               5


<210> SEQ ID NO 153
<211> LENGTH: 6
<212> TYPE: PRT
<213> ORGANISM: Artificial Sequence
<220> FEATURE:
<223> OTHER INFORMATION: KLRG1 scFv-2 CDR-H2

<400> SEQUENCE: 153
```

Tyr Pro Gly Ser Ser Ser
5

<210> SEQ ID NO 154
<211> LENGTH: 14
<212> TYPE: PRT
<213> ORGANISM: Artificial Sequence
<220> FEATURE:
<223> OTHER INFORMATION: KLRG1 scFv-2 CDR-H3

<400> SEQUENCE: 154

Gly Arg Leu Leu Arg Leu Arg Arg Gly Gly Tyr Phe Asp Tyr
1 5 10

<210> SEQ ID NO 155
<211> LENGTH: 108
<212> TYPE: PRT
<213> ORGANISM: Artificial Sequence
<220> FEATURE:
<223> OTHER INFORMATION: KLRG1 scFv-2 VL

<400> SEQUENCE: 155

Glu Ile Val Leu Thr Gln Ser Pro Ala Leu Met Ala Ala Ser Pro Gly
1 5 10 15

Glu Lys Val Thr Ile Thr Cys Ser Val Ser Ser Ser Ile Ser Ser Ser
20 25 30

Asn Leu His Trp Tyr Gln Gln Lys Ser Glu Thr Ser Pro Lys Pro Trp
35 40 45

Ile Tyr Gly Thr Ser Asn Leu Ala Ser Gly Val Pro Val Arg Phe Ser
50 55 60

Gly Ser Gly Ser Gly Thr Ser Tyr Ser Leu Thr Ile Ser Ser Met Glu
65 70 75 80

Ala Glu Asp Ala Ala Thr Tyr Tyr Cys Gln Gln Trp Ser Ser Tyr Pro
85 90 95

Leu Thr Phe Gly Ala Gly Thr Lys Leu Glu Leu Lys
100 105

<210> SEQ ID NO 156
<211> LENGTH: 123
<212> TYPE: PRT
<213> ORGANISM: Artificial Sequence
<220> FEATURE:
<223> OTHER INFORMATION: KLRG1 scFv-2 VH

<400> SEQUENCE: 156

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Ile Asn Trp Val Lys Gln Arg Pro Gly Gln Gly Leu Glu Trp Ile
35 40 45

Gly Asn Ile Tyr Pro Gly Ser Ser Ser Thr Asn Tyr Asn Glu Lys Phe
50 55 60

Lys Tyr Lys Ala Thr Leu Thr Val Asp Thr Ser Ser Ser Thr Ala Asn
65 70 75 80

Met Gln Leu Ser Ser Leu Thr Ser Asp Asp Ser Ala Val Tyr Tyr Cys
85 90 95

Ala Arg Gly Arg Leu Leu Arg Leu Arg Arg Gly Gly Tyr Phe Asp Tyr
100 105 110

Trp Gly Gln Gly Thr Thr Leu Thr Val Ser Ser 115 120

<210> SEQ ID NO 157
<211> LENGTH: 246
<212> TYPE: PRT
<213> ORGANISM: Artificial Sequence
<220> FEATURE:
<223> OTHER INFORMATION: KLRG1 scFv-2

<400> SEQUENCE: 157

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Thr Ser Tyr
20 25 30

Trp Ile Asn Trp Val Lys Gln Arg Pro Gly Gln Gly Leu Glu Trp Ile
35 40 45

Gly Asn Ile Tyr Pro Gly Ser Ser Ser Thr Asn Tyr Asn Glu Lys Phe
50 55 60

Lys Tyr Lys Ala Thr Leu Thr Val Asp Thr Ser Ser Ser Thr Ala Asn
65 70 75 80

Met Gln Leu Ser Ser Leu Thr Ser Asp Asp Ser Ala Val Tyr Tyr Cys
85 90 95

Ala Arg Gly Arg Leu Leu Arg Leu Arg Arg Gly Gly Tyr Phe Asp Tyr
100 105 110

Trp Gly Gln Gly Thr Thr Leu Thr Val Ser Ser Gly Gly Gly Gly Ser
115 120 125

Gly Gly Gly Gly Ser Gly Gly Gly Gly Ser Glu Ile Val Leu Thr Gln
130 135 140

Ser Pro Ala Leu Met Ala Ala Ser Pro Gly Glu Lys Val Thr Ile Thr
145 150 155 160

Cys Ser Val Ser Ser Ser Ile Ser Ser Ser Asn Leu His Trp Tyr Gln
165 170 175

Gln Lys Ser Glu Thr Ser Pro Lys Pro Trp Ile Tyr Gly Thr Ser Asn
180 185 190

Leu Ala Ser Gly Val Pro Val Arg Phe Ser Gly Ser Gly Ser Gly Thr
195 200 205

Ser Tyr Ser Leu Thr Ile Ser Ser Met Glu Ala Glu Asp Ala Ala Thr
210 215 220

Tyr Tyr Cys Gln Gln Trp Ser Ser Tyr Pro Leu Thr Phe Gly Ala Gly
225 230 235 240

Thr Lys Leu Glu Leu Lys
245

<210> SEQ ID NO 158
<211> LENGTH: 11
<212> TYPE: PRT
<213> ORGANISM: Artificial Sequence
<220> FEATURE:
<223> OTHER INFORMATION: KLRG1 scFv-3 CDR-L1

<400> SEQUENCE: 158

Arg Ala Ser Gln Asp Ile Tyr Gly Ser Leu Asn
1 5 10

<210> SEQ ID NO 159
<211> LENGTH: 7
<212> TYPE: PRT
<213> ORGANISM: Artificial Sequence
<220> FEATURE:

<223> OTHER INFORMATION: KLRG1 scFv-3 CDR-L2

<400> SEQUENCE: 159

Gly Thr Ser Ser Leu Asp Ser
5

<210> SEQ ID NO 160
<211> LENGTH: 9
<212> TYPE: PRT
<213> ORGANISM: Artificial Sequence
<220> FEATURE:
<223> OTHER INFORMATION: KLRG1 scFv-3 CDR-L3

<400> SEQUENCE: 160

Leu Gln Tyr Ala Ser Phe Pro Leu Thr
1 5

<210> SEQ ID NO 161
<211> LENGTH: 7
<212> TYPE: PRT
<213> ORGANISM: Artificial Sequence
<220> FEATURE:
<223> OTHER INFORMATION: KLRG1 scFv-3 CDR-H1

<400> SEQUENCE: 161

Gly Tyr Thr Phe Thr Ser Tyr
1 5

<210> SEQ ID NO 162
<211> LENGTH: 6
<212> TYPE: PRT
<213> ORGANISM: Artificial Sequence
<220> FEATURE:
<223> OTHER INFORMATION: KLRG1 scFv-3 CDR-H2

<400> SEQUENCE: 162

Asp Pro Ser Asp Ser Glu
5

<210> SEQ ID NO 163
<211> LENGTH: 12
<212> TYPE: PRT
<213> ORGANISM: Artificial Sequence
<220> FEATURE:
<223> OTHER INFORMATION: KLRG1 scFv-3 CDR-H3

<400> SEQUENCE: 163

Gly Arg Leu Leu Arg Leu Arg Asp Trp Phe Pro Tyr
1 5 10

<210> SEQ ID NO 164
<211> LENGTH: 107
<212> TYPE: PRT
<213> ORGANISM: Artificial Sequence
<220> FEATURE:
<223> OTHER INFORMATION: KLRG1 scFv-3 VL

<400> SEQUENCE: 164

Asp Ile Gln Met Thr Gln Ser Pro Ser Ser Leu Ser Ala Ser Leu Gly
1 5 10 15

Glu Arg Ile Ser Leu Thr Cys Arg Ala Ser Gln Asp Ile Tyr Gly Ser
20 25 30

Leu Asn Trp Phe Gln Gln Lys Pro Asp Gly Thr Ile Lys Leu Leu Ile
35 40 45

Tyr Gly Thr Ser Ser Leu Asp Ser Gly Val Pro Lys Arg Phe Ser Gly

```
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Phe Pro Leu
                85                  90                  95

Thr Phe Gly Ala Gly Thr Lys Leu Glu Leu Lys
            100                 105


<210> SEQ ID NO 165
<211> LENGTH: 121
<212> TYPE: PRT
<213> ORGANISM: Artificial Sequence
<220> FEATURE:
<223> OTHER INFORMATION: KLRG1 scFv-3 VH

<400> SEQUENCE: 165

Gln Val Gln Leu Gln Gln Pro Gly Ala Glu Met Val Arg Pro Gly Ala
1               5                   10                  15

Ser Val Lys Leu Ser Cys Lys Thr Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Lys Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Gly Arg Leu Leu Arg Leu Arg Asp Trp Phe Pro Tyr Trp Gly
            100                 105                 110

Gln Gly Thr Leu Val Thr Val Ser Ala
        115                 120


<210> SEQ ID NO 166
<211> LENGTH: 243
<212> TYPE: PRT
<213> ORGANISM: Artificial Sequence
<220> FEATURE:
<223> OTHER INFORMATION: KLRG1 scFv-3

<400> SEQUENCE: 166

Gln Val Gln Leu Gln Gln Pro Gly Ala Glu Met Val Arg Pro Gly Ala
1               5                   10                  15

Ser Val Lys Leu Ser Cys Lys Thr Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Lys Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Gly Arg Leu Leu Arg Leu Arg Asp Trp Phe Pro Tyr Trp Gly
            100                 105                 110

Gln Gly Thr Leu Val Thr Val Ser Ala Gly Gly Gly Gly Ser Gly Gly
        115                 120                 125
```

Gly Gly Ser Gly Gly Gly Gly Ser Asp Ile Gln Met Thr Gln Ser Pro
130 135 140

Ser Ser Leu Ser Ala Ser Leu Gly Glu Arg Ile Ser Leu Thr Cys Arg
145 150 155 160

Ala Ser Gln Asp Ile Tyr Gly Ser Leu Asn Trp Phe Gln Gln Lys Pro
165 170 175

Asp Gly Thr Ile Lys Leu Leu Ile Tyr Gly Thr Ser Ser Leu Asp Ser
180 185 190

Gly Val Pro Lys Arg Phe Ser Gly Ser Arg Ser Gly Ser Asp Tyr Ser
195 200 205

Leu Thr Ile Ser Ser Leu Glu Ser Glu Asp Phe Ala Asp Tyr Tyr Cys
210 215 220

Leu Gln Tyr Ala Ser Phe Pro Leu Thr Phe Gly Ala Gly Thr Lys Leu
225 230 235 240

Glu Leu Lys

<210> SEQ ID NO 167
<211> LENGTH: 16
<212> TYPE: PRT
<213> ORGANISM: Artificial Sequence
<220> FEATURE:
<223> OTHER INFORMATION: KLRG1 scFv-4 CDR-L1

<400> SEQUENCE: 167

Lys Ser Ser Gln Ser Leu Leu Tyr Ser Asp Gly Lys Thr Tyr Leu Asn
1 5 10 15

<210> SEQ ID NO 168
<211> LENGTH: 7
<212> TYPE: PRT
<213> ORGANISM: Artificial Sequence
<220> FEATURE:
<223> OTHER INFORMATION: KLRG1 scFv-4 CDR-L2

<400> SEQUENCE: 168

Leu Val Ser Glu Leu Glu Ser
5

<210> SEQ ID NO 169
<211> LENGTH: 9
<212> TYPE: PRT
<213> ORGANISM: Artificial Sequence
<220> FEATURE:
<223> OTHER INFORMATION: KLRG1 scFv-4 CDR-L3

<400> SEQUENCE: 169

Val Gln Gly Thr His Phe Pro Trp Thr
1 5

<210> SEQ ID NO 170
<211> LENGTH: 7
<212> TYPE: PRT
<213> ORGANISM: Artificial Sequence
<220> FEATURE:
<223> OTHER INFORMATION: KLRG1 scFv-4 CDR-H1

<400> SEQUENCE: 170

Gly Tyr Thr Phe Thr Asn Tyr
1 5

<210> SEQ ID NO 171
<211> LENGTH: 6
<212> TYPE: PRT

<213> ORGANISM: Artificial Sequence
<220> FEATURE:
<223> OTHER INFORMATION: KLRG1 scFv-4 CDR-H2

<400> SEQUENCE: 171

Tyr Pro Gly Asn Ser Asp
5

<210> SEQ ID NO 172
<211> LENGTH: 10
<212> TYPE: PRT
<213> ORGANISM: Artificial Sequence
<220> FEATURE:
<223> OTHER INFORMATION: KLRG1 scFv-4 CDR-H3

<400> SEQUENCE: 172

Glu Gly Asp Tyr Val Tyr Ala Met Asp Tyr
1 5 10

<210> SEQ ID NO 173
<211> LENGTH: 112
<212> TYPE: PRT
<213> ORGANISM: Artificial Sequence
<220> FEATURE:
<223> OTHER INFORMATION: KLRG1 scFv-4 VL

<400> SEQUENCE: 173

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Tyr Ser
20 25 30

Asp Gly Lys Thr Tyr Leu Asn Trp Leu Leu Gln Ser Pro Gly Gln Ser
35 40 45

Pro Lys Leu Leu Ile Tyr Leu Val Ser Glu Leu Glu Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Val Gln Gly
85 90 95

Thr His Phe Pro Trp Thr Phe Gly Gly Gly Thr Lys Leu Glu Ile Lys
100 105 110

<210> SEQ ID NO 174
<211> LENGTH: 119
<212> TYPE: PRT
<213> ORGANISM: Artificial Sequence
<220> FEATURE:
<223> OTHER INFORMATION: KLRG1 scFv-4 VH

<400> SEQUENCE: 174

Glu Val Gln Leu Gln Gln Ser Gly Thr Val Leu Ala Arg Pro Gly Ala
1 5 10 15

Ser Val Lys Met Ser Cys Lys Ala Ser Gly Tyr Thr Phe Thr Asn Tyr
20 25 30

Trp Met His Trp Val Lys Gln Arg Pro Gly Gln Gly Leu Glu Trp Ile
35 40 45

Gly Ala Ile Tyr Pro Gly Asn Ser Asp Thr Thr Tyr Asn Gln Lys Phe
50 55 60

Lys Gly Lys Ala Lys Leu Thr Ala Val Thr Ser Ala Thr Thr Ala Tyr
65 70 75 80

Met Glu Leu Ser Ser Leu Thr Asn Glu Gly Ser Ala Val Tyr Tyr Cys 85 90 95

Thr Arg Glu Gly Asp Tyr Val Tyr Ala Met Asp Tyr Trp Gly Gln Gly
100 105 110

Thr Ser Val Thr Val Ser Ser
115

<210> SEQ ID NO 175
<211> LENGTH: 246
<212> TYPE: PRT
<213> ORGANISM: Artificial Sequence
<220> FEATURE:
<223> OTHER INFORMATION: KLRG1 scFv-4

<400> SEQUENCE: 175

Glu Val Gln Leu Gln Gln Ser Gly Thr Val Leu Ala Arg Pro Gly Ala
1 5 10 15

Ser Val Lys Met Ser Cys Lys Ala Ser Gly Tyr Thr Phe Thr Asn Tyr
20 25 30

Trp Met His Trp Val Lys Gln Arg Pro Gly Gln Gly Leu Glu Trp Ile
35 40 45

Gly Ala Ile Tyr Pro Gly Asn Ser Asp Thr Thr Tyr Asn Gln Lys Phe
50 55 60

Lys Gly Lys Ala Lys Leu Thr Ala Val Thr Ser Ala Thr Thr Ala Tyr
65 70 75 80

Met Glu Leu Ser Ser Leu Thr Asn Glu Gly Ser Ala Val Tyr Tyr Cys
85 90 95

Thr Arg Glu Gly Asp Tyr Val Tyr Ala Met Asp Tyr Trp Gly Gln Gly
100 105 110

Thr Ser Val Thr Val Ser Ser Gly Gly Gly Gly Ser Gly Gly Gly Gly
115 120 125

Ser Gly Gly Gly Gly Ser Asp Val Val Met Thr Gln Thr Pro Leu Thr
130 135 140

Leu Ser Val Thr Ile Gly Gln Pro Ala Ser Ile Ser Cys Lys Ser Ser
145 150 155 160

Gln Ser Leu Leu Tyr Ser Asp Gly Lys Thr Tyr Leu Asn Trp Leu Leu
165 170 175

Gln Ser Pro Gly Gln Ser Pro Lys Leu Leu Ile Tyr Leu Val Ser Glu
180 185 190

Leu Glu Ser Gly Val Pro Asp Arg Phe Ser Gly Ser Gly Ser Gly Thr
195 200 205

Asp Phe Thr Leu Lys Ile Ser Arg Val Glu Ala Glu Asp Leu Gly Val
210 215 220

Tyr Tyr Cys Val Gln Gly Thr His Phe Pro Trp Thr Phe Gly Gly Gly
225 230 235 240

Thr Lys Leu Glu Ile Lys
245

<210> SEQ ID NO 176
<211> LENGTH: 11
<212> TYPE: PRT
<213> ORGANISM: Artificial Sequence
<220> FEATURE:
<223> OTHER INFORMATION: SIGLEC7/9 scFv-1 CDR-L1

<400> SEQUENCE: 176

Lys Ala Ser Gln Asp Val Asn Thr Ala Val Ala
1 5 10

<210> SEQ ID NO 177
<211> LENGTH: 7
<212> TYPE: PRT
<213> ORGANISM: Artificial Sequence
<220> FEATURE:
<223> OTHER INFORMATION: SIGLEC7/9 scFv-1 CDR-L2

<400> SEQUENCE: 177

Ser Ala Ser Tyr Arg Tyr Thr
5

<210> SEQ ID NO 178
<211> LENGTH: 9
<212> TYPE: PRT
<213> ORGANISM: Artificial Sequence
<220> FEATURE:
<223> OTHER INFORMATION: SIGLEC7/9 scFv-1 CDR-L3

<400> SEQUENCE: 178

Gln Gln His Tyr Ser Thr Pro Arg Thr
1 5

<210> SEQ ID NO 179
<211> LENGTH: 8
<212> TYPE: PRT
<213> ORGANISM: Artificial Sequence
<220> FEATURE:
<223> OTHER INFORMATION: SIGLEC7/9 scFv-1 CDR-H1

<400> SEQUENCE: 179

Gly Tyr Ser Ile Thr Gly Gly Phe
1 5

<210> SEQ ID NO 180
<211> LENGTH: 5
<212> TYPE: PRT
<213> ORGANISM: Artificial Sequence
<220> FEATURE:
<223> OTHER INFORMATION: SIGLEC7/9 scFv-1 CDR-H2

<400> SEQUENCE: 180

Gly Tyr Gly Gly Ser
5

<210> SEQ ID NO 181
<211> LENGTH: 7
<212> TYPE: PRT
<213> ORGANISM: Artificial Sequence
<220> FEATURE:
<223> OTHER INFORMATION: SIGLEC7/9 scFv-1 CDR-H3

<400> SEQUENCE: 181

Gly Asp Tyr Leu Phe Ala Tyr
5

<210> SEQ ID NO 182
<211> LENGTH: 107
<212> TYPE: PRT
<213> ORGANISM: Artificial Sequence
<220> FEATURE:
<223> OTHER INFORMATION: SIGLEC7/9 scFv-1 VL

<400> SEQUENCE: 182

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Asn Thr Ala 20 25 30

Val Ala Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Thr Gly
50 55 60

Ser Gly Ser Gly Thr Asp Phe Thr Phe Thr Ile Ser Ser Val Gln Ala
65 70 75 80

Glu Asp Leu Ala Val Tyr Tyr Cys Gln Gln His Tyr Ser Thr Pro Arg
85 90 95

Thr Phe Gly Gly Gly Thr Lys Leu Glu Ile Lys
100 105

<210> SEQ ID NO 183
<211> LENGTH: 115
<212> TYPE: PRT
<213> ORGANISM: Artificial Sequence
<220> FEATURE:
<223> OTHER INFORMATION: SIGLEC7/9 scFv-1 VH

<400> SEQUENCE: 183

Asp Val Gln Leu Gln Glu Ser Gly Pro Leu Val Lys Pro Ser Gln Ser
1 5 10 15

Leu Ser Leu Thr Cys Thr Val Thr Gly Tyr Ser Ile Thr Gly Gly Phe
20 25 30

Ala Trp Asn Trp Ile Arg Gln Phe Pro Gly Asn Thr Leu Glu Trp Met
35 40 45

Gly Tyr Ile Gly Tyr Gly Gly Ser Thr Ser Tyr Asn Pro Ser Leu Asn
50 55 60

Ser Arg Ile Ser Ile Thr Arg Asp Thr Ser Lys Asn His Phe Phe Leu
65 70 75 80

Gln Phe Asn Ser Val Thr Thr Asp Asp Ser Ala Thr Tyr Tyr Cys Ala
85 90 95

Arg Gly Asp Tyr Leu Phe Ala Tyr Trp Gly Gln Gly Thr Leu Val Thr
100 105 110

Val Ser Ala
115

<210> SEQ ID NO 184
<211> LENGTH: 237
<212> TYPE: PRT
<213> ORGANISM: Artificial Sequence
<220> FEATURE:
<223> OTHER INFORMATION: SIGLEC7/9 scFv-1

<400> SEQUENCE: 184

Asp Val Gln Leu Gln Glu Ser Gly Pro Leu Val Lys Pro Ser Gln Ser
1 5 10 15

Leu Ser Leu Thr Cys Thr Val Thr Gly Tyr Ser Ile Thr Gly Gly Phe
20 25 30

Ala Trp Asn Trp Ile Arg Gln Phe Pro Gly Asn Thr Leu Glu Trp Met
35 40 45

Gly Tyr Ile Gly Tyr Gly Gly Ser Thr Ser Tyr Asn Pro Ser Leu Asn
50 55 60

Ser Arg Ile Ser Ile Thr Arg Asp Thr Ser Lys Asn His Phe Phe Leu
65 70 75 80

Gln Phe Asn Ser Val Thr Thr Asp Asp Ser Ala Thr Tyr Tyr Cys Ala
85 90 95

```
Arg Gly Asp Tyr Leu Phe Ala Tyr Trp Gly Gln Gly Thr Leu Val Thr
            100                 105                 110

Val Ser Ala Gly Gly Gly Gly Ser Gly Gly Gly Gly Ser Gly Gly Gly
        115                 120                 125

Gly Ser Asp Ile Val Met Thr Gln Ser His Lys Phe Met Ser Thr Ser
    130                 135                 140

Val Gly Asp Arg Val Ser Ile Thr Cys Lys Ala Ser Gln Asp Val Asn
145                 150                 155                 160

Thr Ala Val Ala Trp Tyr Gln Gln Lys Pro Gly Gln Ser Pro Lys Leu
                165                 170                 175

Leu Ile Tyr Ser Ala Ser Tyr Arg Tyr Thr Gly Val Pro Asp Arg Phe
            180                 185                 190

Thr Gly Ser Gly Ser Gly Thr Asp Phe Thr Phe Thr Ile Ser Ser Val
        195                 200                 205

Gln Ala Glu Asp Leu Ala Val Tyr Tyr Cys Gln Gln His Tyr Ser Thr
    210                 215                 220

Pro Arg Thr Phe Gly Gly Gly Thr Lys Leu Glu Ile Lys
225                 230                 235
```

<210> SEQ ID NO 185
<211> LENGTH: 107
<212> TYPE: PRT
<213> ORGANISM: Artificial Sequence
<220> FEATURE:
<223> OTHER INFORMATION: SIGLEC7/9 scFv-1-2 VL

<400> SEQUENCE: 185

```
Asp Thr Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105
```

<210> SEQ ID NO 186
<211> LENGTH: 116
<212> TYPE: PRT
<213> ORGANISM: Artificial Sequence
<220> FEATURE:
<223> OTHER INFORMATION: SIGLEC7/9 scFv-1-2 VH

<400> SEQUENCE: 186

```
Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Gly Gly
            20                  25                  30

Phe Ala Trp Asn Trp Ile Arg Gln Phe Pro Gly Asn Thr Leu Glu Trp
        35                  40                  45

Met Gly Tyr Ile Gly Tyr Gly Gly Ser Thr Ser Tyr Asn Pro Ser Leu
    50                  55                  60
```

Asn Ser Arg Ile Ser Ile Thr Arg Asp Thr Ser Lys Asn His Phe Phe
65 70 75 80

Leu Gln Phe Asn Ser Val Thr Thr Glu Asp Ser Ala Thr Tyr Tyr Cys
85 90 95

Ala Arg Gly Asp Tyr Leu Phe Ala Tyr Trp Gly Gln Gly Thr Leu Val
100 105 110

Thr Val Ser Ala
115

<210> SEQ ID NO 187
<211> LENGTH: 238
<212> TYPE: PRT
<213> ORGANISM: Artificial Sequence
<220> FEATURE:
<223> OTHER INFORMATION: SIGLEC7/9 scFv-1-2

<400> SEQUENCE: 187

Glu Val Gln Leu Gln Glu Ser Gly Pro Gly Leu Val Lys Pro Ser Gln
1 5 10 15

Ser Leu Ser Leu Thr Cys Thr Val Thr Gly Tyr Ser Ile Thr Gly Gly
20 25 30

Phe Ala Trp Asn Trp Ile Arg Gln Phe Pro Gly Asn Thr Leu Glu Trp
35 40 45

Met Gly Tyr Ile Gly Tyr Gly Gly Ser Thr Ser Tyr Asn Pro Ser Leu
50 55 60

Asn Ser Arg Ile Ser Ile Thr Arg Asp Thr Ser Lys Asn His Phe Phe
65 70 75 80

Leu Gln Phe Asn Ser Val Thr Thr Glu Asp Ser Ala Thr Tyr Tyr Cys
85 90 95

Ala Arg Gly Asp Tyr Leu Phe Ala Tyr Trp Gly Gln Gly Thr Leu Val
100 105 110

Thr Val Ser Ala Gly Gly Gly Gly Ser Gly Gly Gly Gly Ser Gly Gly
115 120 125

Gly Gly Ser Asp Thr Val Met Thr Gln Ser His Lys Phe Met Ser Thr
130 135 140

Ser Val Gly Asp Arg Val Ser Ile Thr Cys Lys Ala Ser Gln Asp Val
145 150 155 160

Asn Thr Ala Val Ala Trp Tyr Gln Gln Lys Pro Gly Gln Ser Pro Lys
165 170 175

Leu Leu Ile Tyr Ser Ala Ser Tyr Arg Tyr Thr Gly Val Pro Asp Arg
180 185 190

Phe Thr Gly Ser Gly Ser Gly Thr Asp Phe Thr Phe Thr Ile Ser Ser
195 200 205

Val Gln Ala Glu Asp Leu Ala Val Tyr Tyr Cys Gln Gln His Tyr Ser
210 215 220

Thr Pro Arg Thr Phe Gly Gly Gly Thr Lys Leu Glu Ile Lys
225 230 235

<210> SEQ ID NO 188
<211> LENGTH: 11
<212> TYPE: PRT
<213> ORGANISM: Artificial Sequence
<220> FEATURE:
<223> OTHER INFORMATION: SIGLEC7/9 scFv-2 CDR-L1

<400> SEQUENCE: 188

Lys Ala Ser Gln Asn Val Gly Thr Asn Val Ala 1 5 10

<210> SEQ ID NO 189
<211> LENGTH: 7
<212> TYPE: PRT
<213> ORGANISM: Artificial Sequence
<220> FEATURE:
<223> OTHER INFORMATION: SIGLEC7/9 scFv-2 CDR-L2

<400> SEQUENCE: 189

Ser Ala Ser Ser Arg Tyr Ser
5

<210> SEQ ID NO 190
<211> LENGTH: 9
<212> TYPE: PRT
<213> ORGANISM: Artificial Sequence
<220> FEATURE:
<223> OTHER INFORMATION: SIGLEC7/9 scFv-2 CDR-L3

<400> SEQUENCE: 190

Gln Gln Tyr Ile Thr Tyr Pro Tyr Thr
1 5

<210> SEQ ID NO 191
<211> LENGTH: 7
<212> TYPE: PRT
<213> ORGANISM: Artificial Sequence
<220> FEATURE:
<223> OTHER INFORMATION: SIGLEC7/9 scFv-2 CDR-H1

<400> SEQUENCE: 191

Gly Tyr Ser Phe Ser Asp Tyr
1 5

<210> SEQ ID NO 192
<211> LENGTH: 6
<212> TYPE: PRT
<213> ORGANISM: Artificial Sequence
<220> FEATURE:
<223> OTHER INFORMATION: SIGLEC7/9 scFv-2 CDR-H2

<400> SEQUENCE: 192

Asp Pro Tyr Tyr Gly Ala
5

<210> SEQ ID NO 193
<211> LENGTH: 7
<212> TYPE: PRT
<213> ORGANISM: Artificial Sequence
<220> FEATURE:
<223> OTHER INFORMATION: SIGLEC7/9 scFv-2 CDR-H3

<400> SEQUENCE: 193

Gly Asp Ser Leu Phe Ala Tyr
5

<210> SEQ ID NO 194
<211> LENGTH: 107
<212> TYPE: PRT
<213> ORGANISM: Artificial Sequence
<220> FEATURE:
<223> OTHER INFORMATION: SIGLEC7/9 scFv-2 VL

<400> SEQUENCE: 194

Asp Ile Val Met Thr Gln Ser Gln Glu Phe Met Ser Thr Ser Leu Gly
1 5 10 15

```
Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Leu
        35                  40                  45

Tyr Ser Ala Ser Ser Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ile Thr Tyr Pro Tyr
                85                  90                  95

Thr Phe Gly Gly Gly Thr Lys Leu Glu Ile Lys
            100                 105


<210> SEQ ID NO 195
<211> LENGTH: 116
<212> TYPE: PRT
<213> ORGANISM: Artificial Sequence
<220> FEATURE:
<223> OTHER INFORMATION: SIGLEC7/9 scFv-2 VH

<400> SEQUENCE: 195

Glu Ile Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Ser Asp Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Ala Thr Ser Tyr Asn Gln Arg Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asp Ser Leu Phe Ala Tyr Trp Gly His Gly Thr Leu Val
            100                 105                 110

Thr Val Ser Ala
        115


<210> SEQ ID NO 196
<211> LENGTH: 238
<212> TYPE: PRT
<213> ORGANISM: Artificial Sequence
<220> FEATURE:
<223> OTHER INFORMATION: SIGLEC7/9 scFv-2

<400> SEQUENCE: 196

Glu Ile Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Ser Asp Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Ala Thr Ser Tyr Asn Gln Arg Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
```

-continued

```
                85                  90                  95

Ala Arg Gly Asp Ser Leu Phe Ala Tyr Trp Gly His Gly Thr Leu Val
            100                 105                 110

Thr Val Ser Ala Gly Gly Gly Gly Ser Gly Gly Gly Gly Ser Gly Gly
        115                 120                 125

Gly Gly Ser Asp Ile Val Met Thr Gln Ser Gln Glu Phe Met Ser Thr
    130                 135                 140

Ser Leu Gly Asp Arg Val Ser Val Thr Cys Lys Ala Ser Gln Asn Val
145                 150                 155                 160

Gly Thr Asn Val Ala Trp Tyr Gln Gln Lys Pro Gly Gln Ser Pro Lys
                165                 170                 175

Ala Leu Leu Tyr Ser Ala Ser Ser Arg Tyr Ser Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Glu Tyr Phe Cys Gln Gln Tyr Ile Thr
    210                 215                 220

Tyr Pro Tyr Thr Phe Gly Gly Gly Thr Lys Leu Glu Ile Lys
225                 230                 235
```

ENGINEERED IMMUNE CELL EXPRESSING NK INHIBITORY MOLECULE AND USE THEREOF

CROSS-REFERENCE TO RELATED APPLICATIONS

This application is a national phase filing under 35 U.S.C. § 371 of International Application No. PCT/CN2021/099314 filed on Jun. 10, 2021, which claims the benefit of Chinese Patent Application No. 202010527572.0, filed on Jun. 11, 2020, and of Chinese Patent Application No. 202011209420.2, filed on Nov. 3, 2020. The contents of the aforementioned applications are incorporated by reference in their entirety herein.

ELECTRONIC FILE—SEQUENCE LISTING

This application contains an electronic Sequence Listing which has been submitted in ASCII format via EFS-WEB and is hereby incorporated by reference in its entirety. The material in the electronic Sequence Listing is submitted as a text (.txt) file entitled "OPI22171051CNUS-corrected-sequence-listing" created on Jan. 19, 2023, and has a file size of 128,589 bytes.

TECHNICAL FIELD

The present disclosure belongs to the field of immunotherapy. More specifically, the present disclosure relates to an NK inhibitory molecule comprising one or more NK inhibitory ligands, a transmembrane domains, and a co-stimulatory domain, wherein the NK inhibitory ligands specifically bind to NK inhibitory receptors to inhibit the killing of NK cells against the engineered immune cells expressing the NK inhibitory molecule.

BACKGROUND ART

In recent years, cancer immunotherapy technology has been rapidly developed, and particularly immunotherapy associated with chimeric antigen receptor T cell (CAR-T) has achieved excellent clinical effects in the treatment of hematologic tumors. CAR-T cell immunotherapy is to genetically modify T cells in vitro to enable the T cells to recognize tumor antigens, and the T cells, after being amplified to a certain amount, are infused back into the patients' body to kill the cancer cells, thus achieving the purpose of treating tumors.

In 2017, two autologous CAR-T therapies were approved by the FDA and launched in US, one for B-cell acute leukemia and the other for diffuse B-cell non-Hodgkin's lymphoma. Although these two CAR-T cells have excellent clinical treatment effects, they are expensive and have a long preparation cycle, making the large-scale promotion quite difficult. Therefore, it is necessary to develop a universal CAR-T product to solve the above problems. Universal CAR-T can be prepared by using T cells isolated from peripheral blood of healthy donors, thereby realizing allogeneic transfusion, and greatly shortening the waiting time of a patient for treatment. Besides, the viability and function of T cells obtained from healthy donors are also superior to those of patient-derived T cells, which can increase the CAR infection rate and improve the therapeutic effect.

However, the development of universal CAR-T cells still faces two problems: (1) after the engineered CAR-T cells enter a patient's body and proliferate to a certain extent, they may attack normal cells or tissues of the patient, thus generating graft-versus-host disease (GvHD); and (2) the normal immune system in the patient's body may reject exogenous CAR-T cells, thus causing host-versus-graft disease (HvGD). Currently, HvGD is reduced or avoided mainly by knocking out CD52 or HLA. Specifically, knocking out CD52 can make the universal CAR-T cells resistant to Alemtuzumab (CD52 antibody), thereby avoiding killing of the introduced CAR-T cells when Alemtuzumab is used to clear the T cells of the patient. However, using Alemtuzumab will increase the production and treatment costs of the universal CAR-T product. On the other hand, although knocking out HLA molecule can prevent CAR-T cells from killing by the patient's T cells without using an antibody or other treatments, cells with HLA molecule being knocked out will be recognized by NK cells of the patient and cause rejection reaction.

Therefore, the existing universal CAR cell therapy still needs to be improved, especially reducing the killing effect of NK cells against CAR cells, thereby further reducing or avoiding the risk of HvGD.

SUMMARY

In the first aspect, the present disclosure provides an NK inhibitory molecule, which contains one or more NK inhibitory ligands, a transmembrane domain, and a co-stimulatory domain, wherein the NK inhibitory ligands specifically bind to NK inhibitory receptors (NKIR) to inhibit the killing of NK cells against engineered immune cells expressing the NK inhibitory molecule.

In an embodiment, the NK inhibitory ligand is an antibody targeting NKIR or a functional fragment thereof, or a natural ligand of NKIR or an NKIR binding fragment contained therein. In an embodiment, the NKIR is selected from the group consisting of an NKG2/CD94 component (e.g., NKG2A, NKG2B, CD94); a killer cell Ig-like receptor (KIR) family member (e.g., KIR2DL1, KIR2DL2/3, KIR2DL5A, KIR2DL5B, KIR3DL1, KIR3DL2, and KIR3DL3); a leukocyte Ig-like receptor (LIR) family member (e.g., LIR1, LIR2, LIR3, LIR5, and LIR8); an NK cell receptor protein 1 (NKR-P1) family member (e.g., NKR-P1B and NKR-P1D); an immune checkpoint receptor (e.g., PD-1, TIGIT and CD96, TIM3, LAG3); a carcinoembryonic antigen-related cellular adhesion molecule 1 (CEACAM1); a sialic acid-binding immunoglobulin-like lectin (SIGLEC) family member (e.g., SIGLEC7 and SIGLEC9); a leukocyte-associated immunoglobulin-like receptor 1 (LAIR1); an Ly49 family member (e.g. Ly49A, Ly49C, Ly49F, Ly49G1, and Ly49G4), and a killer cell lectin-like receptor G1 (KLRG1). Preferably, the NKIR is selected from the group consisting of PDT, NKG2A, NKG2B, CD94, LIR1, LIR2, LIR3, KIR2DLT, KIR2DL2/3, KIR3DL1, CEACAM1, LAIR1, SIGLEC7, SIGLEC9, and KLRG1. More preferably, the NKIR is selected from the group consisting of PDT, NKG2A, CD94, KIR2DL1, KIR2DL2/3, KIR3DL1, LIR1, CEACAM1, LAIR1, SIGLEC7, SIGLEC9, and KLRG1.

In an embodiment, the NK inhibitory ligand is an antibody targeting NKIR, and the antibody is an intact antibody, Fab, Fab', F(ab')2, Fv fragment, scFv antibody fragment, linear antibody, sdAb or nanobody. In a preferred embodiment, the NK inhibitory ligand is an antibody targeting PD1, NKG2A, LIR1, KIR, SIGLEC7, SIGLEC9 and/or KLRG1 or a functional fragment thereof.

In an embodiment, the NK inhibitory ligand is a natural ligand of NKIR or an NKIR binding fragment contained therein. Preferably, the NK inhibitory ligand is selected from the group consisting of HLA-E, HLA-F, HLA-G, cadherin, collagen, OCIL, sialic acid, immune checkpoint ligand (such as PD-L1/PD-L2, CD155, CD112, CD113, Gal-9, and FGL1), and an NKIR binding region contained therein. More preferably, the NK inhibitory ligand is sialic acid, HLA-E, HLA-F, HLA-G, cadherin, PD-L1, PD-L2 or an NKIR binding region contained therein. More preferably, the NK inhibitory ligand is selected from the group consisting of sialic acid, HLA-E extracellular region, HLA-G extracellular region, E-cadherin extracellular region, PD-L1 extracellular region, and PD-L2 extracellular region. More preferably, the NK inhibitory ligand is an E-cadherin extracellular region comprising EC1 and EC2, and more preferably comprising EC1, EC2, EC3, EC4, and EC5.

In an embodiment, the transmembrane domain comprised in the NK inhibitory molecule is a transmembrane domain of a protein selected from the group consisting of TCR α chain, TCR β chain, TCR γ chain, TCR δ chain, CD3 ζ subunit, CD3 ε subunit, CD3 γ subunit, CD3 δ subunit, CD45, CD4, CD5, CD8 α, CD9, CD16, CD22, CD33, CD28, CD37, CD64, CD80, CD86, CD134, CD137, CD154, and the transmembrane domain of an NKIR natural ligand, such as HLA-E, HLA-F, HLA-G, cadherin, collagen, and OCIL. In a preferred embodiment, the transmembrane domain is selected from a transmembrane domain of CD 8 α, CD4, CD28, and CD278.

In an embodiment, the transmembrane domain has at least 70%, preferably at least 80%, more preferably at least 90%, 95%, 97% or 99% or 100% sequence identity to an amino acid sequence represented by SEQ ID NO: 9 or 11.

In an embodiment, the NK inhibitory molecule comprises a co-stimulatory domain, which is a co-stimulatory signaling domain of a protein selected from the group consisting of LTB, CD94, TLR1, TLR2, TLR3, TLR4, TLR5, TLR6, TLR7, TLR8, TLR9, TLR10, CARD11, CD2, CD7, CD8, CD18, CD27, CD28, CD30, CD40, CD54, CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, ZAP70, and a combination thereof. Preferably, the co-stimulatory domain of the present disclosure is from 4-1BB, CD28, CD27, OX40, CD278 or a combination thereof.

In an embodiment, the co-stimulatory domain has at least 70%, preferably at least 80%, more preferably at least 90%, 95%, 97% or 99% or 100% sequence identity to an amino acid sequence represented by SEQ ID NO: 13 or 15.

In an embodiment, the NK inhibitory molecule does not comprise an intracellular signaling domain. In another embodiment, the NK inhibitory molecule further comprises an intracellular signaling domain.

In an embodiment, the intracellular signaling domain is a signaling domain of a protein selected from the group consisting of: FcR γ, FcR β, CD3 γ, CD3 δ, CD3 ε, CD3 ζ, CD22, CD79a, CD79b, and CD66d. Preferably, the intracellular signaling domain comprises the signaling domain of CD3 ζ.

In an embodiment, the intracellular signaling domain has at least 70%, preferably at least 80%, more preferably at least 90%, 95%, 97% or 99% or 100% sequence identity to an amino acid sequence represented by SEQ ID NO: 17 or 19.

The present disclosure further provides a nucleic acid encoding the above NK inhibitory molecule, and a vector containing the nucleic acid.

In the second aspect, the present disclosure provides an engineered immune cell, characterized in that it (1) expresses the NK inhibitory molecule of the present disclosure, and (2) the expression of at least one MHC-related gene is suppressed or silenced. In an embodiment, the engineered immune cell of the present disclosure further expresses a chimeric antigen receptor, wherein the chimeric antigen receptor contains a ligand binding domain, a transmembrane domain, a co-stimulatory domain, and an intracellular signaling domain.

In one aspect, the present disclosure provides an engineered immune cell, characterized in that it (1) expresses a fusion protein of the NK inhibitory molecule of the present disclosure and a chimeric antigen receptor, wherein the fusion protein comprises an NK inhibitory ligand, a ligand binding domain, a transmembrane domain, a co-stimulatory domain, and an intracellular signaling domain, and (2) the expression of at least one MHC-related gene is suppressed or silenced.

In an embodiment, the MHC-related gene is selected from the group consisting of HLA-A, HLA-B, HLA-C, B2M, HLA-DPA, HLA-DQ, HLA-DRA, TAP1, TAP2, LMP2, LMP7, RFX5, RFXAP, RFXANK, CIITA, and a combination thereof, preferably HLA-A, HLA-B, HLA-C, B2M, RFX5, RFXAP, RFXANK, CIITA, and a combination thereof.

In an embodiment, the expression of at least one TCR/CD3 gene of the engineered immune cell is suppressed or silenced, and the TCR/CD3 gene is selected from the group consisting of TRAC, TRBC, CD3 γ, CD3 δ, CD3 ε, CD3 ζ, and a combination thereof.

In a preferred embodiment, expression of at least one TCR/CD3 gene and at least one MHC-related gene of the engineered immune cell is suppressed or silenced, wherein the at least one TCR/CD3 gene is selected from the group consisting of TRAC, TRBC, and a combination thereof, and the at least one MHC-related gene is selected from the group consisting of B2M, RFX5, RFXAP, RFXANK, CIITA, and a combination thereof. In an embodiment, expression of TRAC or TRBC and expression of B2M of the engineered immune cell are suppressed or silenced. In an embodiment, expression of TRAC or TRBC and expression of CIITA of the engineered immune cell are suppressed or silenced. In a preferred embodiment, expression of TRAC or TRBC, and expression of B2M and CIITA of the engineered immune cell are suppressed or silenced. In a preferred embodiment, expression of TRAC or TRBC, and expression of B2M and RFX5 of the engineered immune cell are suppressed or silenced.

In an embodiment, the engineered immune cell of the present disclosure is further characterized in that expression of one or more genes is suppressed or silenced, wherein the one or more genes are selected from the group consisting of CD52, GR, dCK, and immune checkpoint gene, such as PD1, LAG3, TIM3, CTLA4, PPP2CA, PPP2CB, PTPN6, PTPN22, PDCD1, HAVCR2, BTLA, CD160, TIGIT, CD96, CRTAM, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAGI, SIT, FOXP3, PRDM1, BATF, GUCY1A2, GUCY1A3, GUCY1B2, and GUCY1B3. Preferably, CD52, dCK, PD1, LAG3, TIM3, CTLA4, TIGIT or a combination thereof of the engineered immune cell is suppressed or silenced.

In an embodiment, the ligand binding domain binds to a target selected from the group consisting of: TSHR, CD2, CD3, CD4, CD5, CD7, CD8, CD14, CD15, CD19, CD20, CD21, CD23, CD24, CD25, CD37, CD38, CD40, CD40L, CD44, CD46, CD47, CD52, CD54, CD56, CD70, CD73, CD80, CD97, CD123, CD22, CD126, CD138, CD 179a, DR4, DR5, TAC, TEM1/CD248, VEGF, GUCY2C, EGP40, EGP-2, EGP-4, CD133, IFNAR1, DLL3, kappa light chain, TIM3, tEGFR, IL-22Ra, IL-2, ErbB3, ErbB4, MUC16, MAGE-A3, MAGE-A6, NKG2DL, BAFF-R, CD30, CD171, CS-1, CLL-1, CD33, EGFRvIII, GD2, GD3, BCMA, GPRC5D, Tn Ag, PSMA, ROR1, FLT3, FAP, TAG72, CD38, CD44v6, CEA, EPCAM, B7H3, KIT, IL-13Ra2, mesothelin, IL-11Ra, PSCA, PRSS21, VEGFR2, LewisY, CD24, PDGFR-β, SSEA-4, CD20, AFP, Folate receptor α, ERBB2 (Her2/neu), MUC1, EGFR, CS1, CD138, NCAM, Claudin18.2, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor β, TEM1/CD248, TEM7R, CLDN6, GPRC5D, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE-A4, MART-1, WT-1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGFβ, APRIL, NKG2D, and any combination thereof.

In an embodiment, the engineered immune cell is a B cell, a T cell, a macrophage, a dendritic cell, a monocyte, an NK cell, or an NKT cell. Preferably, the engineered immune cell is a T cell, for example, a CD4+/CD8+ T cell, a CD4+ helper T cell (for example, Th1 and Th2 cells), a CD8+ T cell (for example, a cytotoxic T cell), a tumor infiltrating cell, a memory T cell, a naive T cell, a γδ-T cell, and an αβ-T cell.

In one aspect, the present disclosure further provides a pharmaceutical composition, which contains the NK inhibitory molecule, the nucleic acid molecule, the vector or the engineered immune cell of the present disclosure as an active agent, and one or more pharmaceutically acceptable excipients.

In one aspect, the present disclosure further provides a method of treating a subject with cancer, infection or autoimmune disease, including administering to the subject an effective amount of the NK inhibitory molecule, the nucleic acid molecule, the vector, the engineered immune cell or the pharmaceutical composition according to the present disclosure. Therefore, the present disclosure further encompasses use of the NK inhibitory molecule, the nucleic acid molecule, the vector or the engineered immune cell in the preparation of a medicine for the treatment of cancer, infection or autoimmune disease.

In an embodiment, the cancer is a solid tumor or a hematologic tumor. More specifically, the cancer is selected from the group consisting of: brain glioma, blastoma, sarcoma, leukemia, basal cell carcinoma, biliary tract cancer, bladder cancer, bone cancer, brain and CNS cancer, breast cancer, peritoneal cancer, cervical cancer, choriocarcinoma, colon and rectal cancer, connective tissue cancer, cancer of digestive system, endometrial cancer, esophageal cancer, eye cancer, head and neck cancer, stomach cancer, glioblastoma (GBM), liver cancer, hepatoma, intraepithelial tumor, kidney cancer, larynx cancer, liver tumor, lung cancer, lymphoma, melanoma, myeloma, neuroblastoma, oral cancer, ovarian cancer, pancreatic cancer, prostate cancer, retinoblastoma, rhabdomyosarcoma, rectal cancer, cancer of respiratory system, salivary gland cancer, skin cancer, squamous cell carcinoma, stomach cancer, testicular cancer, thyroid cancer, uterine or endometrial cancer, malignant tumor of urinary system, vulval cancer and other cancer and sarcoma, and B cell lymphoma, T cell lymphoma, mantle cell lymphoma, AIDS-related lymphoma, and Waldenstrom macroglobulinemia, chronic lymphocytic leukemia (CLL), acute lymphocytic leukemia (ALL), B cell acute lymphocytic leukemia (B-ALL), T cell acute lymphocytic leukemia (T-ALL), B cell prolymphocytic leukemia, blast cell plasmacytoid dendritic cell tumor, Burkitt lymphoma, diffuse large B cell lymphoma, follicular lymphoma, chronic myelogenous leukemia (CML), malignant lymphoproliferative disorder, MALT lymphoma, hairy cell leukemia, marginal zone lymphoma, multiple myeloma, myelodysplasia, plasmablastic lymphoma, preleukemia, plasmacytoid dendritic cell tumor, and post-transplant lymphoproliferative disorder (PTLD).

In an embodiment, the infection includes, but is not limited to, infections caused by viruses, bacteria, fungi, and parasites.

In an embodiment, the autoimmune disease includes, but is not limited to, type I diabetes, celiac disease, Graves disease, inflammatory bowel disease, multiple sclerosis, psoriasis, rheumatoid arthritis, Addison disease, sicca syndrome, Hashimoto thyroiditis, myasthenia gravis, vasculitis, pernicious anemia, and systemic lupus erythematosus, etc.

The present disclosure is advantageous in that compared with expressing NK inhibitory ligands alone, the NK inhibitory molecule of the present disclosure further comprises a co-stimulatory domain, which can further reduce/inhibit the killing of engineered immune cell by the NK cell in a subject's body. Further, when the NK inhibitory molecule comprises an intracellular signaling domain, it can enhance the killing of NK cells in the subject's body by the engineered immune cell, thereby better reducing the risk of HvGD, and realizing real allogeneic transfusion.

DETAILED DESCRIPTION

Unless otherwise indicated, all scientific and technical terms used herein have the same meaning as commonly understood by those of ordinary skill in the art to which the present disclosure belongs.

NK Inhibitory Molecule

It has been reported that a cell in which expression of one or more HLA-class I molecules is reduced or eliminated may be identified as non-self by NK cells, thereby being killed in a targeted manner. Thus, expression of one or more NK inhibitory molecules on the cell can protect it from killing by the NK cells.

Therefore, in a first aspect, the present disclosure provides an NK inhibitory molecule, which contains one or more NK inhibitory ligands, transmembrane domains, and co-stimulatory domains, wherein the NK inhibitory ligands specifically bind to NK inhibitory receptors (NKIR) so as to inhibit the killing of NK cells against the engineered immune cell expressing the NK inhibitory molecule.

As used herein, the term "NK inhibitory ligand" refers to a molecule capable of binding to NKIR and inhibiting NK cell function (e.g., killing function). In an embodiment, the NK inhibitory ligand is an antibody targeting NKIR or a functional fragment thereof, or a natural ligand of NKIR or an NKIR binding fragment contained therein. Non-limiting examples of NKIR include NK cell surface receptors having or binding to an immunoreceptor tyrosine-based inhibitory motif (ITIM). Such receptors include, but are not limited to, an NKG2/CD94 component (e.g., NKG2A, NKG2B, CD94); a killer cell Ig-like receptor (KIR) family member (e.g., KIR2DL1, KIR2DL2/3, KIR2DL5A, KIR2DL5B, KIR3DL1, KIR3DL2, and KIR3DL3); a leukocyte Ig-like receptor (LIR) family member (e.g., LIR1, LIR2, LIR3, LIR5, and LIR8); an NK cell receptor protein 1 (NKR-P1) family member (e.g., NKR-P1B and NKR-P1D); an immune checkpoint receptor (e.g., PD-1, TIGIT and CD96, TIM3, LAG3); carcinoembryonic antigen-related cellular adhesion molecule 1 (CEACAM1); a sialic acid-binding immunoglobulin-like lectin (SIGLEC) family member (e.g., SIGLEC7 and SIGLEC9); a leukocyte-associated immunoglobulin-like receptor 1 (LAIR1); an Ly49 family member (e.g. Ly49A, Ly49C, Ly49F, Ly49G1, and Ly49G4), and a killer cell lectin-like receptor G1 (KLRG1).

In an embodiment, the NK inhibitory ligand is an antibody targeting NKIR or a functional fragment thereof, for example, monoclonal antibody, polyclonal antibody, recombinant antibody, human antibody, humanized antibody, murine antibody, chimeric antibody and a functional fragment thereof. Examples of antibody or functional fragments thereof include, but are not limited to, intact antibody, Fab, Fab', F(ab')2, Fv fragment, scFv antibody fragment, linear antibody, sdAb (VH or VL), nanobody (Nb), and so on, preferably selected from Fab, scFv, sdAb, and nanobody.

In an embodiment, the NK inhibitory ligand is an antibody targeting NKG2A/CD94 component or a functional fragment thereof. In a preferred embodiment, the NK inhibitory ligand is an antibody targeting NKG2A, NKG2B or CD94. NKG2/CD94 is a heterodimer composed of CD94 bound to another NKG2 subunit by a disulfide bond. The CD94 cytoplasmic domain has only seven amino acid residues, and does not have a structure for signal transmission. The NKG2 family includes members such as NKG2A, NKG2B, NKG2C, NKG2D, NKG2E, and NKG2F, wherein NKG2A and NKG2B are different spliced products of the same gene sharing a high homology. The cytoplasmic region tail of NKG2A/2B contains 2 ITIMs, and delivers inhibitory signals by recruiting SHP1 or SHP-2. The natural ligand of NKG2A/2B is HLA-E. As the binding affinity of NKG2A/2B to the ligand is higher than that of the activated receptor NKG2C, when both the inhibitory receptor and the activation receptor of NK cells can bind to target cells expressing HLA-E, inhibitory NKG2A/CD94 will dominate, and ultimately inhibit NK cell activity. NKG2A antibody known to those skilled in the art can be used in the present disclosure, e.g., Z270 (available from Immunotech, France), Z199 (available from Beckman Coulter, USA), 20D5 (available from BD Biosciences Pharmingen, USA), P25 (available from Morettaetal, Univ. Genova, Italy), etc.

In an embodiment, the NK inhibitory ligand is an antibody targeting NKG2A, which contains (1) CDR-L1 as represented by SEQ ID NO: 72, CDR-L2 as represented by SEQ ID NO: 73, CDR-L3 as represented by SEQ ID NO: 74, CDR-H1 as represented by SEQ ID NO: 75, CDR-H2 as represented by SEQ ID NO: 76, and CDR-H3 as represented by SEQ ID NO: 77, or (2) CDR-L1 as represented by SEQ ID NO: 78, CDR-L2 as represented by SEQ ID NO: 79, CDR-L3 as represented by SEQ ID NO: 80, CDR-H1 as represented by SEQ ID NO: 81, CDR-H2 as represented by SEQ ID NO: 82, and CDR-H3 as represented by SEQ ID NO: 83. In an embodiment, the NK inhibitory ligand is an antibody targeting NKG2A, which contains a light chain variable region and a heavy chain variable region, the light chain variable region has at least 70%, preferably at least 80%, more preferably at least 90%, 95%, 97% or 99% or 100% sequence identity to an amino acid sequence represented by SEQ ID NO: 3, 7 or 68, the heavy chain variable region has at least 70%, preferably at least 80%, more preferably at least 90%, 95%, 97% or 99% or 100% sequence identity to an amino acid sequence represented by SEQ ID NO: 1, 5, 67. In a preferred embodiment, the NK inhibitory ligand is an anti-NKG2A antibody containing SEQ ID NOS: 1 and 3, an anti-NKG2A antibody containing SEQ ID NOS: 5 and 7 or an anti-NKG2A antibody containing SEQ ID NOS: 67 and 68.

In an embodiment, the NK inhibitory ligand is an antibody targeting KIR or a functional fragment thereof. The KIR molecule is a type I transmembrane protein, and belongs to the immunoglobulin superfamily, and the structure thereof includes an extracellular region, a transmembrane region, and a cytoplasmic region. According to the number of Ig-like domains contained in the extracellular region, KIR can be divided into KIR2D and KIR3D subfamilies. According to the length of cytoplasmic region, KIR further may be divided into long forms (L) and short forms (S), such as KIR2DL, KIR2DS, KIR3DL, and KIR3DS. In the above, the cytoplasmic region of KIR2DL1, KIR2DL2, KIR2DL3, KIR3DL1, KIR3DL2, and KIR3DL3 contains two immunoreceptor tyrosine-based inhibitory motifs (ITIM), and the cytoplasmic region of KIR2DL5 contains one ITIM, and they are inhibitory KIR receptors. Specifically, the phosphorylation of ITIM contained in the cytoplasmic region of the inhibitory KIR receptor is phosphorylated will recruit the phosphatases SHP1 and SHP2, causing dephosphorylation of the cellular substrate, and finally inhibiting or terminating the effector functions of NK cells, such as cytotoxicity and cytokine secretion. KIR is expressed on most of NK cells, although there are differences in expression levels in different individuals. Even in the same individual, types of KIRs expressed by different NK cells are not all the same, and the same NK cell can express several different KIR molecules. Recognition ligands of KIR are classical HLA-class I molecules, including certain polymorphic epitopes of HLA-A, HLA-B, and HLA-C. For example, KIR3DL2 recognizes HLA-A alleles-A3 and -A11, KIR3DL1 recognizes HLA-Bw-4, KIR2DL1 recognizes HLA-Cw2, HLA-Cw4, and HLA-Cw6 isoforms. The mouse homologue of KIR is gp49B1, which is 335 amino acids in length, and contains 2 ITIM structures in the cytoplasmic region. In a preferred embodiment, the antibody targeting KIR is an antibody targeting one or more targets selected from the group consisting of: KIR2DL1, KIR2DL2, KIR2DL3, KIR3DL1, KIR3DL2, KIR3DL3, KIR2DL5, and gp49B1. KIR antibodies that are well known to those skilled in the art can be used in the present disclosure, e.g., GL183 (targeting KIR2DL2/L3, available from Immunotech, France and Beckton Dickinson, USA), EB6 (targeting KIR2DL1, available from Immunotech, France, and Beckton Dickinson, USA), AZ138 (targeting KIR3DL1, available from Morettaetal, Univ. Genova, Italy), Q66 (targeting KIR3DL2, available from Immunotech, France), Z27 (targeting KIR3DL1, available from Immunotech, France and Beckton Dickinson, USA), etc.

In an embodiment, the NK inhibitory ligand is an antibody targeting KIR, which comprises CDR-L1 as represented by SEQ ID NO: 84, CDR-L2 as represented by SEQ ID NO: 85, CDR-L3 as represented by SEQ ID NO: 86, CDR-H1 as represented by SEQ ID NO: 87, CDR-H2 as represented by SEQ ID NO: 88, and CDR-H3 as represented by SEQ ID NO: 89. In an embodiment, the NK inhibitory ligand is an antibody targeting KIR, which comprises a light chain variable region and a heavy chain variable region, the light chain variable region has at least 70%, preferably at least 80%, more preferably at least 90%, 95%, 97% or 99% or 100% sequence identity to an amino acid sequence represented by SEQ ID NO: 58, and the heavy chain variable region has at least 70%, preferably at least 80%, more preferably at least 90%, 95%, 97% or 99% or 100% sequence identity to an amino acid sequence represented by SEQ ID NO: 59. In a preferred embodiment, the NK inhibitory ligand is an anti-KIR antibody comprising SEQ ID NO: 58 and SEQ ID NO: 59, and an amino acid sequence thereof is, for example, as represented by SEQ ID NO: 57 or 60.

In an embodiment, the NK inhibitory ligand is an antibody targeting LIR or a functional fragment thereof. LIR is also known as immunoglobulin-like transcripts (ILT) or monocyte-macrophage inhibitory receptor (MIR). The LIR family has 8 members, in which the cytoplasmic regions of LIR1 (also referred to as ILT2), LIR2 (also referred to as ILT4), LIR3 (also referred to as ILT5), LIR5 (also referred to as ILT3), and LIR8 contain 2-4 ITIM structures, among which at least one is a VXYXXL/V motif, and they are inhibitory LIR receptors. LIR-1 has been reported to be capable of inhibiting the killing of NK cell line NKL against target cell expressing HLA-class I molecules and the activation of NKL mediated by CD16. Homologue of LIR in mice is PIR (Paired Ig-like receptor), including PIR-A and PIR-B, in which PIR-A transmits activation signals with the aid of FcRγ homodimer, while PIR-B transmits inhibition signals through four ITIM structures contained in the cytoplasmic region thereof. In a preferred embodiment, the NK inhibitory ligand is an antibody targeting LIR1, LIR2, LIR3, LIR5, LIR8 or PIR-B.

In an embodiment, the NK inhibitory ligand is an antibody targeting LIR1, which comprises (1) CDR-L1 as represented by SEQ ID NO: 90, CDR-L2 as represented by SEQ ID NO: 91, CDR-L3 as represented by SEQ ID NO: 92, CDR-H1 as represented by SEQ ID NO: 93, CDR-H2 as represented by SEQ ID NO: 94, and CDR-H3 as represented by SEQ ID NO: 95, or (2) CDR-L1 as represented by SEQ ID NO: 96, CDR-L2 as represented by SEQ ID NO: 97, CDR-L3 as represented by SEQ ID NO: 98, CDR-H1 as represented by SEQ ID NO: 99, CDR-H2 as represented by SEQ ID NO: 100, and CDR-H3 as represented by SEQ ID NO: 101. In an embodiment, the NK inhibitory ligand is an antibody targeting LIR1, which comprises a light chain variable region and a heavy chain variable region, the light chain variable region has at least 70%, preferably at least 80%, more preferably at least 90%, 95%, 97% or 99% or 100% sequence identity to an amino acid sequence represented by SEQ ID NO: 61 or 65, and the heavy chain variable region has at least 70%, preferably at least 80%, more preferably at least 90%, 95%, 97% or 99% or 100% sequence identity to an amino acid sequence represented by SEQ ID NO: 62 or 64. In a preferred embodiment, the NK inhibitory ligand is an anti-LIR1 antibody having an amino acid sequence as represented by SEQ ID NO: 63 or 66. Other antibodies targeting the LIR family members known in the art can also be used in the present disclosure. In an embodiment, the NK inhibitory ligand is an antibody targeting an immune checkpoint receptor (e.g. PD-1, TIGIT, CD96, TIM3, and LAG3) or a functional fragment thereof. In a preferred embodiment, the NK inhibitory ligand is an antibody targeting PD-1 or a functional fragment thereof. PD-1 is mainly expressed in activated NK cells. It belongs to the CD28 family member, and is a type I transmembrane glycoprotein consisting of 268 amino acids. Its structure mainly includes an extracellular immunoglobulin variable domain (IgV)-like structure, a hydrophobic transmembrane region, and an intracellular region. The tail of the intracellular region has two independent tyrosine residues, wherein the tyrosine residue at the nitrogen end participates in constituting an ITIM, and the tyrosine residue at the carbon end participates in constituting an immunoreceptor tyrosine based switch motif (ITSM). PD-1 binding to its ligands (such as PD-L1 and PD-L2) promotes tyrosine in the ITSM domain of PD-1 to be phosphorylated, and further cause dephosphorylation of downstream protein kinases Syk and PI3K, and inhibition of activation of downstream AKT, ERK, and other pathways, and finally inhibit the activity of NK.

In a preferred embodiment, the NK inhibitory ligand is an antibody targeting TIGIT or a functional fragment thereof. TIGIT belongs to the immunoglobulin superfamily member, and it consists of an extracellular immunoglobulin variable region (IgV) domain, a type 1 transmembrane domain, and an intracellular domain with ITIM and immunoglobulin tyrosine tail (ITT) motif. Upon binding to a ligand (e.g., CD155, CD112, CD113), the transmission of intracellular inhibitory signal may be induced, thereby inhibiting the activity of NK cells.

In a preferred embodiment, the NK inhibitory ligand is an antibody targeting LAG3 or a functional fragment thereof. LAG3 is a member of the protein Ig superfamily. It is a type 1 transmembrane protein expressed on activated T cell, NK cell, B cell, and plasmacytoid dendritic cell. The four IgG domains of LAG3 have high structural homology to the CD4 molecule, but homology of their amino acids is lower than 20%. Studies have shown that LAG3 has a negative regulatory effect on proliferation and long-term memory of T cells and NK cells. Once activated by its ligands (e.g., FGL1), it can promote "bad cells" such as tumor cells to escape from the killing of the immune system.

In a preferred embodiment, the NK inhibitory ligand is an antibody targeting TIM3 or a functional fragment thereof. TIM3 is a receptor protein of the TIM family, and is expressed on the surface of T cell, Treg cell, innate immune cell (dendritic cell, natural killer cell, and monocyte). The TIM family members are encoded by three genes, specifically, HAVCR1 encodes TIM1, HAVCR2 encodes TIM3, and TIMD4 encodes TIM4. TIM3 has multiple ligands, such as phosphatidylserine, galectin-9 (Gal-9), HMGB1, and CEACAM-1. When expressed in NK cells, TIM3 is considered as a possible marker for dysfunctional NK cells, and TIM3 blockade has been proved to be able to reverse NK cell dysfunction.

In an embodiment, the NK inhibitory ligand is an antibody targeting NKR-P1 or a functional fragment thereof. NKR-P1 is a type II transmembrane glycoprotein, and expressed in all human, mouse, and rat NK cells. At present, six NKR-P1 members of mice, i.e. NKR-P1A, NKR-P1B, NKR-P1C, NKR-P1D, NKR-P1E, and NKR-P1F, respectively, have been found, while only NKR-P1A (also referred to as CD161) is found inhuman body. The extracellular region of the NKR-P1 molecule is an NK receptor domain (NKD) in a C-type lectin-like superfamily, and is structurally similar to Ly49, Cd69, and CD94/NKG2 molecules. Although NKR-P1 is primarily present in a form of homodimer, human NKR-P1A may exist in a monomer form. The cytoplasmic regions of the NKR-P1 family molecules are structurally different among different species, for example, the cytoplasmic regions of NKR-P1B and NKR-P1D contain an ITIM motif, which recruits SHP-1 to transmit inhibitory signals after tyrosine phosphorylation, but NKR-P1C binds to the Fc receptor through a positively charged amino acid in the transmembrane region, and then recruits Syk to transmit an activation signal. Therefore, in a preferred embodiment, the NK inhibitory ligand is an antibody targeting NKR-P1B or NKR-P1D.

In an embodiment, the NK inhibitory ligand is an antibody targeting CEACAM1 or a functional fragment thereof. CEACAM1, also known as CD66a, bile glycoprotein (BGP) or C-CAM1, is a member of the carcinoembryonic antigen (CEA) gene family and belongs to the immunoglobulin (Ig) superfamily. In activated NK cells, CEACAM1 expression is up-regulated, and its homophilic interaction causes inhibition of lymphocyte toxicity effect. CEACAM1 interacts with other known CEACAM proteins including CD66a (CEACAM1), CD66c (CEACAM6), and CD66e (CEACAM5, CEA) proteins. In human, 11 different CEACAM1 splice variants have been detected to date. The designation of CEACAM1 isotype is related to the number of extracellular immunoglobulin-like domains (e.g., CEACAM1 with 4 extracellular immunoglobulin-like domains is referred to as CEACAM1-4), and the length of the cytoplasmic tail (e.g., CEACAM1-4 with a long cytoplasmic tail is referred to as CEACAM1-4L, and CEACAM11-4 with a short cytoplasmic tail is referred to as CEACAM1-4S). The N-terminal domain of CEACAM1 begins immediately after a signal peptide, and its structure is considered as an IgV-type.

In an embodiment, the NK inhibitory ligand is an antibody targeting SIGLEC or a functional fragment thereof. 16 SIGLEC proteins have been identified in human and 9 SIGLEC proteins have been identified in mice, wherein the SIGLEC proteins consist of 2-17 extracellular Ig domains including amino-terminal V-type domains comprising a sialic acid binding site. Siglecs are typically divided into two groups: a first subset consisting of Siglec1, Siglec2, Siglec4, and Siglec15, and a CD33-related second subset including Siglec3, Siglec5, Siglec6, Siglec7, Siglec8, Siglec9, Siglec10, Siglec11, Siglec12, Siglec14, and Siglec16. Siglec7, also known as p75, CD328 or AIRM, comprises an extracellular N-terminal Ig-like V-type domain, two Ig-like C2-type domains, and an intracellular region containing one ITIM motif and one ITIM-like motif Siglec7 is constitutively expressed on NK cells, dendritic cells, monocytes, and neutrophils. Siglec7 has been observed to have an inhibitory effect on NK cell-mediated tumor clearance. The structure of Siglec9 is quite similar to Siglec7, their N-terminal V-group Ig domains have overall amino acid sequence identity of about 77%, and show different sialic acid binding specificities. In view of functional studies on NK cells, tumor cells expressing Siglec9-binding sialic acid ligand have been proved to inhibit NK cell activation and tumor cell killing. Many human tumors robustly up-regulate sialic acid ligand that binds to Siglec9, which allows the tumors to be capable of escaping immunity and then cancer progression occurs.

In a preferred embodiment, the NK inhibitory ligand is an antibody targeting Siglec7 or Siglec9, such as those known in the art. By way of example, an anti-Siglec7 antibody may be derived from human Siglec7/CD328 antibody (AF1138, R&D Systems), clone #194212 (MAB1138, R&D Systems), clone #194211 (MAB11381, R&D Systems), clone Z176 (A22330, Beckman Coulter), 6-434 (339202, Biolegend), REA214 (Miltenyl Biotec), S7.7 (MCA5782GA, BioRad), 10B2201 (MBS604764, MyBioSource), 8D8 (MBS690562, MyBioSource), 10B2202 (MBS608694, MyBioSource), and 5-386 (MBS214370, MyBioSource). The anti-Siglec9 antibody can be derived from MAB1139 (clone #191240, R&D Systems), AF1139 (R&D Systems), D18 (SC-34936, Santa Cruz Biotechnology), Y-12SC34938 (SC3-4938, Santa Cruz Biotechnology), AB 197981 (Abeam), AB96545 (Abeam), AB89484 (clone #MM0552-6K12, Abeam), AB 130493 (Abeam), AB117859 (clone #3G8, Abeam), E10-286 (Becton Dickinson). Given the similarity in extracellular structure of Siglec7 and Siglec9, antibodies that simultaneously target the two may also act as a NK inhibitory ligand of the present disclosure.

In an embodiment, the NK inhibitory ligand is an antibody targeting SIGLEC7, SIGLEC9 or both, which comprises (1) CDR-L1 as represented by SEQ ID NO: 102, CDR-L2 as represented by SEQ ID NO: 103, CDR-L3 as represented by SEQ ID NO: 104, CDR-H1 as represented by SEQ ID NO: 105, CDR-H2 as represented by SEQ ID NO: 106, and CDR-H3 as represented by SEQ ID NO: 107, (2) CDR-L1 as represented by SEQ ID NO: 122, CDR-L2 as represented by SEQ ID NO: 123, CDR-L3 as represented by SEQ ID NO: 124, CDR-H1 as represented by SEQ ID NO: 125, CDR-H2 as represented by SEQ ID NO: 126 and CDR-H3 as represented by SEQ ID NO: 127, (3) CDR-L1 as represented by SEQ ID NO: 131, CDR-L2 as represented by SEQ ID NO: 132, CDR-L3 as represented by SEQ ID NO: 133, CDR-H1 as represented by SEQ ID NO: 134, CDR-H2 as represented by SEQ ID NO: 135 and CDR-H3 as represented by SEQ ID NO: 136, (4) CDR-L1 as represented by SEQ ID NO: 140, CDR-L2 as represented by SEQ ID NO: 141, CDR-L3 as represented by SEQ ID NO: 142, CDR-H1 as represented by SEQ ID NO: 143, CDR-H2 as represented by SEQ ID NO: 144, and CDR-H3 as represented by SEQ ID NO: 155, (5) CDR-L1 as represented by SEQ ID NO: 176, CDR-L2 as represented by SEQ ID NO: 177, CDR-L3 as represented by SEQ ID NO: 178, CDR-H1 as represented by SEQ ID NO: 179, CDR-H2 as represented by SEQ ID NO: 180 and CDR-H3 as represented by SEQ ID NO: 181, or (6) CDR-L1 as represented by SEQ ID NO: 188, CDR-L2 as represented by SEQ ID NO: 189, CDR-L3 as represented by SEQ ID NO: 190, CDR-H1 as represented by SEQ ID NO: 191, CDR-H2 as represented by SEQ ID NO: 192, and CDR-H3 as represented by SEQ ID NO: 193. The above antibodies (1)-(4) target SIGLEC7, and antibodies (5)-(6) simultaneously target both SIGLEC7 and SIGLEC9. In an embodiment, the NK inhibitory ligand is an antibody targeting SIGLEC7, SIGLEC9 or both, which comprises a light chain variable region and a heavy chain variable region, the light chain variable region has at least 70%, preferably at least 80%, more preferably at least 90%, 95%, 97% or 99% or 100% sequence identity to an amino acid sequence represented by SEQ ID NO: 108, 128, 137, 146, 182, 185 or 194, and the heavy chain variable region has at least 70%, preferably at least 80%, more preferably at least 90%, 95%, 97% or 99% or 100% sequence identity to an amino acid sequence represented by SEQ ID NO: 109, 129, 138, 147, 183, 186 or 195. In a preferred embodiment, the NK inhibitory ligand is an antibody against SIGLEC7, SIGLEC9 or both, whose amino acid sequence is as represented by SEQ ID NO: 110, 130, 139, 148, 184, 187 or 196. In an embodiment, the NK inhibitory ligand is an antibody targeting LAIR1 or a functional fragment thereof. LAIR1 contains 10 exons, encoding a type I transmembrane glycoprotein consisting of 287 amino acids, which contains a single extracellular type C2 Ig-like domain, followed by a stem region linked to a single transmembrane domain and two ITIM motifs transmitting inhibitory signals. LAIR1 has certain structural homology to LIR and KIR family members, indicating that these molecules may be derived from the same progenitor gene. LAIR1 is expressed in T cell, B cell, natural killer (NK) cell, macrophage, and dendritic cell, and hematopoietic progenitor cell including human CD34+ cells. Due to the presence of the ITIM motif, studies in human and mice have so far found that LAIR1 plays a role in immunosuppression. Further studies show that LAIR1 not only can inhibit static NK cells, but also can inhibit the killing of activated NK cells against target cells.

In an embodiment, the NK inhibitory ligand is an antibody targeting Ly49 or a functional fragment thereof. Ly49 is a type II transmembrane glycoprotein, can form a homodimer by linkage of disulfide bond, and exerts a function similar to that of human KIR, i.e. transmitting a signal by interacting with MHC-class I molecular ligand, further adjusting the activity of NK cells. The Ly49 family of mice has been found to include 11 members, i.e. Ly49A, Ly49B, Ly49C, Ly49D, Ly49E, Ly49F, Ly49G, Ly49H, Ly49I, Ly49P, and Ly49Q. In the above, Ly49A, Ly49C, Ly49F, Ly49G, and Ly49Q all contain an ITIM motif in the cytoplasmic region, can bind to and activate the tyrosine kinase SHP-1, and inhibit the activation of NK cells by interfering with the production of phosphorylated tyrosine. Therefore, in a preferred embodiment, the NK inhibitory ligand is an antibody targeting Ly49A, Ly49C, Ly49F, Ly49G or Ly49Q.

In an embodiment, the NK inhibitory ligand is an antibody targeting KLRG1 or a functional fragment thereof. KLRG1 is a type II transmembrane protein surface co-inhibitory receptor that modulates the activity of T cells and NK cells. The extracellular portion thereof comprises a C-type lectin domain, and the known ligand is cadherin, and an intracellular portion thereof comprises an immunoreceptor tyrosine-based inhibitory motif (ITIM) domain. It has been reported that KLRG1 receptor expression on peripheral blood NK cells of hepatitis C patients will promote the reduction of the number of NK cells and function damage, and a mechanism thereof is mainly to inhibit the proliferation of NK cells, promote the apoptosis of NK cells, and reduce the release of inflammatory cytokines of NK cells.

In an embodiment, the NK inhibitory ligand is an antibody targeting KLRG1, which comprises: (1) CDR-L1 as represented by SEQ ID NO: 111, CDR-L2 as represented by SEQ ID NO: 112, CDR-L3 as represented by SEQ ID NO: 113, CDR-H1 as represented by SEQ ID NO: 114, CDR-H2 as represented by SEQ ID NO: 115, and CDR-H3 as represented by SEQ ID NO: 116, (2) CDR-L1 as represented by SEQ ID NO: 149, CDR-L2 as represented by SEQ ID NO: 150, CDR-L3 as represented by SEQ ID NO: 151, CDR-H1 as represented by SEQ ID NO: 152, CDR-H2 as represented by SEQ ID NO: 153 and CDR-H3 as represented by SEQ ID NO: 154, (3) CDR-L1 as represented by SEQ ID NO: 158, CDR-L2 as represented by SEQ ID NO: 159, CDR-L3 as represented by SEQ ID NO: 160, CDR-H1 as represented by SEQ ID NO: 161, CDR-H2 as represented by SEQ ID NO: 162, and CDR-H3 as represented by SEQ ID NO: 163, or (4) CDR-L1 as represented by SEQ ID NO: 167, CDR-L2 as represented by SEQ ID NO: 168, CDR-L3 as represented by SEQ ID NO: 169, CDR-H1 as represented by SEQ ID NO: 170, CDR-H2 as represented by SEQ ID NO: 171, and CDR-H3 as represented by SEQ ID NO: 172. In an embodiment, the NK inhibitory ligand is an antibody targeting KLRG1, which comprises a light chain variable region and a heavy chain variable region, the light chain variable region has at least 70%, preferably at least 80%, more preferably at least 90%, 95%, 97% or 99% or 100% sequence identity to an amino acid sequence represented by SEQ ID NO: 117, 155, 164 or 173, and the heavy chain variable region has at least 70%, preferably at least 80%, more preferably at least 90%, 95%, 97% or 99% or 100% sequence identity to an amino acid sequence represented by SEQ ID NO: 118, 156, 165 or 174. In a preferred embodiment, the NK inhibitory ligand is an anti-KLRG1 antibody having an amino acid sequence represented by SEQ ID NO: 119, 157, 166 or 175.

In an embodiment, the NK inhibitory ligand is an NKIR natural ligand or an NKIR binding region (e.g., an extracellular region) contained therein, and such natural ligands include, but are not limited to, non-classical HLA-class I molecule (e.g., HLA-E, HLA-F, and HLA-G), cadherin, collagen, OCIL, sialic acid, immune checkpoint ligands (e.g., PD-L1/PD-L2, CD155, CD112, CD113, Gal-9, FGL1), and so on.

In an embodiment, the NK inhibitory ligand is a non-classical HLA-class I molecule or an extracellular region thereof, more preferably α1 and α2 domains of non-classical HLA-class I molecule. The non-classical HLA-class I molecule is located in the same chromosomal region 6p21.3, short arm of chromosome 6, consisting of a heavy chain (α chain) and a light chain (β chain, encoded by B2M gene) linked by a non-covalent bond. The α chain includes three parts, i.e. an extracellular region (including three domains α1, α2, and α3), a transmembrane domain, and a cytoplasmic region, wherein α1 and α2 form an antigen binding groove that is responsible for binding to an antigen peptide entering the groove. α3 is homologous to the constant domain of an immunoglobulin, and binds to T cell surface molecule CD8. Non-classical HLA-class I molecules include three members: HLA-E, HLA-F, and HLA-G. HLA-E regulates NK cell activity by binding to CD94/NKG2 receptors on the surface of NK cells. The function of HLA-E is to bind peptides derived from a leader sequence of HLA class I molecules (HLA-A, -B, -C, and -G), and present them to NK cells through interaction with inhibitory receptor CD94/NKG2A, thus inhibiting the lysis of cells expressing normal levels of HLA class I molecules by NK cells. Since the affinity of HLA-E to the inhibitory receptor CD94/NKG2A under physiological conditions is significantly higher than its affinity to an activating receptor CD94/NKG2C, up-regulation of the expression level of HLA-E may protect target cells from the killing effect of NK cells. HLA-F can bind to NK inhibitory receptors ILT2 and ILT4, and such binding can be effectively inhibited by ILT2 and ILT4 antibodies. HLA-F function is still being explored at present, but it is speculated that its binding to ILT2 and ILT4 may have immunosuppressive effect. HLA-G can recognize various NK inhibitory receptors, such as CD94/NKG2A, LIR-1, LIR-2, KIR2DL1, etc. It is found that HLA-G molecules on the surface of fetal cell may inhibit NK cell killing activity by binding to KIR on the surface of a parent NK cell, thereby causing the parent to be immune-tolerant to an HLA semi-heterologous fetus. In addition, HLA-G molecules highly expressed on the cell surface of solid tumors, such as melanoma, sarcoma, and lymphoma, also enable tumor cells to escape the killing, and lysis effects of NK cells.

In an embodiment, the NK inhibitory ligand is an HLA-E extracellular region, which has at least 70%, preferably at least 80%, and more preferably at least 90%, 95%, 97% or 99% or 100% sequence identity to an amino acid sequence represented by SEQ ID NO: 31 or an encoding sequence thereof has at least 70%, preferably at least 80%, and more preferably at least 90%, 95%, 97% or 99% or 100% sequence identity to a nucleotide sequence represented by SEQ ID NO: 32. In another embodiment, the NK inhibitory ligand is a mutant of the HLA-E extracellular region (containing Y84C mutation), which has at least 70%, preferably at least 80%, more preferably at least 90%, 95%, 97% or 99% or 100% sequence identity to an amino acid sequence represented by SEQ ID NO: 33, or an encoding sequence thereof has at least 70%, preferably at least 80%, more preferably at least 90%, 95%, 97% or 99% or 100% sequence identity to a nucleotide sequence represented by SEQ ID NO: 34.

In an embodiment, the NK inhibitory ligand is an HLA-G extracellular region, which has at least 70%, preferably at least 80%, and more preferably at least 90%, 95%, 97% or 99% or 100% sequence identity to an amino acid sequence represented by SEQ ID NO: 35, or an encoding sequence thereof has at least 70%, preferably at least 80%, and more preferably at least 90%, 95%, 97% or 99% or 100% sequence identity to a nucleotide sequence represented by SEQ ID NO: 36.

In an embodiment, when it is desired to knock out the endogenous B2M of the engineered immune cell and express non-classical HLA-class I molecule as NK inhibitory ligand, synonymously mutated (i.e., only the nucleotide sequence is changed while the amino acid sequence is not changed) B2M gene needs to be introduced to allow it to form complexes with non-classical HLA-class I molecules to exert inhibiting functions, meanwhile synonymously mutated B2M gene also can be protected against knockout by a gene editing tool targeting endogenous B2M. In this embodiment, the NK inhibitory ligand comprises a fusion molecule of B2M and the extracellular region of a non-classical HLA-class I molecule. For example, the NK inhibitory ligand comprises a fusion molecule of B2M and HLA-E extracellular region or HLA-G extracellular region. In a specific embodiment, the NK inhibitory ligand comprises a fusion molecule of B2M and HLA-E extracellular region, and preferably, the HLA-E extracellular region contains Y84C mutation (SEQ ID NO: 33). In a preferred embodiment, the NK inhibitory ligand comprises a presenting peptide and a fusion molecule of B2M and HLA-E extracellular region, wherein the presenting peptide is selected from SEQ ID NOS: 46-53. Methods for synonymously mutating B2M gene are well known to those skilled in the art. In a preferred embodiment, B2M has at least 70%, preferably at least 80%, more preferably at least 90%, 95%, 97% or 99% or 100% sequence identity to an amino acid sequence represented by SEQ ID NO: 37; and the nucleotide sequence of the synonymously mutated B2M gene is, for example, represented by SEQ ID NO: 38.

In an embodiment, the NK inhibitory ligand is Osteoclast inhibitory lectin (OCIL) or an NKIR binding region thereof. Mouse OCIL includes three members: OCIL (also known as Clr-b), OCILrP1 (also known as Clr-d), and mOCILrP2 (also known as Clr-g). OCIL is widely expressed in various tissues, and the expression pattern thereof is similar to that of MHC-class I molecules. OCIL is a ligand of NKR-P1B/D. Studies have shown that expressing OCIL on tumor cells can inhibit the killing effect of NK cells against tumor cells, and OCIL-specific antibodies can reverse such inhibitory effect.

In an embodiment, the NK inhibitory ligand is cadherin or an extracellular region thereof, for example, E-cadherin (E-cad), N-cadherin (N-cad) or R-cadherin (R-cad), preferably an extracellular region of E-cadherin. Cadherins are a class of calcium-dependent transmembrane proteins that mainly mediate homogeneous intercellular adhesion, and bind to the NK inhibitory receptor KLRG1. The cadherin molecule is a type I membrane protein, consists of about 723-748 amino acids, and structurally includes an extracellular region responsible for binding ligand, a transmembrane region, and a highly conserved cytoplasmic region. The extracellular region has several cadherin repeat domains (EC), and contains repetitive sequences consisting of 4-5 amino acid residues, responsible for binding to ligands. Human E-cadherin is encoded by CDH 1 gene, and is currently the most studied member of the cadherin family. Therefore, in a preferred embodiment, the NK inhibitory ligand is an extracellular region of E-cadherin comprising EC1 and EC2. More preferably, the NK inhibitory ligand is an extracellular region of E-cadherin comprising EC1, EC2, EC3, EC4, and EC5. More preferably, the NK inhibitory ligand is E-Cad, which has at least 70%, preferably at least 80%, and more preferably at least 90%, 95%, 97% or 99% or 100% sequence identity to an amino acid sequence represented by SEQ ID NO: 39 or 41 or an encoding sequence thereof has at least 70%, preferably at least 80%, and more preferably at least 90%, 95%, 97% or 99% or 100% sequence identity to a nucleotide sequence represented by SEQ ID NO: 40 or 42.

In an embodiment, the NK inhibitory ligand is a collagen or an NKIR binding region thereof, and it binds to LAIR 1. Collagen molecule is a trimer consisting of 3 α chains, each α chain containing a (glycine-proline-hydroxyproline)n repetitive sequences. LAIR1 recognizes and interacts with the Gly-Pro-Hyp repetitive sequence. Due to the extensive presence of this repetitive sequence, it has been shown that LAIR1 can extensively bind to a variety of collagen molecules, including but not limited to transmembrane collagens, such as collagens XVII, XIII, and XXIII; and non-transmembrane collagens, such as collagen I, II, and III. Tumor cells or tumor interstitial cells often highly express a variety of collagen molecules, which may transmit inhibitory signals into immune cells by binding to the inhibitory receptor LAIR1 on the surface of immune cells, thereby achieving the purpose of immune escape.

In an embodiment, the NK inhibitory ligand is sialic acid or an NKIR binding region thereof, and it binds to an SIGLEC family member (e.g., SIGLEC7 and/or SIGLEC9). Sialic acid is an important component of the innate immune system of vertebrates, and NK cell killing activity is associated with sialylation of the surface of tumor cells. Sialylation of tumor cells not only can hinder the physical action between tumor cells and NK cells, but also can shield the activating ligands, at the surface of the tumor cells, capable of binding thereto. In addition, sialylation of the surface of the tumor cell may block the formation of immune synapses between tumor cells and NK cells, thus reducing the killing toxicity of the NK cells against the tumor. Studies have found that sialylation of the surface of tumor cells also can inhibit the killing activity of NK cells by triggering an immunosuppressive signal mediated by Siglec. Siglec7 is expressed on the surface of most of NK cells, and when sialic acid linked with α-2,8 glycosidic bonds on the surface of tumor cells binds to Siglec7 on the surface of NK cells, the activation of NK cells is inhibited, so that the tumor cells escape the killing function mediated by NK cells.

In an embodiment, the NK inhibitory ligand is PD-L1/PD-L2 or an extracellular region thereof, and it binds PD1. PD-L1 is constitutively low-expressed on antigen presenting cell (APC), and non-hematopoietic cell such as vascular endothelial cell, islet cell, and immune privilege site (such as placenta, testis, and eye). Inflammatory cytokines such as type I, and type II interferons, TNF-α, and VEGF can induce expression of PD-L1. PD-L2 is expressed only in activated macrophages and dendritic cells. Tumor cells themselves can up-regulate the expression of PD-L1, while inflammatory factors in the tumor microenvironment can also induce the expression of PD-L1 and PDL2. Up-regulated expression of PD-L1 and PD-L2 on the surface of tumor cells can trigger the transmission of immunosuppressive signals mediated by PD-1 so as to inhibit the killing activity of NK cells. In a preferred embodiment, the NK inhibitory ligand is a PD-L1 extracellular region or a PD-L2 extracellular region, which has at least 70%, preferably at least 80%, more preferably at least 90%, 95%, 97% or 99% or 100% sequence identity to an amino acid sequence represented by SEQ ID NO: 70 or 71.

In an embodiment, the NK inhibitory ligand is CD155, CD112 or CD113 or an NKIR binding region thereof, all of which bind to TIGIT. CD155 is a high affinity ligand of TIGIT. Once CD155 highly expressed on the tumor surface binds to TIGIT on the NK surface, the killing effect of NK cells against tumor cells is inhibited. CD112 and CD113 also bind to TIGIT, although the affinity is relatively weak.

In an embodiment, the NK inhibitory ligand is galectin 9 (also known as Gal-9) or an NKIR binding region thereof, and it binds to TIM3. Gal-9 is a C type lectin that is widely expressed and secreted by many hematopoietic cells, and can bind to carbohydrate moieties on cell surface proteins. On TIM3, Gal-9 binds to a carbohydrate motif on its IgV domain, and induce calcium influx and cell death of TIM3 positive NK cells. There have been a large number of proofs showing that TIM3/Gal-9 interaction plays a role in inhibiting the immune response.

In an embodiment, the NK inhibitory ligand is FGL1 or an NKIR binding region thereof, and it binds to LAG3. FGL1 belongs to the fibrinogen family, and is a newly found ligand of LAG3, but it does not have domains such as characteristic platelet binding site and thrombin sensitive site. FGL1 protein is mainly distributed in tumor cells, and tumor stromal expression is relatively low. FGL1/LAG3 interaction is another tumor immunity escape pathway independent of the B7-H1/PD-1 pathway, and blocking this pathway can achieve a synergistic effect with PD-1 pathway blockade.

As used herein, the term "transmembrane domain" refers to a polypeptide structure that enables expression of a chimeric antigen receptor on the surface of an immune cell (e.g., a lymphocyte or an NKT cell), and guides the cellular response of the immune cell against the target cell. The transmembrane domain may be natural or synthetic, and also may be derived from any membrane-bound protein or transmembrane protein. When the chimeric antigen receptor binds to the target antigen, the transmembrane domain is capable of signaling. The transmembrane domains particularly suitable for use in the present disclosure may be derived from, for example, TCR α chain, TCR β chain, TCR γ chain, TCR δ chain, CD3 ζ subunit, CD3 ε subunit, CD3 γ subunit, CD3 δ subunit, CD45, CD4, CD5, CD8 α, CD9, CD16, CD22, CD33, CD28, CD37, CD64, CD80, CD86, CD134, CD137, CD154, and a transmembrane domain of an NKIR natural ligand, such as non-classical HLA-class I molecule (such as HLA-E, HLA-F, and HLA-G), cadherin, collagen, and OCIL. Preferably, the transmembrane domain is selected from a transmembrane domain of CD8 α, CD4, CD28, and CD278. Alternatively, the transmembrane domain may be synthesized and may mainly contain a hydrophobic residue such as leucine and valine. Preferably, the transmembrane domain is derived from CD8 α or CD28, and more preferably has at least 70%, preferably at least 80%, more preferably at least 90%, 95%, 97% or 99% or 100% sequence identity to an amino acid sequence represented by SEQ ID NO: 9 or 11, or an encoding sequence of the transmembrane domain has at least 70%, preferably at least 80%, more preferably at least 90%, 95%, 97% or 99% or 100% sequence identity to a nucleotide sequence represented by SEQ ID NO: 10 or 12.

In an embodiment, the NK inhibitory molecule of the present disclosure further may contains a hinge region located between the NK inhibitory ligand and the transmembrane domain. As used herein, the term "hinge region" generally refers to any oligopeptide or polypeptide that functions to link a transmembrane domain to a ligand binding domain. Specifically, the hinge region serves to provide greater flexibility and accessibility to the ligand binding domain. The hinge region may contain up to 300 amino acids, preferably 10 to 100 amino acids and most preferably 25 to 50 amino acids. The hinge region may be completely or partially derived from a natural molecule, for example, completely or partially from the extracellular region of CD8, CD4 or CD28, or completely or partially from an antibody constant region. Alternatively, the hinge region may be a synthetic sequence corresponding to a naturally occurring hinge sequence or may be a completely synthetic hinge sequence. In a preferred embodiment, the hinge region contains a hinge region portion of CD8 α, CD28, Fc γ RIII α receptor, IgG4 or IgG1, more preferably CD8 α, CD28 or IgG4 hinge, which has at least 70%, preferably at least 80%, more preferably at least 90%, 95%, 97% or 99% or 100% sequence identity to an amino acid sequence represented by SEQ ID NO: 25, 27 or 29, or an encoding sequence of the CD28 hinge has at least 70%, preferably at least 80%, more preferably at least 90%, 95%, 97% or 99% or 100% sequence identity to a nucleotide sequence represented by SEQ ID NO: 26, 28 or 30.

The NK inhibitory molecule of the present disclosure includes a co-stimulatory domain. Therefore, when the NK inhibitory ligand binds to an NKIR, on one hand, an inhibitory signal can be transmitted to the NK cell through the signaling region of the NKIR, so as to reduce the killing thereof against the target cell (for example, the engineered immune cell of the present disclosure); on the other hand, a stimulating signal can be transmitted into the target cell (for example, the engineered immune cell of the present disclosure) through the co-stimulatory domain contained in the NK inhibitory molecule, to stimulate the proliferation and survival thereof, thus better resisting killing of the NK cell. Previous studies have found that using antibodies targeting NK cell inhibitory receptors such as NKG2A, KIR, and ILT2 can compete for binding to binding sites of inhibitory molecules such as HLA-E and HLA-G or neutralizing the inhibitory effect thereof, so as to activate the NK cells. In contrast, the present disclosure has for the first time found that expression of the NK inhibitory molecule targeting the NK inhibitory receptor can inhibit the NK cells. It is also found in the present disclosure that compared with the NK inhibitory molecule containing no co-stimulatory domain, the NK inhibitory molecule containing a co-stimulatory domain has a better inhibitory effect on the killing effect of NK cells.

The co-stimulatory domain may be an intracellular functional signaling domain from a co-stimulatory molecule, and it contains an entire intracellular portion of the co-stimulatory molecule or a functional fragment thereof. "Co-stimulatory molecule" refers to a homologous binding partner that specifically binds to a co-stimulatory ligand on a T cell, thereby mediating a co-stimulatory response (e.g. proliferation) of the T cell. The co-stimulatory molecule includes, but is not limited to, MHC class 1 molecule, BTLA, and Toll ligand receptors. Non-limiting examples of co-stimulatory domains of the present disclosure include but are not limited to a co-stimulatory signaling domain derived form a protein selected from the group consisting of LTB, CD94, TLR1, TLR2, TLR3, TLR4, TLR5, TLR6, TLR7, TLR8, TLR9, TLR10, CARD11, CD2, CD7, CD8, CD18, CD27, CD28, CD30, CD40, CD54, CD83, CD134 (OX40), CD137 (4-1 BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, ZAP70, and a combination thereof. Preferably, the co-stimulatory domain of the present disclosure is from 4-1BB, CD28, CD27, OX40, CD278 or a combination thereof, and more preferably, from 4-1BB, CD28 or a combination thereof. In an embodiment, the co-stimulatory domain of the present disclosure has at least 70%, preferably at least 80%, more preferably at least 90%, 95%, 97% or 99% or 100% sequence identity to an amino acid sequence represented by SEQ ID NO: 13 or 15, or an encoding sequence of the co-stimulatory domain has at least 70%, preferably at least 80%, more preferably at least 90%, 95%, 97% or 99% or 100% sequence identity to a nucleotide sequence represented by SEQ ID NO: 14 or 16.

In an embodiment, the NK inhibitory molecule does not comprise an intracellular signaling domain. In another embodiment, the NK inhibitory molecule further comprises an intracellular signaling domain. That is, the NK inhibitory molecule comprises an NK inhibitory ligand, a transmembrane domain, a co-stimulatory domain, and an intracellular signaling domain. In this embodiment, the binding of the NK inhibitory ligand to the NKIR can transmit an activation signal to the target cell (for example, the engineered immune cell of the present disclosure) through the co-stimulatory domain and the intracellular signaling domain, promote killing of the NK cells by the target cells, and thus further enhance the inhibitory effect on the killing effect of the NK cells.

As used herein, the term "intracellular signaling domain" refers to a protein fraction that transduces an effector function signal and guides a cell to perform a specified function. The intracellular signaling domain is responsible for intracellular primary signaling after the ligand binding domain binds to the antigen, thus causing activation of immune cell and immune reaction. In other words, the intracellular signaling domain is responsible for activating at least one of the normal effector functions of the immune cells in which the NK inhibitory molecule is expressed. For example, the effector functions of T cell can be cytolytic activity or auxiliary activity, including secretion of cytokines.

In an embodiment, the intracellular signaling domain of the present disclosure may be cytoplasmic sequences of a T cell receptor and a co-receptor, which, after antigen receptor binding, act together to initiate primary signaling, as well as any derivative or variant of these sequences and any synthetic sequence having the same or similar function. The intracellular signaling domain may comprise many immunoreceptor tyrosine-based activation motifs (ITAM). Non-limiting examples of intracellular signaling domain of the present disclosure include, but are not limited to, those derived from FcR γ, FcR β, CD3 γ, CD3 δ, CD3 ε, CD3 ζ, CD22, CD79a, CD79b, and CD66d. In a preferred embodiment, the signaling domain of the CAR of the present disclosure may contain a CD3 ζ signaling domain, and the signaling domain has at least 70%, preferably at least 80%, more preferably at least 90%, 95%, 97% or 99% or 100% sequence identity to an amino acid sequence represented by SEQ ID NO: 17 or 19, or an encoding sequence thereof has at least 70%, preferably at least 80%, more preferably at least 90%, 95%, 97% or 99% or 100% sequence identity to a nucleotide sequence represented by SEQ ID NO: 18 or 20.

In an embodiment, the NK inhibitory molecule of the present disclosure further may contain a signal peptide such that when it is expressed in a cell such as a T cell, the nascent protein is directed to the endoplasmic reticulum and subsequently to the cell surface. The core of the signal peptide may comprise a long hydrophobic amino acid segment, which has a tendency to form a single α-helix. At the end of the signal peptide, there is usually an amino acid segment recognized and cleaved by signal peptidase. The signal peptidase can cleave during or after translocation, so as to generate free signal peptide and mature protein. Then, the free signal peptide is digested by a specific protease. Signal peptides that can be used in the present disclosure are well known to those skilled in the art, for example, signal peptides derived from B2M, CD8 α, IgG1, GM-CSFR α, and so on. In an embodiment, the signal peptide that can be used in the present disclosure has at least 70%, preferably at least 80%, more preferably at least 90%, 95%, 97% or 99% or 100% sequence identity to an amino acid sequence represented by SEQ ID NO: 21 or 23, or an encoding sequence of the signal peptide has at least 70%, preferably at least 80%, more preferably at least 90%, 95%, 97% or 99% or 100% sequence identity to a nucleotide sequence represented by SEQ ID NO: 22 or 24.

Suppression or Silencing of at Least One MHC-Related Gene

In an embodiment, the engineered immune cell expressing the NK inhibitory molecule further includes suppression or silencing of expression of at least one MHC-related gene, for example, the expression of at least one MHC gene is suppressed or silenced, or expression of a gene interacting with or modulating the expression of at least one MHC gene is suppressed or silenced.

The major histocompatibility complex (MHC) is originally characterized as a protein that plays a major role in the transplantation reaction, and it is expressed on the surface of all higher vertebrates. It is called H-2 in mice, and HLA in human cells. MHC mainly has two types: class I and class II. MHC class I protein is a heterodimer of two proteins: one is a transmembrane protein α chain encoded by MHCI gene, and the other is a 02 microglobulin chain of an extracellular protein encoded by a gene not located in the MHC gene cluster. The α chain includes three domains, and a foreign peptide binds to two most variable domains α1, α2 at N-terminal. MHC class II protein is also a heterodimer, and comprises two transmembrane proteins encoded by genes within the MHC complex. MHC class I/antigen complex interacts with cytotoxic T cells, whereas MHC class II presents antigen to helper T cells. In addition, MHC class I protein tends to be expressed in almost all nucleated cells and platelets (as well as red blood cells in mice), while MHC class II protein is more selectively expressed. Generally, MHC class II protein is expressed on B cells, some macrophages and monocytes, Langerhans cells, and dendritic cells.

The human HLA class I gene cluster contains three major loci B, C, and A. HLA-A, HLA-B, and HLA-C are HLA class I heavy chain paralogs. The class I molecule is a heterodimer consisting of MHC a heavy chain (encoded by HLA-A, HLA-B or HLA-C) and light chain (0-2 microglobulin, encoded by B2M). The heavy chain is anchored in the membrane. It is about 45 kDa, and contains 8 exons.

Exon 1 encodes a leader peptide, exons 2 and 3 encode α1 and α2 domains, both of which bind to peptides, exon 4 encodes 3 domain, exon 5 encodes a transmembrane region, and exon 6 and 7 encode cytoplasmic tail. Polymorphism within exon 2 and exon 3 results in peptide binding specificity for each class of molecules. Thus, in an embodiment, suppressing or silencing MHC-related gene expression refers to suppressing or silencing the expression of one or more genes selected from the group consisting of HLA-A, HLA-B, HLA-C, and B2M.

Human HLA class II cluster also contains three major loci DP, DQ, and DR, and both class I gene cluster and class II gene cluster are polymorphic. HLA-DPA1, HLA-DQA1, and HLA-DRA belong to HLA class II α chain paralogs. The class II molecule plays a major role in the immune system by presenting an exogenous peptide, and is primarily expressed in antigen presenting cells (e.g., B lymphocyte, dendritic cell, and macrophage). Class II molecule is a heterodimer consisting of α chain and β chain both anchored in the membrane, wherein the α chain is about 33-35 kDa, and contains 5 exons. Exon 1 encodes a leader peptide, exons 2 and 3 encode two extracellular domains, exon 4 encodes a transmembrane domain, and exon 5 encodes a cytoplasmic tail. Thus, in an embodiment, suppressing or silencing MHC-related gene expression refers to suppressing or silencing the expression of one or more genes selected from the group consisting of HLA-DPA, HLA-DQ, and HLA-DRA.

Expression of MHC class I and class II also depends on a variety of accessory proteins. For example, Tap1 and Tap2 subunits are part of TAP transporter complex necessary for loading peptide antigens on the HLA class I complex. LMP2 and LMP7 proteosome subunits function in proteolytic degradation of antigens to peptides so as to be displayed on HLA. Reducing LMP7 has been shown to reduce the expression amount of MHC class I at the cell surface. MHC class II expression is induced and expressed by some positive regulators, for example, RFX complex and CIITA. The RFX complex consists of three subunits: RFXANK (also known as RFXB), RFX5, and RFX accessory protein (also known as RFXAP). The RFX complex promotes the expression of MHC class II molecules by promoting the binding of other transcription factors to the promoter of MHC class II molecules and enhancing the specificity of binding of the promoter. CIITA is a major control factor for MHC class II expression. CIITA comprises an N-terminal rich in acidic amino acids, a PST region rich in Pro, Ser, and Thr, an intermediate GTP binding region, and a C terminal rich in Leu repeat sequence (LRR), wherein the N-terminal acidic region and the PST region are transcriptional activation regions. Thus, in an embodiment, suppressing or silencing MHC-related gene expression refers to suppressing or silencing the expression of one or more genes selected from the group consisting of TAP1, TAP2, LMP2, LMP7, RFX5, RFXAP, RFXANK, and CIITA.

Thus, in an embodiment, suppressing or silencing MHC-related gene expression refers to suppressing or silencing the expression of one or more genes selected from the group consisting of HLA-A, HLA-B, HLA-C, B2M, HLA-DPA, HLA-DQ, HLA-DRA, TAP1, TAP2, LMP2, LMP7, RFX5, RFXAP, RFXANK, CIITA, and a combination thereof, preferably selected from HLA-A, HLA-B, HLA-C, B2M, RFX5, RFXAP, RFXANK, CIITA, and a combination thereof.

In an embodiment, the expression of at least one TCR/CD3 gene of the engineered immune cell expressing the NK inhibitory molecule is further suppressed or silenced.

T cell receptor (TCR) is a characteristic marker of the surface of all T cells. It forms a TCR/CD3 complex by binding to CD3 through a non-covalent bond, and generates a specific antigen stimulation signal by binding to a specific MHC-antigen peptide complex on the surface of the antigen presenting cell, to activate T cell and exert the killing effect. TCR is a heterodimer composed of two different peptide chains, and is generally divided into two types: α/β type and γ/δ type, in which 95% or more of peripheral T lymphocytes express TCR α/β. The TCR α chain is encoded by the TRAC gene, and the β chain is encoded by the TRBC gene. Each peptide chain of the TCR includes a variable region (V region), a constant region (C region), a transmembrane region, and a cytoplasmic region, wherein the cytoplasmic region is too short to transmit an antigen stimulation signal. TCR molecule belongs to the immunoglobulin superfamily, and the antigen specificity thereof exists in V region; the V region has three hypervariable regions, i.e. CDR1, CDR2, and CDR3, wherein the CDR3 has the maximum variation, and directly determines the antigen binding specificity of the TCR. When TCR recognizes MHC-antigen peptide complexes, CDR1 and CDR2 recognize and bind to the MHC molecule, and CDR3 directly binds to the antigen peptide. CD3 includes four subunits: γ, δ, ε, ζ, usually existing in the form of dimers εγ, εδ, ζζ. All of the four subunits comprise a conserved immunoreceptor tyrosine-based activation motif (ITAM), in which two tyrosine residues, after being phosphorylated by tyrosine protein kinases, transmit an activation signal to T cells. Thus, in an embodiment, suppressing or silencing at least one TCR/CD3 gene expression refers to suppressing or silencing the expression of one or more genes selected from the group consisting of TRAC, TRBC, CD3 γ, CD3 δ, CD3 ε, CD3 ζ.

In a preferred embodiment, the expression of at least one TCR/CD3 gene and at least one MHC-related gene in the engineered immune cell expressing the NK inhibitory molecule is suppressed or silenced, wherein the at least one TCR/CD3 gene is selected from the group consisting of TRAC, TRBC, CD3 γ, CD3 δ, CD3 ε, CD3 ζ, and a combination thereof; and the at least one MHC-related gene is selected from the group consisting of HLA-A, HLA-B, HLA-C, B2M, HLA-DPA, HLA-DQ, HLA-DRA, TAP1, TAP2, LMP2, LMP7, RFX5, RFXAP, RFXANK, CIITA, and a combination thereof, preferably selected from HLA-A, HLA-B, HLA-C, B2M, RFX5, RFXAP, RFXANK, CIITA, and a combination thereof.

In a preferred embodiment, the at least one TCR/CD3 gene is selected from the group consisting of TRAC, TRBC, and a combination thereof, and the at least one MHC-related gene is selected from the group consisting of B2M, RFX5, RFXAP, RFXANK, CIITA, and a combination thereof. In an embodiment, the expression of TRAC or TRBC and the expression of B2M of the engineered immune cell are suppressed or silenced. In an embodiment, the expression of TRAC or TRBC and the expression of CIITA of the engineered immune cell are suppressed or silenced. In a preferred embodiment, the expression of TRAC or TRBC, and the expression of B2M and CIITA of the engineered immune cell are suppressed or silenced. In a preferred embodiment, the expression of TRAC or TRBC, and the expression of B2M and RFX5 of the engineered immune cell are suppressed or silenced.

In an embodiment, in addition to the MHC-related gene and the optional TCR/CD3 gene, the expression of at least one gene selected from the following in the engineered immune cell of the present disclosure can be further suppressed or silenced: CD52, GR, dCK and immune checkpoint gene, such as PD1, LAG3, TIM3, CTLA4, PPP2CA, PPP2CB, PTPN6, PTPN22, PDCD1, HAVCR2, BTLA, CD160, TIGIT, CD96, CRTAM, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAGI, SIT, FOXP3, PRDM1, BATF, GUCY1A2, GUCY1A3, GUCY1B2, and GUCY1B3.

Methods for inhibiting gene expression or silencing a gene are well known to those skilled in the art, including but not limited to, for example, DNA breakage mediated by a meganuclease, a zincfinger nuclease, a TALE nuclease or a Cas enzyme in a CRISPR system, or inactivating a gene by antisense oligonucleotides, RNAi, shRNA, and other technologies.

Chimeric Antigen Receptor

In another aspect, the engineered immune cell expressing an NK inhibitory molecule of the present disclosure further may express a chimeric antigen receptor. That is, in this embodiment, the engineered immune cell expresses an NK inhibitory molecule and a chimeric antigen receptor, and preferably, expression of at least one MHC-related gene of the engineered immune cell is suppressed or silenced. In a preferred embodiment, expression of at least one TCR/CD3 gene further included in the engineered immune cell is suppressed or silenced.

As used herein, the term "chimeric antigen receptor" or "CAR" refers to an artificially constructed hybrid polypeptide, where the hybrid polypeptide generally comprises one or more ligand binding domains (e.g., an antigen binding moiety of an antibody), a transmembrane domain, a co-stimulatory domain, and an intracellular signaling domain, and various domains are linked via a linker. CAR can redirect the specificity and reactivity of T cells and other immune cells to selected targets in a non-MHC-restricted manner by utilizing the antigen binding properties of monoclonal antibodies. Non-MHC-restricted antigen recognition gives CAR cells the ability to recognize antigen independent of antigen processing, thus bypassing the major mechanism of tumor escape. Furthermore, when expressed within T cells, CAR advantageously does not dimerize with α chain and β chain of the endogenous T cell receptor (TCR).

As used herein, "ligand binding domain" refers to any structure that can bind to a ligand (e.g. antigen) or a functional variant thereof. The ligand binding domain may be an antibody structure, including, but not limited to, monoclonal antibody, polyclonal antibody, recombinant antibody, human antibody, humanized antibody, murine antibody, chimeric antibody, and a functional fragments thereof. For example, the ligand binding domain includes, but is not limited to, intact antibody, Fab, Fab', F(ab')2, Fv fragment, scFv antibody fragment, linear antibody, sdAb (VH or VL), nanobody (Nb), recombinant fibronectin domain, anticalin, DARPIN, and so on, preferably selected from Fab, scFv, sdAb, and nanobody. In the present disclosure, the ligand binding domain may be univalent or bivalent, and may be a monospecific, bispecific or multispecific antibody.

"Fab" refers to any one of two identical fragments produced by digestion of an immunoglobulin molecule using papain, and consists of an intact light chain and a heavy chain N-terminal part linked by a disulfide bond, wherein the heavy chain N-terminal part includes a heavy chain variable region and CH1. Compared with the intact IgG, Fab has no Fc fragment, has relatively high fluidity and tissue penetration ability, and can univalently bind to an antigen without mediating antibody effects.

"Single chain antibody" or "scFv" is an antibody composed of an antibody heavy chain variable region (VH) and a light chain variable region (VL) linked by a linker. The optimal length and/or amino acid composition of the linker can be selected. The length of the linker will significantly affect the variable region folding and interaction of the scFv. In fact, intrachain folding can be prevented if a shorter linker (e.g. 5-10 amino acids) is used. Regarding the selection of size and composition of the linker, see, e.g., Hollinger et al., 1993 Proc Natl Acad. Sci. U.S.A. 90:6444-6448; US patent applications with publication Nos. 2005/0100543, 2005/0175606, 2007/0014794; and PCT applications with publication Nos. WO2006/020258 and WO2007/024715, which are incorporated herein by reference in their entirety. The scFv may contain a VH and a VL linked in any order, e.g., VH-linker-VL or VL-linker-VH.

"Single domain antibody" or "sdAb" refers to an antibody that naturally lacks a light chain, and the antibody contains only one heavy chain variable region (VHH) and two conventional CH2 and CH3 regions, also known as "heavy chain antibody".

"Nanobody" or "Nb" refers to a VHH structure that is individually cloned and expressed, which has structural stability and binding activity to an antigen comparable to those of the original heavy chain antibody, and it is the smallest unit currently known to be capable of binding to a target antigen.

The term "functional variant" or "functional fragment" refers to a variant that substantially contains the amino acid sequence of a parent, but, compared with the parent amino acid sequence, contains at least one amino acid modification (i.e., substitution, deletion or insertion), provided that the variant retains the biological activity of the parent amino acid sequence. For example, for an antibody, a functional fragment thereof is an antigen binding moiety thereof. In an embodiment, the amino acid modification is preferably a conservative modification.

As used herein, the term "conservative modification" refers to an amino acid modification that does not significantly affect or alter the binding characteristics of the antibody or antibody fragment containing the amino acid sequence. These conservative modifications include amino acid substitution, addition, and deletion. The modifications can be introduced into the chimeric antigen receptor of the present disclosure by standard techniques known in the art, such as site-directed mutagenesis and PCR-mediated mutagenesis. The conservative amino acid substitution is the substitution in which the amino acid residue is replaced with an amino acid residue having a similar side chain. Amino acid residue families having a similar side chain have been defined in the art, including basic side chain (e.g., lysine, arginine, histidine), acidic side chain (e.g., aspartic acid, glutamic acid), uncharged polar side chain (e.g., glycine, asparagine, glutamine, serine, threonine, tyrosine, cysteine), nonpolar side chain (e.g., alanine, valine, leucine, isoleucine, proline, phenylalanine, methionine, tryptophan), β-branched side chain (e.g., threonine, valine, isoleucine), and aromatic side chain (e.g., tyrosine, phenylalanine, tryptophan, histidine). The conservative modifications may be selected, for example, based on polarity, charge, solubility, hydrophobicity, hydrophilicity, and/or similarity in amphiphilic properties of residues involved.

Thus, the "functional variant" or "functional fragment" has at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the parent amino acid sequence, and retains the biological activity, e.g., binding activity, of the parent amino acid.

As used herein, the term "sequence identity" indicates the degree to which two (nucleotide or amino acid) sequences have the same residue at the same position in an alignment, and is generally expressed by percentage. Preferably, the identity is determined over the entire length of the sequences being compared. Thus, two copies with identical sequences have 100% identity. Those skilled in the art will recognize that some algorithms can be used to determine sequence identity using standard parameters, for example, Blast (Altschul et al. (1997) Nucleic Acids Res. 25:3389-3402), Blast2 (Altschul et al. (1990) J. Mol. Biol. 215:403-410), Smith-Waterman (Smith et al. (1981) J. Mol. Biol. 147:195-197), and ClustalW.

The selection of ligand binding domain depends on the cell surface marker on a target cell to be recognized and associated with a specific disease state, for example, a tumor specific antigen or a tumor associated antigen. Thus, in an embodiment, the ligand binding domain of the present disclosure binds to one or more targets selected from the group consisting of TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, mesothelin, IL-11Ra, PSCA, PRSS21, VEGFR2, LewisY, CD24, PDGFR-β, SSEA-4, CD20, Folate receptor α, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor R, TEM1/CD248, TEM7R, CLDN6, GPRC5D, CXORF61, CD97, CD 179a, ALK, polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGF β, APRIL, Claudin18.2, NKG2D, and any combination thereof. Preferably, the target is selected from the group consisting of: CD19, CD20, CD22, BAFF-R, CD33, EGFRvIII, BCMA, GPRC5D, PSMA, ROR1, FAP, ERBB2 (Her2/neu), MUC1, EGFR, CAIX, WT1, NY-ESO-1, CD79a, CD79b, GPC3, Claudin18.2, NKG2D, and any combination thereof. Depending on the antigen to be targeted, the CAR of the present disclosure may be designed to include a ligand binding domain specific for the antigen. For example, if CD19 is the antigen to be targeted, a CD19 antibody can be used as the ligand binding domain of the present disclosure.

Structures such as transmembrane domain, co-stimulatory domain, intracellular signaling domain, and optional hinge region, signal peptide contained in the CAR that can be used in the present disclosure are defined above.

In an embodiment, the CAR of the present disclosure further may contain a switch structure, so as to regulate the expression time of the CAR. For example, the switch structure may be in the form of a dimerization domain, which causes a conformational change by binding to a corresponding ligand thereof, and exposes the extracellular binding domain to bind to a targeted antigen, thereby activating the signaling pathway. Alternatively, a switch domain also may be used to link a binding domain and a signaling domain, respectively, and only when the switch domains are bound to each other (for example, in the presence of an inducing compound), the binding domain and the signaling domain can be linked together through a dimer, thereby activating the signal pathway. The switch structure also can be in a form of a masking peptide. The masking peptide can shield the extracellular binding domain, and prevent it from binding to the targeted antigen, and after the masking peptide is cleaved by, for example, a protease, the extracellular binding domain is exposed, making it become a "normal" CAR structure. A variety of switch structures known to those skilled in the art can be used in the present disclosure.

In an embodiment, the CAR of the present disclosure further may comprise a suicide gene, i.e. making it express a cell death signal that can be induced by an exogenous substance, so as to eliminate the CAR cell when needed (e.g., when serious toxic side effects occur). For example, the suicide gene may be in the form of an inserted epitope, e.g., a CD20 epitope, an RQR8, etc., and when needed, the CAR cell can be eliminated by adding an antibody or reagent that targets these epitopes. The suicide gene also may be herpes simplex virus thymidine kinase (HSV-TK), which gene can induce cell apoptosis when receiving ganciclovir treatment. The suicide gene further may be iCaspase-9, and dimerization of iCaspase-9 can be induced by a chemical induction drug such as AP1903 and AP20187, so as to activate the downstream Caspase3 molecule, and cause apoptosis. A variety of suicide genes known to those of skill in the art can be used in the present disclosure.

When the NK inhibitory molecule contains an intracellular signaling domain and the cell expresses a CAR, the NK inhibitory molecule and CAR of the present disclosure may share structures other than the binding region, such as a co-stimulatory domain and an intracellular signaling domain, as desired. Therefore, in this embodiment, the engineered immune cell of the present disclosure: (1) expresses a fusion protein of the NK inhibitory molecule of the present disclosure and a chimeric antigen receptor, the fusion protein comprises an NK inhibitory ligand, a ligand binding domain, a transmembrane domain, a co-stimulatory domain, and an intracellular signaling domain, and (2) expression of at least one MHC-related gene is suppressed or silenced.

Nucleic Acid and Vector

The present disclosure further provides a nucleic acid molecule, which contains a nucleic acid sequence encoding the NK inhibitory molecule of the present disclosure. Optionally, the nucleic acid molecule further may comprise a nucleic acid sequence encoding the chimeric antigen receptor.

As used herein, the term "nucleic acid molecule" includes a sequence of ribonucleotide and deoxyribonucleotide, such as modified or unmodified RNA or DNA, each in single-stranded and/or double-stranded form, in linear or circular or their mixtures (including hybrid molecules). Thus, the nucleic acid according to the present disclosure includes DNA (e.g. dsDNA, ssDNA, cDNA), RNA (e.g. dsRNA, ssRNA, mRNA, ivtRNA), their combinations or derivatives (e.g. PNA). Preferably, the nucleic acid is DNA or RNA, more preferably mRNA.

The nucleic acid may contain a conventional phosphodiester bond or an unconventional bond (e.g., amide bond, such as found in peptide nucleic acid (PNA)). The nucleic acid of the present disclosure further may comprise one or more modified bases, such as, for example, trityl base and uncommon base (such as inosine). Other modifications also can be contemplated, including chemical, enzymatic or metabolic modifications, so long as the multi-chain CAR of the present disclosure can be expressed from polynucleotides. The nucleic acid can be provided in isolated form. In an embodiment, the nucleic acid also may include a regulatory sequence, such as a transcriptional control element (including a promoter, an enhancer, an operon, a repressor, and a transcription termination signal), ribosome binding sites, and intron.

The nucleic acid sequences of the present disclosure can be codon-optimized for optimal expression in a desired host cell (e.g., immune cell); or for expression in a bacterial, yeast or insect cell. Codon optimization refers to substitution of a codon in the target sequence that is generally rare in highly expressed genes of a given species with a codon that is generally common in highly expressed genes of such species, and the codons before and after the substitution encode the same amino acid. Therefore, the selection of an optimal codon depends on the codon usage preference of the host genome.

The present disclosure further provides a vector, containing the nucleic acid molecule of the present disclosure. Optionally, the nucleic acid sequence encoding the NK inhibitory molecule and the nucleic acid sequence encoding the chimeric antigen receptor can be located in the same vector or different vectors.

As used herein, the term "vector" is an intermediary nucleic acid molecule used to transfer (exogenous) genetic material into a host cell, and in the host cell the nucleic acid molecule can be, for example, replicated and/or expressed.

The vector generally includes targeting vectors and expression vectors. The "targeting vector" is a medium that delivers an isolated nucleic acid to the interior of a cell by, for example, homologous recombination or by using a hybrid recombinase of a sequence at specific target site. The "expression vector" is a vector used for transcription of heterologous nucleic acid sequences (for example, those sequences encoding the chimeric antigen receptor polypeptides of the present disclosure) in suitable host cells and the translation of their mRNAs. Suitable vectors that can be used in the present disclosure are known in the art, and many are commercially available. In an embodiment, the vector of the present disclosure includes, but is not limited to, plasmid, virus (e.g., retrovirus, lentivirus, adenovirus, vaccinia virus, Rous sarcoma virus (RSV), polyoma virus, and adeno-associated virus (AAV), etc.), bacteriophage, phagemid, cosmid, and artificial chromosome (including BAC and YAC). The vector itself is usually a nucleotide sequence, and usually is a DNA sequence containing an insert (transgene) and a larger sequence as "backbone" of the vector. Engineered vector typically also contains a start site autonomously replicating in the host cell (if stable expression of polynucleotide is desired), a selectable marker, and a restriction enzyme cleavage site (e.g., a multiple cloning site, MCS). The vectors may additionally contain elements such as a promoter, a poly-A tail (polyA), 3' UTR, an enhancer, a terminator, an insulator, an operon, a selectable marker, a reporter gene, a targeting sequence, and/or a protein purification tag. In a specific embodiment, the vector is an in vitro transcription vector.

Engineered Immune Cell

The present disclosure further provides an engineered immune cell, which expresses the NK inhibitory molecule of the present disclosure, and wherein expression of at least one MHC-related gene is suppressed or silenced. In an embodiment, the engineered immune cell of the present disclosure further expresses a chimeric antigen receptor, wherein the chimeric antigen receptor comprises one or more ligand binding domains, a transmembrane domains, a co-stimulatory domains, and an intracellular signaling domains. In a preferred embodiment, the engineered immune cell of the present disclosure further comprises suppressed or silenced expression of at least one TCR/CD3 gene.

In an embodiment, in addition to the MHC-related gene and the optional TCR/CD3 gene, the expression of at least one gene selected from the following in the engineered immune cell of the present disclosure can be further suppressed or silenced: CD52, GR, dCK and immune checkpoint gene, such as PD1, LAG3, TIM3, CTLA4, PPP2CA, PPP2CB, PTPN6, PTPN22, PDCD1, HAVCR2, BTLA, CD160, TIGIT, CD96, CRTAM, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAGI, SIT, FOXP3, PRDM1, BATF, GUCY1A2, GUCY1A3, GUCY1B2, and GUCY1B3.

When the NK inhibitory molecule contains an intracellular signaling domain and the cell expresses a CAR, the NK inhibitory molecule and CAR of the present disclosure may share structures other than the binding region, such as the co-stimulatory domain and an intracellular signaling domain, as desired. Therefore, in this embodiment, the engineered immune cell of the present disclosure: (1) expresses a fusion protein of the NK inhibitory molecule of the present disclosure and a chimeric antigen receptor, the fusion protein comprises an NK inhibitory ligand, a ligand binding domain, a transmembrane domain, a co-stimulatory domain, and an intracellular signaling domain, and (2) expression of at least one MHC-related gene is suppressed or silenced. In a preferred embodiment, the engineered immune cell of the present disclosure further comprises suppressed or silenced expression of at least one TCR/CD3 gene.

As used herein, the term "immune cell" refers to any cell of the immune system that has one or more effector functions (e.g., cytotoxic cell killing activity, secretion of cytokines, induction of ADCC and/or CDC). For example, the immune cell may be a B cell, a T cell, a macrophage, a dendritic cell, a monocyte, an NK cell or an NKT cell, or an immune cell obtained from a stem cell source such as cell umbilical cord blood. Preferably, the immune cell is a T cell. The T cell may be any T cell, such as in vitro cultured T cell, for example, primary T cell or T cell from in vitro cultured T cell line, e.g., Jurkat, SupT1, etc. or T cell obtained from a subject. Examples of subject include humans, dogs, cats, mice, rats, and transgenic species thereof. The T cell can be obtained from a variety of sources, including peripheral blood monocytes, bone marrow, lymph node tissue, umbilical blood, thymus tissue, tissue from infection sites, ascites, pleural effusion, spleen tissue, and tumors. The T cell also may be concentrated or purified. The T cell may be at any stage of development including, but not limited to, a CD4+/CD8+ T cell, a CD4+ helper T cell (e.g., Th1 and Th2 cells), CD8+ T cell (e.g., cytotoxic T cell), tumor infiltrating cell, memory T cell, naive T cell, γδ-T cell, αβ-T cell, etc. In a preferred embodiment, the immune cell is a human T cell. The T cell can be isolated from the blood of a subject using a variety of techniques known to those of skill in the art, such as Ficoll.

The NK inhibitory molecule and optional chimeric antigen receptor can be introduced into the immune cell using conventional methods known in the art (e.g., by transduction, transfection, transformation). "Transfection" is a process of introducing a nucleic acid molecule or polynucleotide (including a vector) into a target cell. An example is RNA transfection, i.e., the process of introducing RNA (such as in vitro transcribed RNA, ivtRNA) into a host cell. This term is mainly used for a non-viral method in eukaryotic cells. The term "transduction" is generally used to describe virus-mediated transfer of nucleic acid molecules or polynucleotides. Transfection of animal cells typically involves opening transient pores or "holes" in the cell membrane, so as to allow uptake of material. Transfection may be carried out using calcium phosphate, by electroporation, by extrusion of cells or by mixing cationic lipids with the material so as to produce liposomes which fuse with the cell membrane and deposit their cargo into the interior. Exemplary techniques for transfecting eukaryotic host cells include lipid vesicle-mediated uptake, heat shock-mediated uptake, calcium phosphate-mediated transfection (calcium phosphate/DNA co-precipitation), microinjection, and electroporation. The term "transformation" is used to describe the non-virus transfer of a nucleic acid molecule or polynucleotide (including a vector) to bacteria, and also to non-animal eukaryotic cells (including plant cells). Thus, the transformation is a genetic alteration of bacterial or non-animal eukaryotic cells, which is produced by direct uptake of a cell membrane from its surroundings and subsequent incorporation of exogenous genetic material (nucleic acid molecule). The transformation can be achieved by artificial means. In order for transformation to occur, the cell or bacterium must be in a competent state. For prokaryotic transformation, the techniques may include heat shock-mediated uptake, fusion to bacterial protoplasts of intact cells, microinjection, and electroporation.

Kit and Pharmaceutical Composition

The present disclosure provides a kit, which contains the NK inhibitory molecule, the nucleic acid molecule, the vector or the engineered immune cell of the present disclosure.

In a preferred embodiment, the kit of the present disclosure further contains instructions.

The present disclosure further provides a pharmaceutical composition, which contains the NK inhibitory molecule, the engineered immune cell, the nucleic acid molecule or the vector of the present disclosure as an active agent, and one or more pharmaceutically acceptable excipients. Therefore, the present disclosure further encompasses use of the NK inhibitory molecule, the nucleic acid molecule, the vector or the engineered immune cell in the preparation of a pharmaceutical composition or medicine.

As used herein, the term "pharmaceutically acceptable excipient" refers to a vector and/or excipient that is pharmacologically and/or physiologically compatible (i.e., capable of triggering a desired therapeutic effect without causing any undesired local or systemic effects) with the subject and active ingredient, and it is well known in the art (see, e.g., Remington's Pharmaceutical Sciences. Edited by Gennaro A R, 19th ed. Pennsylvania: Mack Publishing Company, 1995). Examples of pharmaceutically acceptable excipient include, but are not limited to, filler, binder, disintegrant, coating agent, adsorbent, anti-adherent, glidant, antioxidant, flavoring agent, colorant, sweetener, solvent, co-solvent, buffer agent, chelating agent, surfactant, diluent, wetting agent, preservative, emulsifier, cladding agent, isotonic agent, absorption delaying agent, stabilizer, and tension regulator. It is known to those skilled in the art to select a suitable excipient to prepare the desired pharmaceutical composition of the present disclosure. Exemplary excipients for use in the pharmaceutical composition of the present disclosure include saline, buffered saline, dextrose, and water. Generally, the selection of a suitable excipient depends, in particular, on the active agent used, the disease to be treated, and the desired dosage form of the pharmaceutical composition.

The pharmaceutical composition according to the present disclosure is suitable for multiple routes of administration. Generally, the administration is parenterally accomplished. Parenteral delivery methods include topical, intraarterial, intramuscular, subcutaneous, intramedullary, intrathecal, intraventricular, intravenous, intraperitoneal, intrauterine, intravaginal, sublingual, or intranasal administration.

The pharmaceutical composition according to the present disclosure also can be prepared in various forms, such as solid, liquid, gaseous or lyophilized forms, particularly the pharmaceutical composition can be prepared in the form of ointment, cream, transdermal patch, gel, powder, tablet, solution, aerosol, granule, pill, suspension, emulsion, capsule, syrup, elixir, extract, tincture or liquid extract, or in a form particularly suitable for the desired method of administration. Processes known in the present disclosure for producing a medicine may include, for example, conventional mixing, dissolving, granulating, dragee-making, grinding, emulsifying, encapsulating, embedding or lyophilizing process. The pharmaceutical composition containing, for example, the immune cell as described herein is generally provided in a form of solution, and preferably contains a pharmaceutically acceptable buffer.

The pharmaceutical composition according to the present disclosure further may be administered in combination with one or more other agents suitable for the treatment and/or prophylaxis of diseases to be treated. Preferred examples of agent suitable for the combination include known anti-cancer medicines such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E, vincristine and doxorubicin; peptide cytotoxins, such as ricin, diphtheria toxin, *Pseudomonas* exotoxin A, DNase and RNase; radionuclides such as iodine 131, rhenium 186, indium 111, iridium 90, bismuth 210 and 213, actinides 225 and astatine 213; prodrugs such as antibody-directed enzyme prodrugs; immunostimulatory agents such as platelet factor 4, and melanoma growth stimulating protein; antibodies or fragments thereof, such as anti-CD3 antibodies or fragments thereof, complement activators, heterologous protein domains, homologous protein domains, viral/bacterial protein domains and viral/bacterial peptides. In addition, the pharmaceutical composition of the present disclosure also can be used in combination with one or more other treatment methods, such as chemotherapy and radiotherapy.

Therapeutic Application

The present disclosure further provides a method of treating a subject with cancer, infection or autoimmune disease, including administering to the subject an effective amount of the NK inhibitory molecule, the nucleic acid molecule, the vector, the engineered immune cell or the pharmaceutical composition according to the present disclosure. Therefore, the present disclosure also encompasses use of the NK inhibitory molecule, the nucleic acid molecule, the vector, or the engineered immune cell in the preparation of a medicine for treating cancer, infection or autoimmune diseases.

In an embodiment, an effective amount of the immune cell and/or the pharmaceutical composition of the present disclosure is directly administered to the subject.

In another embodiment, the treatment method of the present disclosure is ex vivo treatment. Specifically, the method includes the steps of: (a) providing a sample, the sample containing an immune cell; (b) suppressing or silencing expression of at least one TCR/CD3 gene and at least one MHC-related gene of the immune cell in vitro, and introducing the NK inhibitory molecule of the present disclosure and an optional chimeric antigen receptor into the immune cell to obtain a modified immune cell, and (c) administering the modified immune cell to the subject in need thereof. Preferably, the immune cell provided in step (a) is selected from a B cell, a macrophage, a dendritic cell, a monocyte, a T cell, an NK cell or an NKT cell; and the immune cell can be obtained from the sample (particularly a blood sample) of the subject by conventional methods known in the art. However, other immune cells capable of expressing the chimeric antigen receptor and NK inhibitory molecule of the present disclosure and exerting the desired biological effect function as described herein also can be used. Besides, the immune cells generally selected are compatible with the subject's immune system, i.e., it is preferred that the immune cells do not trigger an immunogenic response. For example, a "general recipient cell", i.e., a universally compatible lymphocyte exerting a desired biological effect function and being capable of growing and amplifying in vitro, can be used. The use of such cells will not require obtaining and/or providing the subject's own lymphocyte. The ex vivo introduction of step (c) may be carried out by introducing the nucleic acid or vector described herein into the immune cell via electroporation or by infecting the immune cell with a viral vector, wherein the viral vector is a lentiviral vector, adenoviral vector, adeno-associated viral vector or retroviral vector as previously described. Other conceivable methods include using a transfection reagent (such as a liposome) or transient RNA transfection.

In an embodiment, the immune cell is an autologous or allogeneic cell, preferably B cell, T cell, macrophage, dendritic cell, monocyte or NK cell, NKT cell, more preferably T cell, NK cell or NKT cell.

As used herein, the term "autologous" means that any material derived from an individual will be later re-introduced into the same individual.

As used herein, the term "allogeneic" means that the material is derived from a different animal or different patient of the same species as the individual into which the material is introduced. When the genes at one or more loci are different, two or more individuals are considered allogeneic to each other. In some cases, genetic differences in allogeneic materials from various individuals of the same species may be sufficient for antigen interactions to occur.

As used herein, the term "subject" refers to a mammal. The mammal may be, but is not limited to, a human, a non-human primate, a mouse, a rat, a dog, a cat, a horse or a cow. Mammals other than human can be advantageously used as subjects representing cancer animal models. Preferably, the subject is a human.

In an embodiment, the cancer is a cancer associated with expression of the target to which the ligand binding domain binds. For example, the cancer includes, but is not limited to, brain glioma, blastoma, sarcoma, leukemia, basal cell carcinoma, biliary tract cancer, bladder cancer, bone cancer, brain and CNS cancer, breast cancer, peritoneal cancer, cervical cancer, choriocarcinoma, colon and rectal cancer, connective tissue cancer, cancer of digestive system, endometrial cancer, esophageal cancer, eye cancer, head and neck cancer, stomach cancer (including gastrointestinal cancer), glioblastoma (GBM), liver cancer, hepatoma, intraepithelial tumor, kidney cancer, larynx cancer, liver tumor, lung cancer (such as small cell lung cancer, non-small cell lung cancer, lung adenocarcinoma and squamous lung cancer), lymphoma (including Hodgkin's lymphoma and non-Hodgkin's lymphoma), melanoma, myeloma, neuroblastoma, oral cancer (e.g., lips, tongue, mouth, and pharynx), ovarian cancer, pancreatic cancer, prostate cancer, retinoblastoma, rhabdomyosarcoma, rectal cancer, cancer of respiratory system, salivary gland cancer, skin cancer, squamous cell carcinoma, stomach cancer, testicular cancer, thyroid cancer, uterine or endometrial cancer, malignant tumor of urinary system, vulval cancer and other cancers and sarcomas, and B cell lymphoma (including low-grade/follicular non-Hodgkin's lymphoma (NHL), small lymphocytic (SL) NHL, intermediate-grade/follicular NHL, intermediate-grade diffuse NHL, high-grade immunoblastic NHL, high-grade lymphoblastic NHL, high-grade small non-cracked cell NHL, bulky disease NHL), mantle cell lymphoma, AIDS-related lymphoma, and Waldenstrom macroglobulinemia, chronic lymphocytic leukemia (CLL), acute lymphocytic leukemia (ALL), B cell acute lymphocytic leukemia (B-ALL), T cell acute lymphocytic leukemia (T-ALL), B cell prolymphocytic leukemia, blast cell plasmacytoid dendritic cell tumor, Burkitt lymphoma, diffuse large B cell lymphoma, follicular lymphoma, chronic myelogenous leukemia (CML), malignant lymphoproliferative disorder, MALT lymphoma, hairy cell leukemia, marginal zone lymphoma, multiple myeloma, myelodysplasia, plasmablastic lymphoma, preleukemia, plasmacytoid dendritic cell tumor, post-transplant lymphoproliferative disorder (PTLD), and other diseases associated with target expression. Preferably, the disease which can be treated with the engineered immune cell or the pharmaceutical composition of the present disclosure is selected from the group consisting of: leukemia, lymphoma, multiple myeloma, brain glioma, pancreatic cancer, stomach cancer, and so on.

In an embodiment, the infection includes, but is not limited to, infections caused by viruses, bacteria, fungi, and parasites.

In an embodiment, the autoimmune disease includes, but is not limited to, type I diabetes, celiac disease, Graves disease, inflammatory bowel disease, multiple sclerosis, psoriasis, rheumatoid arthritis, Addison disease, sicca syndrome, Hashimoto thyroiditis, myasthenia gravis, vasculitis, pernicious anemia, and systemic lupus erythematosus, etc.

In an embodiment, the method further includes administering to the subject one or more additional chemotherapeutic agents, biological agents, medicines or treatments. In this embodiment, the chemotherapeutic agents, biological agents, medicines or treatments are selected from the group consisting of radiotherapy, surgery, antibody reagent and/or small molecule and any combination thereof.

The present disclosure will be described in detail below with reference to the accompanying drawings and examples. It should be noted that those skilled in the art should understand that the accompanying drawings of the present disclosure and examples thereof are only for illustrative purpose, and cannot constitute any limitation to the present disclosure. The examples of the present disclosure and the features in the examples may be combined with each other without contradiction.

DETAILED DESCRIPTION OF EMBODIMENTS

Figure 1:
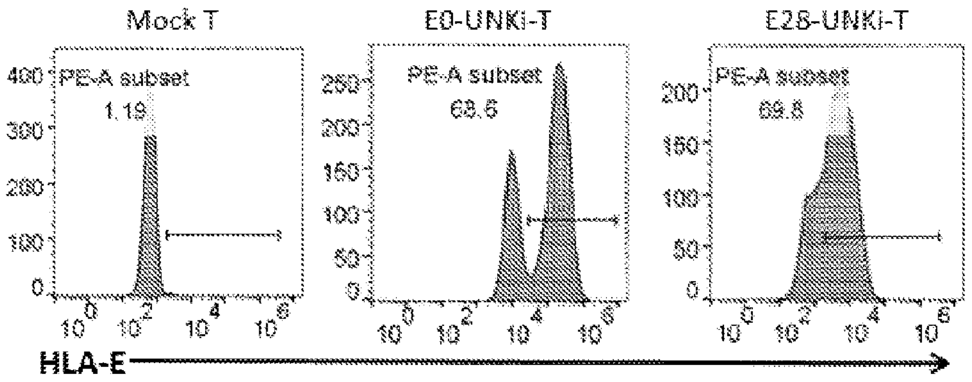
FIG. 1: Expression levels of HLA-E in E0-UNKi-T and E28-UNKi-T cells are shown.

The T cells used in all the examples of the present disclosure are primary human CD4+CD8+ T cells isolated from healthy donors by Ficoll-Paque™ PREMIUM (GE Healthcare, Lot No. 17-5442-02) using leukapheresis.

Example 1: Construction of UNKi-T Immune Cells Expressing NK Inhibitory Molecules and with TCR/HLA-I/HLA-H being Knocked Out The following encoding sequences were synthesized, and sequentially cloned into a pGEM-T Easy vector (Promega, Lot No. A1360): B2m signal peptide (SEQ ID NO: 21), NK inhibitory ligand, CD28 hinge region (SEQ ID NO: 27), CD28 transmembrane region (SEQ ID NO: 11), wherein the NK inhibitory ligand was an extracellular region of E-cadherin (SEQ ID NO: 41, corresponding to ECad0 plasmid), a fusion molecule of B2M and HLA-E extracellular region (containing presenting peptide of SEQ ID NO: 46, B2M of SEQ ID NO: 37, and HLA-E extracellular region mutant of SEQ ID NO: 33, wherein a nucleic acid sequence of B2M was synonymously mutated SEQ ID NO: 38, corresponding to E0 plasmid), or a fusion molecule of B2M and HLA-G extracellular region (containing B2M of SEQ ID NO: 37 and HLA-G extracellular region of SEQ ID NO: 35, wherein the nucleic acid sequence of B2M was the synonymously mutated SEQ ID NO: 38, corresponding to G0 plasmid). A CD28 co-stimulatory domain (SEQ ID NO: 13) was further included in the ECad0, E0, and G0 plasmids to obtain ECad28, E28, and G28 plasmids, respectively. Correct insertion of the target sequences into the plasmids was confirmed by sequencing.

The following encoding sequences were synthesized, and sequentially cloned into pGEM-T Easy vector (Promega, Lot No. A1360): B2m signal peptide (SEQ ID NO: 21), anti-NKG2A-scFv (containing SEQ ID NOS: 5 and 7), IgG4 hinge region (SEQ ID NO: 29), CD28 transmembrane region (SEQ ID NO: 11), CD28 co-stimulatory domain (SEQ ID NO: 13), to obtain A28 plasmid, and correct insertion of the target sequence into the plasmid was confirmed by sequencing.

After 3 ml of Opti-MEM (Gibco, Lot No. 31985-070) was added to a sterile tube to dilute the above plasmids, a packaging vector psPAX2 (Addgene, Lot No. 12260) and an envelope vector pMD2.G (Addgene, Lot No. 12259) were then added according to a ratio of plasmid:virus packaging vector:virus envelope vector=4:2:1. Then, 120 μl of X-treme GENE HP DNA transfection reagent (Roche, Lot No. 06366236001) was added, well mixed immediately, followed by incubation at room temperature for 15 min, and then the plasmid/vector/transfection reagent mixture was added dropwise into a culture flask of 293T cells. The viruses were collected at 24 and 48 hours and combined, and then subjected to ultracentrifugation (25000 g, 4° C., 2.5 hours) to obtain a concentrated lentivirus.

T cells were activated with DynaBeads CD3/CD28 CTS™ (Gibco, Lot No. 40203D), and cultured for 1 day at 37° C. and 5% $CO_2$. Then, the concentrated lentivirus was added, and after 3 days of continuous culture, T cells expressing NK inhibitory molecule were obtained.

TCR/CD3 component (specifically TRAC gene) and MHC-related genes (specifically B2M and RFX5) in the T cells expressing the NK inhibitory molecule were then knocked out using the CRISPR system. Specifically, 10 μg of Cas9 protein and 10 μg of sgRNA (3.3 μg TRAC sgRNA (SEQ ID NO: 43)+3.3 μg of B2m sgRNA (SEQ ID NO: 44)+3.3 μg of RFX5 sgRNA (SEQ ID NO: 45)) were electrically transfected into activated NKi-T cells at 400 V, 0.7 ms using a BTX Agile Pulse Max electroporator (Harvard Apparatus BTX). Immediately after electrotransfection, the NKi-T cells were placed in 1 ml of pre-heated medium, and cultured in the presence of IL-2 (300 IU/ml) at 37° C. and 5% $CO_2$ to obtain TCR/B2M/RFX5 triple knockout UNKi-T cells. The wild-type T cell with TCR/B2M/RFX5 being knocked out by the CRISPR system (i.e., Mock T cell) and the wild-type T cell without gene knockout (i.e., NT cell) were used as control.

The structure of the NK inhibitory molecule contained in the UNKi-T cells prepared in the present example is as shown in Table 1 below.

TABLE 1

UNKi-T cell comprising NK inhibitory molecule

| Cell Name | signal peptide | NK inhibitory ligand | hinge region | transmembrane domain | co-stimulatory domain |
|---|---|---|---|---|---|
| Ecad0-UNKi-T | B2M | E-cadherin extracellular region | CD28 | CD28 | none |
| Ecad28-UNKi-T | B2M | E-cadherin extracellular region | CD28 | CD28 | CD28 |
| E0-UNKi-T | B2M | presenting peptide + synonymously mutated B2M+ HLA-E extracellular region mutant | none | CD28 | none |
| E28-UNKi-T | B2M | presenting peptide + synonymously mutated B2M+ HLA-E extracellular region mutant | none | CD28 | CD28 |
| G0-UNKi-T | B2M | synonymously mutated B2M+ HLA-G extracellular region | none | CD28 | none |
| G28-UNKi-T | B2M | synonymously mutated B2M+ HLA-G extracellular region | none | CD28 | CD28 |
| A28-UNKi-T | B2M | anti-NKG2A-scFv | IgG4 | CD28 | CD28 |

After 11 days, expression efficiencies of TCR/HLA-I/HLA-II in UNKi-T cell, Mock T cell, and NT cell were measured by a flow cytometer using FITC Mouse Anti-Human CD3 (BD Pharmingen, Lot No. 555916) antibody, PE mouse anti-human HLA-I (R&D, Lot No. FAB7098P) and APC anti-human DR, DP, DQ (biolegend, Lot No. 361714) antibody, and results are shown in Table 2 below.

TABLE 2

Gene expression efficiency in UNKi-T cell

| Cell Name | TCR/CD3 | B2M/HLA-I | RFX5/HLA-II |
|---|---|---|---|
| Ecad0-UNKi-T | 3.6% | 19% | 11% |
| Ecad28-UNKi-T | 2.9% | 18.3% | 10.4% |
| E0-UNKi-T | 4.8% | 18.9% | 11.3% |
| E28-UNKi-T | 3.4% | 20% | 12% |
| G0-UNKi-T | 4% | 19% | 9.8% |
| G28-UNKi-T | 2.9% | 19.7% | 10% |
| A28-UNKi-T | 3.8% | 21.1% | 12.1% |
| Mock T | 2.7% | 17.8% | 9.8% |
| NT | 97% | 98% | 60% |

As can be seen from Table 2, expression of TCR/B2M/RFX5 in UNKi-T cell prepared in the present disclosure and Mock T cell is effectively suppressed or silenced.

Figure 2:
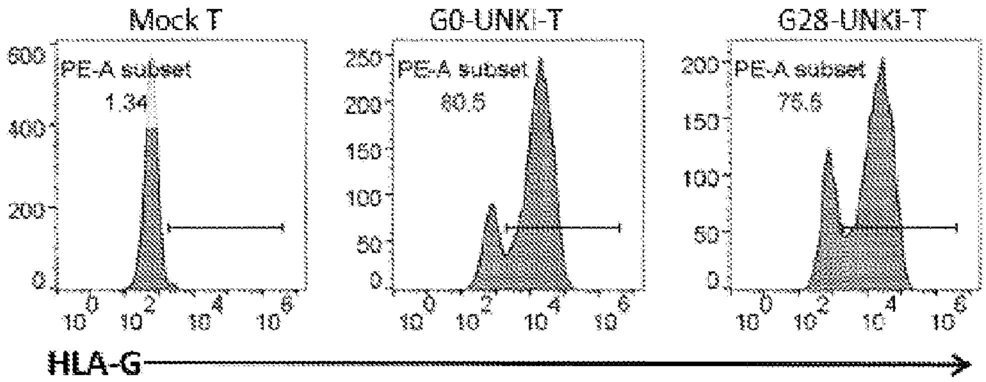
FIG. 2: Expression levels of HLA-G in G0-UNKi-T and G28-UNKi-T cells are shown.
Figure 3:
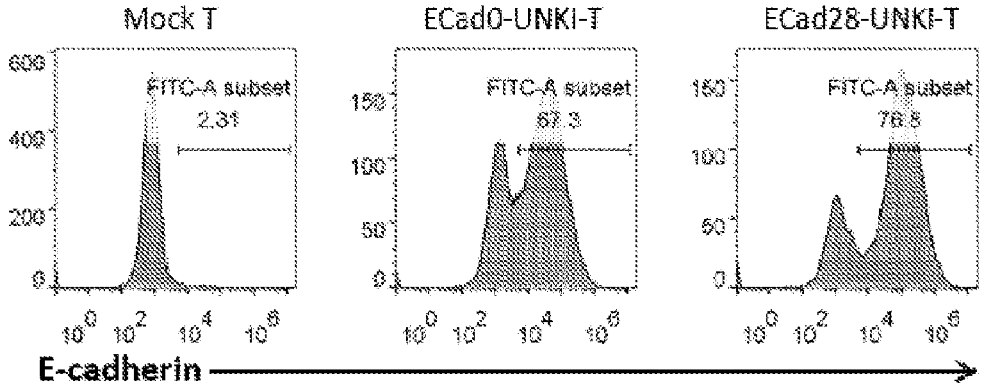
FIG. 3: Expression levels of E-cadherin in ECad0-UNKi-T and ECad28-UNKi-T cells are shown.
Figure 4:
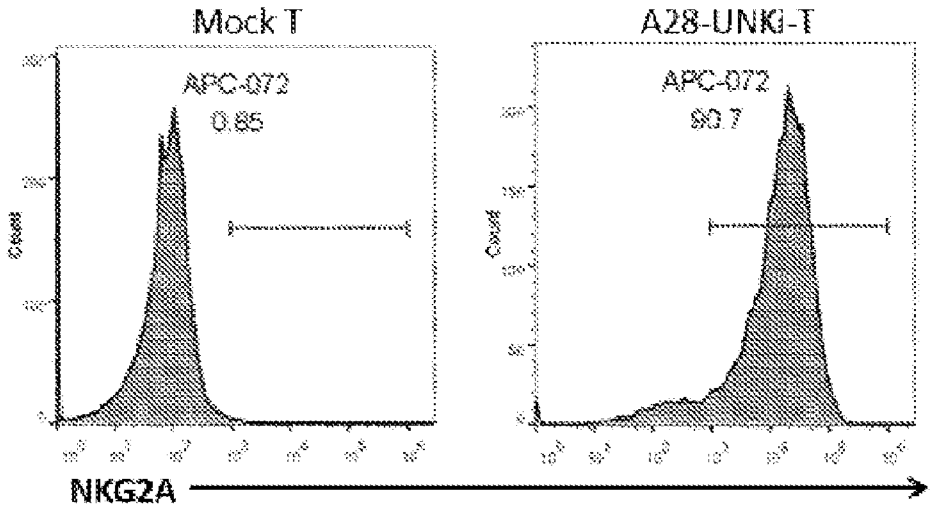
FIG. 4: Expression level of NKG2A scFv in A28-UNKi-T cells is shown.

Furthermore, HLA-E expression in UNKi-T cell and Mock T cell was detected by a flow cytometer using PE mouse anti-human HLA-E (biolegend, Lot No. 342604) (FIG. 1), HLA-G expression in UNKi-T cell and Mock T cell was detected using PE mouse anti-human HLA-G (biolegend, Lot No. 335906) (FIG. 2), E-cadherin expression in UNKi-T cell and Mock T cell was detected using E-cadherin monoclonal antibody (invitrogen, Lot No. 13-5700) and Goat anti-Mouse IgG (H+L) Cross-Adsorbed Secondary Antibody, Alexa Fluor 488 (Invitrogen, Lot No. A-11001) (FIG. 3), and anti-NKG2A scFv expression in UNKi-T cell and Mock T cell was detected using Biotin-SP (long spacer) AffiniPure Goat Anti-Human IgG, F(ab') fragment specific antibody (Jackson ImmunoResearch, Lot No. 109-065-097) and APC Streptavidin (BD, Lot No. 554067) (FIG. 4).

It can be seen from FIGS. 1-4 that the NK inhibitory molecules in the UNKi-T cell prepared in the present disclosure are all effectively expressed.

Example 2. Inhibitory Effect of UNKi-T Cell on NK Cell Killing Effect

The effector cells used in the present example are NK92 cells. Because the NK92 cell line does not express the receptor KLRG1 of E-cadherin, NK92 cell overexpressing KLRG1 was prepared first.

Figure 5:
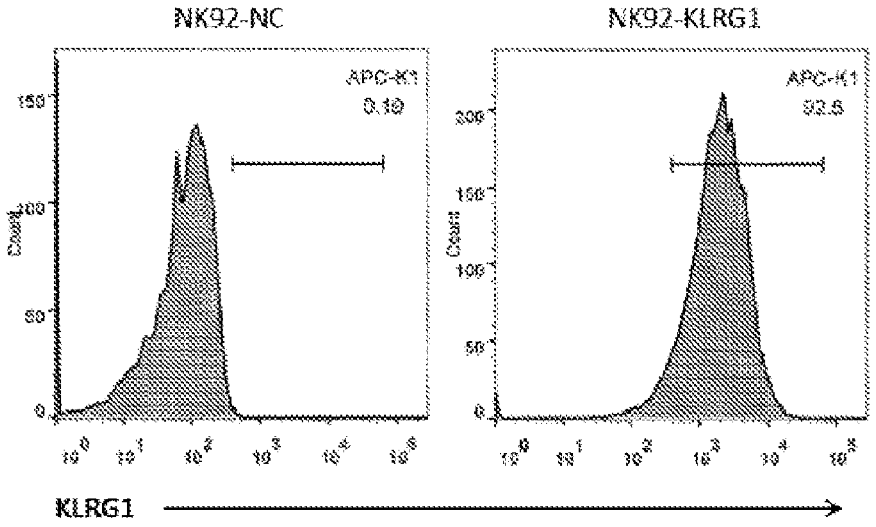
FIG. 5: Expression level of KLRG1 in NK92-KLRG1 cells is shown.

Nucleic acid sequences encoding KLRG1 (SEQ ID NO: 54) were synthesized, and sequentially cloned into pGEM-T Easy vector (Promega, Lot No. A1360), and the correct insertion of the target sequence was confirmed by sequencing. The vector was subjected to enzyme digestion with SpeI enzyme, purified, and recovered to obtain a linearized vector. Then mRNA was prepared using mMESSAGE mMACHINE@T7 Ultra Kit (Invitrogen, Lot No. AM1345) with a linearized vector as a template according to the manufacturer's recommendations, and purified with Fastpure cell/Tissue total RNA isolation kit (Vazyme, Lot No. RC101-01) to obtain purified mRNA. Then 20 μg of purified mRNA prepared above was electrically transfected into NK92 cells at 200 V and 2 ms using a BTX Agile Pulse Max electroporator (Harvard Apparatus BTX) to obtain NK92-KLRG1 cells. 16 h later, the expression of KLRG1 was detected, and result is as shown in FIG. 5. NK92 cells not transfected with KLRG1 served as control.

As can be seen from FIG. 5, NK92-KLRG1 cells can effectively express KLRG1.

The inhibitory effect of UNKi-T cells prepared in the present disclosure on NK cell killing effect was then detected according to the following method: UNKi-T cells prepared in the present disclosure and Mock-T cells were labeled with Far-Red (invitrogen, Lot No. C34564). Labeled UNKi-T cells and Mock T cells were then plated into a 96-well plate at a concentration of $1\times10^4$ cells per well, and were co-cultured with NK92 cells (for Mock T cells and UNKi-T cells expressing HLA-E, HLA-G or NKG2A scFv) or NK92-KLRG1 cells (for UNKi-T cells expressing E-cadherin) at an effector-target ratio of 2:1. After 16-18 hours, the ratio of T cells in the culture was detected by a flow cytometer, and the killing rate of the NK cells to the T cells was further calculated, and the results are shown in FIG. 6.

Figure 6:
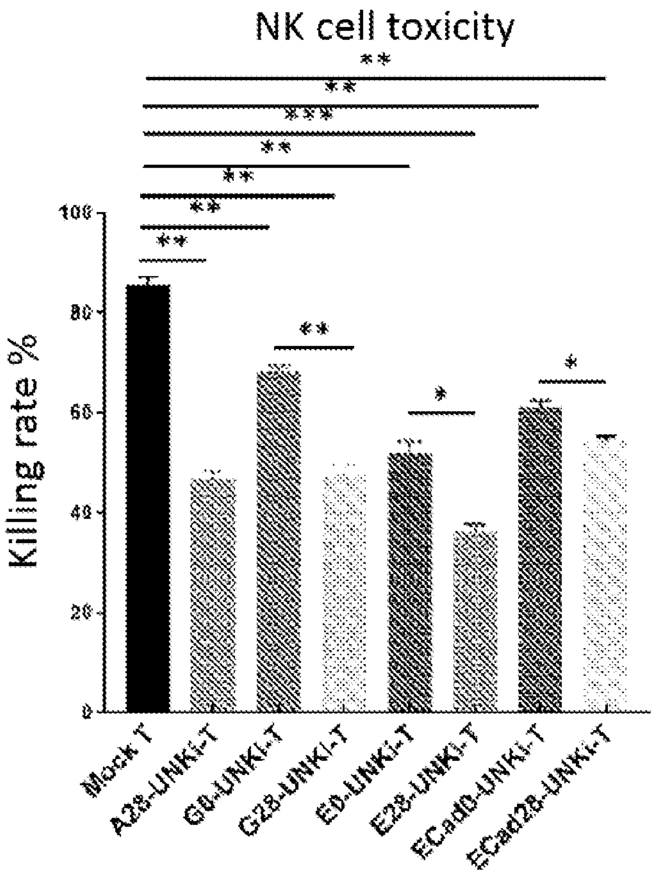
FIG. 6: Inhibitory effect of UNKi-T cells of the present disclosure on NK cell killing effect is shown. Two-way ANOVA is used for analysis, and T test is used for statistical analysis. * indicates that P value is less than 0.05,  indicates that P value is less than 0.01, * indicates that P value is less than 0.001, reaching significant levels.

It can be seen from FIG. 6 that compared with Mock T cells not expressing NK inhibitory molecules, UNKi-T cells expressing NK inhibitory molecules containing inhibitory ligands such as NKG2A scFv, HLA-G, HLA-E, and E-cadherin can significantly reduce the killing effect of NK cells on T cells. Moreover, compared with T cells only expressing inhibitory ligands and transmembrane domain, the addition of co-stimulatory domain may further significantly enhance inhibition of NK cell killing against T cells (see G0 vs G28; E0 vs E28; ECad0 vs ECad28). Therefore, the NK inhibitory molecule comprising an inhibitory ligand, a transmembrane domain, and a co-stimulatory domain prepared in the present disclosure can significantly reduce the killing effect of NK cells on UNKi-T cells, thereby being capable of effectively reducing the risk of HvGD.

Example 3. Killing Effect of UNKi-T Cell on NK Cell

E28z-UNKi-T and A28z-UNKi-T cells were prepared according to the method in Example 1, which differ from E28-UNKi-T and A28-UNKi-T cells only in that they further comprise a CD3 ζ intracellular signaling domain (SEQ ID NO: 17).

(1) Detecting Expression of NK Inhibitory Molecule

Figure 7:
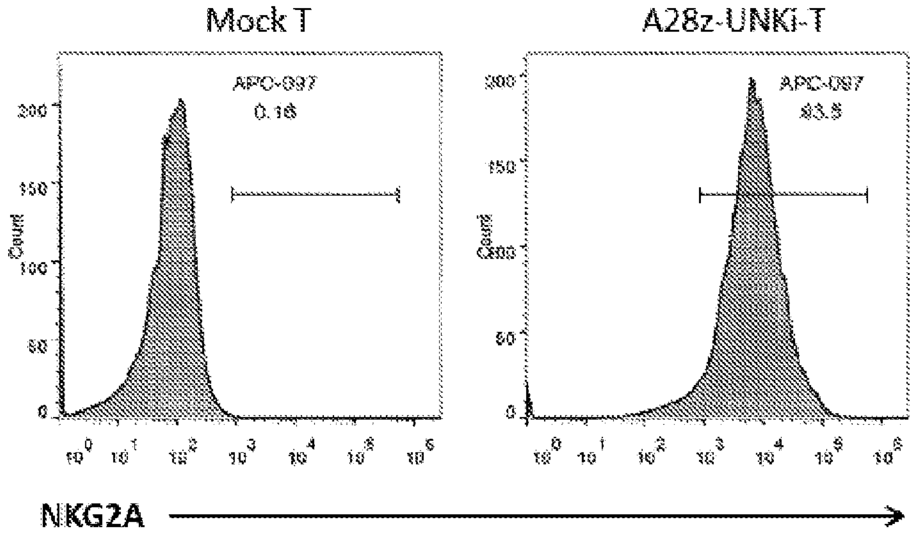
FIG. 7: Expression level of NKG2A scFv in A28z-UNKi-T cells is shown.
Figure 8:
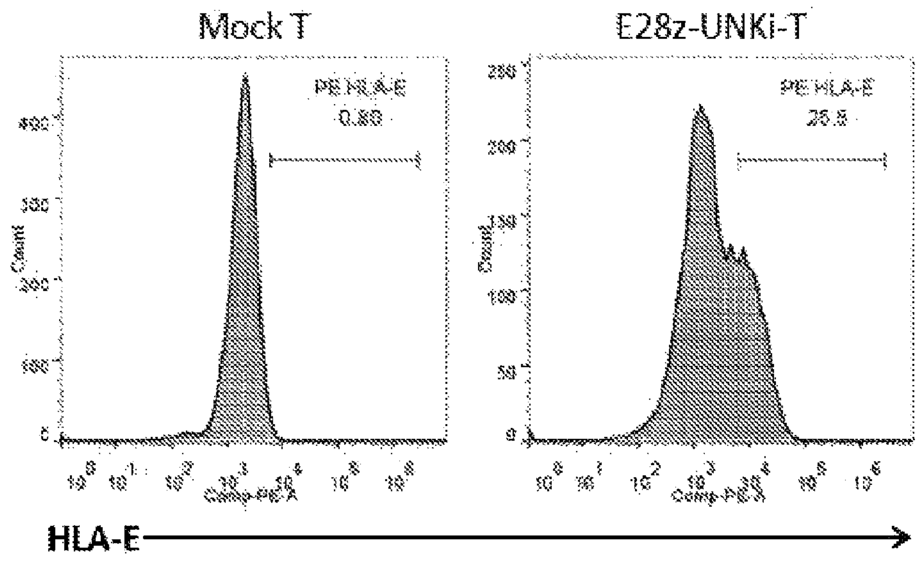
FIG. 8: Expression level of HLA-E in E28z-UNKi-T cells is shown.

The anti-NKG2A scFv expression in A28z-UNKi-T cells and Mock T cells was detected with Biotin-SP (long spacer) AffiniPure Goat Anti-Human IgG, F(ab') fragment specific antibody (Jackson ImmunoResearch, Lot No. 109-065-097) and APC Streptavidin (BD, Lot No. 554067) (FIG. 7). The HLA-E expression in E28z-UNKi-T cells and Mock T cells was detected with PE mouse anti-human HLA-E (biolegend Lot No. 342604) by a flow cytometer (FIG. 8).

It can be seen that the NK inhibitory molecules in the E28z-UNKi-T cells and A28z-UNKi-T cells prepared in the present disclosure can be effectively expressed.

(2) Detecting Expression of CD107a

The cytotoxic T lymphocyte (CTL cell) cytoplasm contains a high concentration of cytotoxic particles in the form of vesicles, and a lysosome associated membrane protein I (CD107a) is a main component of the vesicle membrane protein. When the CTL cell kills the target cell, toxic particles will reach the cell membrane and fuse with it (at this time, the CD107a molecule is transported to the surface of the cell membrane), causing release of particle content, and finally death of the target cell. Therefore, CD107a molecule is a sensitive marker for degranulation of CTL cells, and can reflect the cell killing activity.

Figure 9:
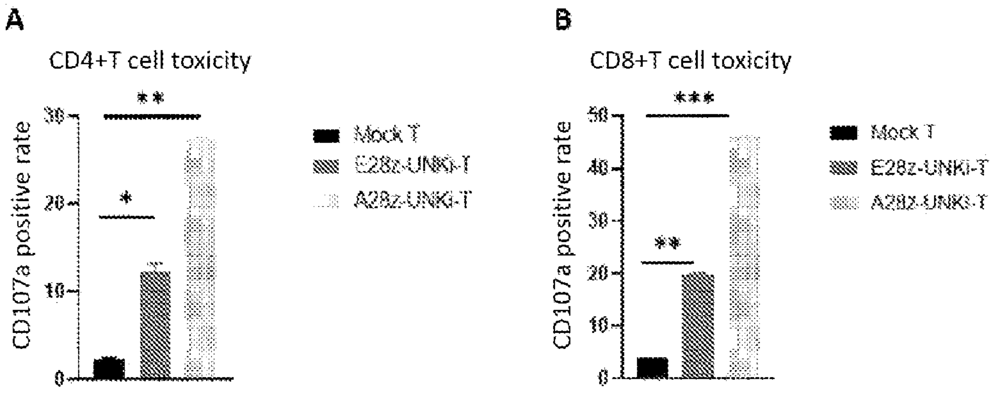
FIG. 9: Killing effect of UNKi-T cells of the present disclosure on NK cells is shown. Two-way ANOVA is used for analysis, and T test is used for statistical analysis. * indicates that P value is less than 0.05,  indicates that P value is less than 0.01, * indicates that P value is less than 0.001, reaching significant levels.

Target cells (NK92 cells) were plated in a 96-well plate at a concentration of $1\times10^5$ cells/well, then Mock T cells, E28z-UNKi-T cells, and A28z-UNKi-T cells were added at a ratio of 1:1 per well, meanwhile 10 μl of PE-anti-human CD107a (BD Pharmingen, Lot No. 555801) was added for co-culture at 37° C. and 5% $CO_2$ culture condition. After 1 h, Goigstop (BD Pharmingen, Lot No. 51-2092KZ) was added for further incubation of 2.5 h. 5 μl of APC-anti human CD8 (BD Pharmingen, Lot No.: 555369) and 5 μl of FITC-antihuman CD4 (BD Pharmingen, Lot No.: 561005) were then added to each well, after 30 minutes of incubation at 37° C., the expression level of CD107a was detected by a flow cytometer, and results are as shown in FIG. 9A (CD4+ T cell toxicity) and FIG. 9B (CD8+ T cell toxicity).

It can be seen that Mock T cells not expressing NK inhibitory molecules seldom kill target cells. On the contrary, after E28z-UNKi-T cells and A28z-UNKi-T cells prepared in the present disclosure were co-cultured with target cells, the expression rate of CD107a was significantly improved, indicating that the UNKi-T cells of the present disclosure can significantly kill the NK cells.

(3) Detecting IFN-γ Secretion

Target cells (NK92 cells) were plated in a 96-well plate at $1\times10^5$ cells/well, Mock T cells, E28z-UNKi-T cells, and A28z-UNKi-T cells were added at a ratio of 1:1 per well, and co-cultured at 37° C. and 5% $CO_2$ culture condition. After 18-24 hours, cell co-culture supernatant was collected.

Figure 10:
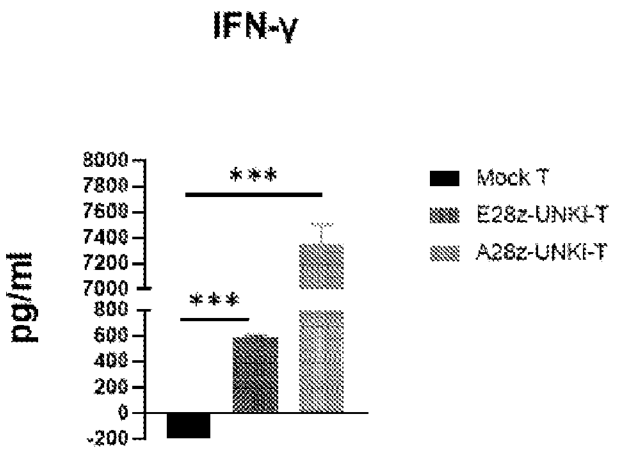
FIG. 10: IFN-γ release levels after co-culture of UNKi-T cells of the present disclosure with NK cells are shown. Two-way ANOVA is used for analysis, and T test is used for statistical analysis. *** indicates that P value is less than 0.001, reaching significant levels.

The 96-well plate was coated with capture antibody Purified anti-human IFN-γ Antibody (Biolegend, Lot No. 506502) and incubated overnight at 4° C., then the antibody solution was removed. 250 μL of PBST (1×PBS containing 0.1% Tween) solution containing 2% BSA (sigma, Lot No. V90093-1 kg) was added, and incubated at 37° C. for 2 hours. The plate was then washed 3 times with 250 μL of PBST (1×PBS containing 0.1% Tween). 50 μL of cell co-culture supernatant or a standard was added to each well, followed by incubation at 37° C. for 1 hour, then the plate was washed 3 times with 250 μL of PBST (1×PBS containing 0.1% Tween). Then 50 μL of detection antibody Anti-Interferon gamma antibody [MD-1] (Biotin) (abcam, Lot No. ab25017) was added to each well, and after 1 hour of incubation at 37° C., the plate was washed 3 times with 250 μL of PBST (1×PBS containing 0.1% Tween). HRP Streptavidin (Biolegend, Lot No. 405210) was then added, and after 30 minutes of incubation at 37° C., the supernatant was discarded, 250 μL of PBST (1×PBS containing 0.1% Tween) was added, and the plate was washed 5 times. 50 μL of TMB substrate solution was added to each well. The reaction was carried out in the dark at room temperature for 30 minutes, after which 50 μL of 1 mol/L $H_2SO_4$ was added to each well to stop the reaction. Within 30 minutes after the stop of the reaction, the absorbance at 450 nm was detected by a plate reader, and the content of cytokines was calculated according to a standard curve (drawn according to read value and concentration of the standard), and the result is as shown in FIG. 10.

It can be seen that cytokine IFN-γ release levels of E28z-UNKi-T cell and A28z-UNKi-T cell of the present disclosure are much higher than that of Mock T cell, which also indicates that their killing against the NK92 target cell is significantly increased.

Example 4. UNKi-T Cell Targeting KIR or LIR1 and Inhibitory Effect Thereof on NK Cell Killing Effect The following encoding sequences were synthesized, and sequentially cloned into the pLVX vector (Public Protein/Plasmid Library (PPL), Lot No.: PPL00157-4a): B2m signal peptide (SEQ ID NO: 21), anti-KIR-scFv (containing SEQ ID NOS: 55 and 56) or anti-LIR1 scFv (containing SEQ ID NOS: 57 and 58, or containing SEQ ID NOS: 59 and 60), IgG4 hinge region (SEQ ID NO: 29), CD8 α transmembrane region (SEQ ID NO: 9), CD28 co-stimulatory domain (SEQ ID NO: 13), to obtain KIRG4, LIRG4-1, and LIRG4-2 plasmids, and the correct insertion of the target sequence into the plasmids was confirmed by sequencing.

UNKi-T cells were prepared according to knockout and infection method in Example 1, and expression efficiencies of CD3/HLA-I/HLA-II in UNKi-T cell, Mock T cell, and NT cell were measured by a flow cytometer using FITC Mouse Anti-Human CD3 (BD Pharmingen, Lot No. 555916) antibody, PE mouse anti-human HLA-I (R&D, Lot No. FAB7098P) and APC anti-human DR, DP, DQ (biolegend, Lot No. 361714) antibody, and results are shown in Table 3 below.

TABLE 3

| Gene expression efficiency in UNKi-T cell | | | |
|---|---|---|---|
| Cell Name | TCR/CD3 | B2M/HLA-I | RFX5/HLA-II |
| KIRG4-UNKi-T | 4.5% | 16% | 10.8% |
| LIRG4-UNKi-1-T | 3.5% | 17.6% | 10.9% |
| LIRG4-UNKi-2-T | 4.3% | 16.9% | 10.3% |
| Mock T | 2.6% | 15.8% | 9.3% |
| NT | 98% | 98% | 83% |

As can be seen from Table 3, expression of CD3/HLA-I/HLA-II in UNKi-T cell prepared in the present disclosure and Mock T cell is effectively suppressed or silenced.

Figure 11:
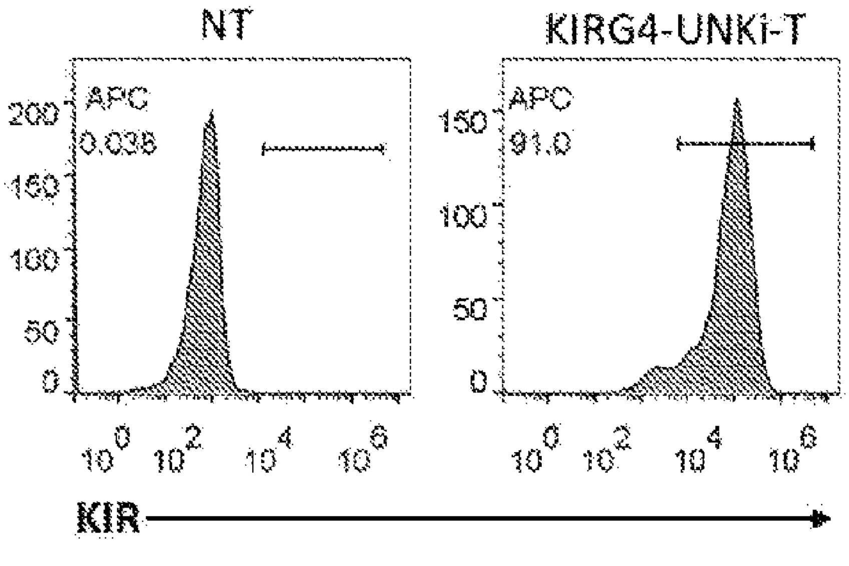
FIG. 11: Expression level of KIR scFv in KIRG4-UNKi-T cells of the present disclosure is shown.
Figure 12:
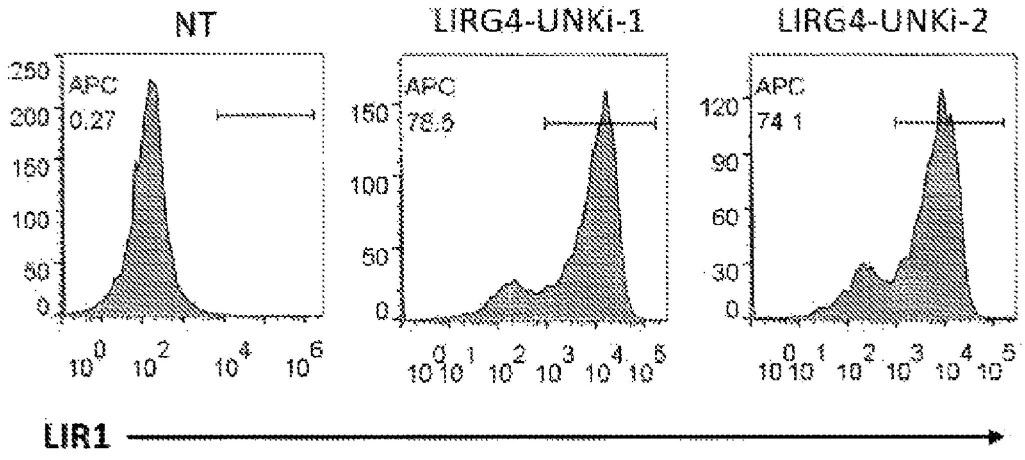
FIG. 12: Expression levels of LIR1 scFv in LIRG4-UNKi-1-T and LIRG4-UNKi-2-T cells of the present disclosure are shown.

The scFv expression in KIRG4-UNKi-T cell was detected with Biotin-SP (long spacer) AffiniPure Goat Anti-Human IgG, F(ab') fragment specific antibody (Jackson ImmunoResearch, Lot No. 109-065-097) and APC Streptavidin (BD, Lot No. 554067), the results are as shown in FIG. 11. The scFv expression in LIRG4-UNKi-1 T cell and LIRG4-UNKi-2 T cell was detected with recombinant human LILRB1 protein (sino biological, Lot No. 16014-H02H) as primary antibody, APC anti-human IgG Fc (biolegend, Lot No. 409306) as secondary antibody, the results are as shown in FIG. 12. It can be seen from FIG. 11 and FIG. 12 that the scFvs of the UNKi-T cell prepared in the present disclosure are all effectively expressed.

Figure 13:
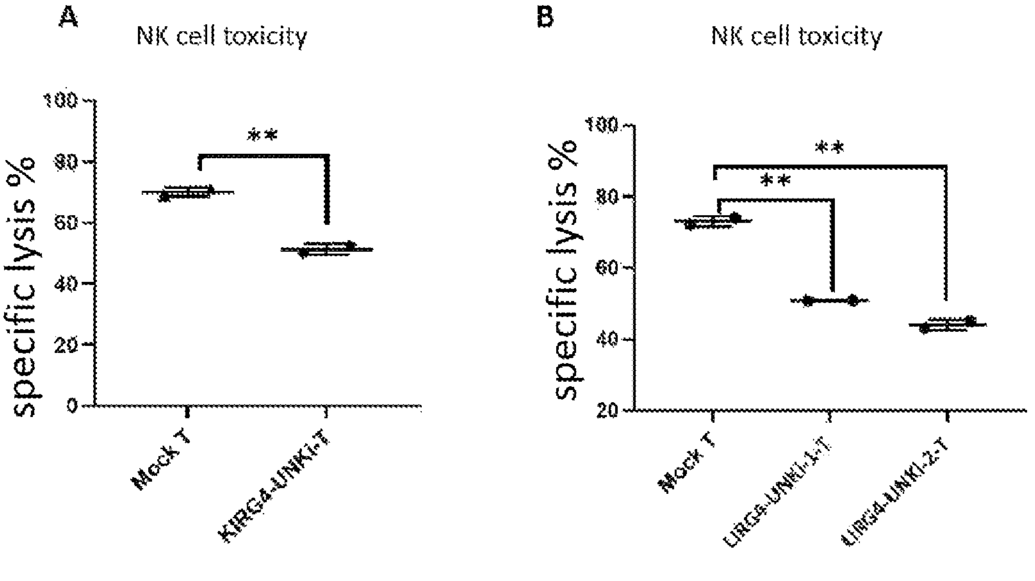
FIG. 13: Inhibitory effect of UNKi-T cells of the present disclosure on NK cell killing effect is shown.

UNKi-T cell and NK92 cell were co-cultured according to the method of Example 2 to detect the inhibitory effect of UNKi-T cell on NK cell killing effect, and the results are as shown in FIG. 13. It can be seen that compared with Mock T, all the UNKi-T cells targeting KIR (FIG. 13A) or LIR1 (FIG. 13B) prepared in the present example can significantly reduce the killing effect of NK cells on T cells.

Example 5. T Cell Targeting SIGLEC7, SIGLEC9 or KLRG1 and Inhibitory Effect Thereof on NK Cell Killing Effect The following encoding sequences were synthesized, and sequentially cloned into the pLVX vector (Public Protein/Plasmid Library (PPL), Lot No.: PPL00157-4a): B2m signal peptide (SEQ ID NO: 21), anti-SIGLEC7-scFv (SEQ ID NO: 130), anti-SIGLEC7/SIGLEC9-scFv (SEQ ID NO: 184), or anti-KLRG1-scFv (SEQ ID NO: 119), IgG4 hinge region (SEQ ID NO: 29), CD8 α transmembrane region (SEQ ID NO: 9), CD28 co-stimulatory domain (SEQ ID NO: 13), to obtain SC7G4, SC7/SC9G4, and K1G4 plasmids, and the correct insertion of the target sequence into the plasmids was confirmed by sequencing.

The above plasmids were transferred into T cells according to the method in Example 1, and the B2M gene therein was knocked out to obtain NKi-T cells (namely, SC7G4-T cells, SC7/SC9G4-T cells, and K1G4-T cells) expressing NK inhibitory molecules and with B2M being knocked out. T cells with only B2M being knocked out served as negative control (NT).

Figure 14:
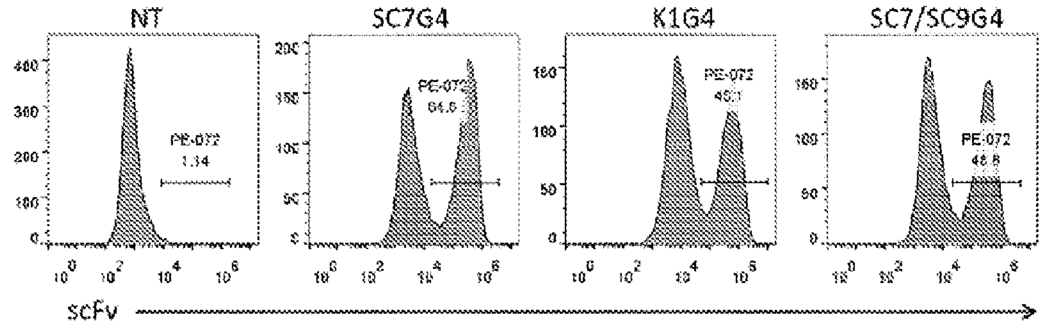
FIG. 14: Expression levels of scFv in SC7G4-T cells, SC7/SC9G4-T cells, and K1G4-T cells are shown.

The scFv expression in SC7G4, SC7/SC9G4, and K1G4T cell was detected with Biotin-SP (long spacer) AffiniPure Goat Anti-mouse IgG, F(ab') fragment specific antibody (Jackson ImmunoResearch, Lot No. 115-066-072) and APC Streptavidin (BD, Lot No. 554067), the results are as shown in FIG. 14. It can be seen that the scFvs of the NKi-T cells prepared in the present disclosure are all effectively expressed.

Figure 15:
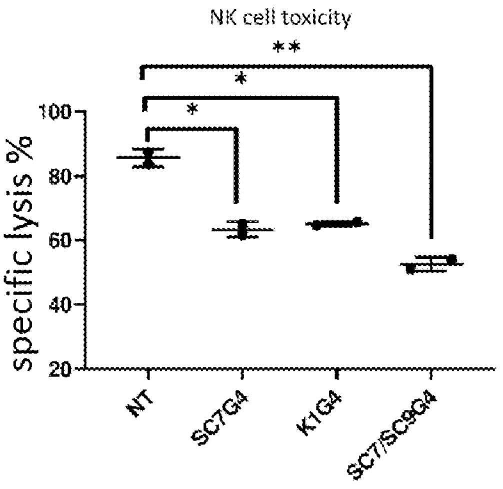
FIG. 15: Inhibitory effect of SC7G4-T cells, SC7/SC9G4-T cells, and K1G4-T cells on NK cell killing effect is shown.

According to the method of Example 2, the above NKi-T cell was co-cultured with NK92-KLRG1 cell to detect its inhibitory effect on the killing effect of NK cell, and results are as shown in FIG. 15. It can be seen that compared with NT, all the T cells targeting SIGLEC7, SIGLEC9 or KLRG1 prepared in the present example can significantly reduce the killing effect of NK cell on T cell.

Example 6 T Cell Targeting PD-1 and Inhibitory Effect Thereof on NK Cell Proliferation The following encoding sequences were synthesized, and sequentially cloned into the pLVX vector (Public Protein/Plasmid Library (PPL), Lot No.: PPL00157-4a): B2m signal peptide (SEQ ID NO: 21), anti-KIR-scFv (containing SEQ ID NOS: 55 and 56) or anti-LIRI scFv (containing SEQ ID NOS: 61 and 62, or containing SEQ ID NOS: 64 and 65), IgG4 hinge region (SEQ ID NO: 29), CD8 α transmembrane region (SEQ ID NO: 9), CD28 co-stimulatory domain (SEQ ID NO: 13), to obtain KIRG4, LIRG4-1, and LIRG4-2 plasmids, and the correct insertion of the target sequence into the plasmids was confirmed by sequencing.

Figure 16:
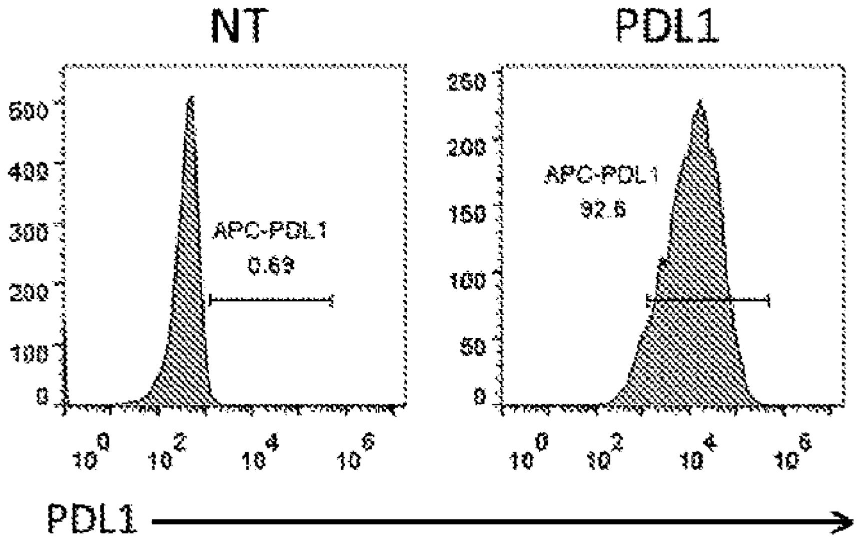
FIG. 16: Expression level of PDL1 in PDL1-T cells is shown.

The above plasmid was transferred into T cell according to the method in Example 1 to obtain NKi-T cell expressing NK inhibitory molecule, namely, PDL1-T cell. Expression thereof was detected with Anti-PD-L1 Antibody (manufacturer: Solarbio, Lot No.: 10084-R312-A), and results are as shown in FIG. 16. It can be seen that PDL1 is effectively expressed. Untreated T cell served as negative control (NT).

Figure 17:
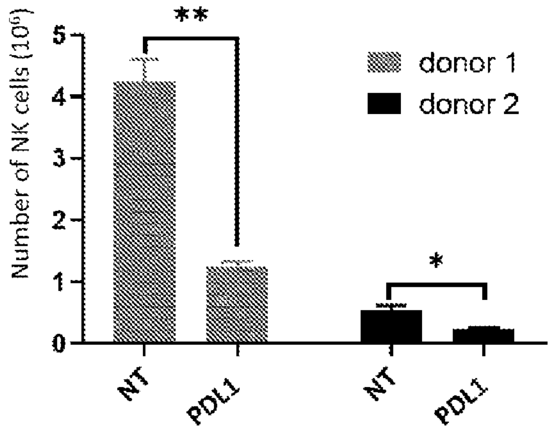
FIG. 17: Inhibitory effect of PDL1-T cells on NK cell proliferation is shown.

The above NKi-T cell was cultured and treated with cell mitomycin C. Two kinds of PBMCs from foreign sources (donor 1 and donor 2) were labeled with Far-Red, and then were co-cultured with T cell at a ratio of T cell:PBMC=1:2. Half-medium-replacement treatment was performed every 2-3 days. After 8 days, cells were counted and stained with PE anti-human CD3 (manufacturer biolegend, Lot No.: 317308) and FITC anti-human CD56 (manufacturer: biolegend, Lot No.: 362546), and then NK cell population ratio was detected by flow cytometry. The number of NK cells was calculated by the total cell amount*NK cell population ratio, and results are as shown in FIG. 17. It can be seen that NKi-T cell targeting PD-1 can significantly inhibit the proliferation of NK cell.

Example 7. Inhibitory Effect of B Cell and Huh7 Cell Targeting KIR on NK Cell Killing Effect The KIRG4 plasmid prepared in Example 4 was transducted into B cell and Huh7 cell (liver cancer cell) according to the method in Example 1, and the B2M gene therein was knocked out to obtain NKi-B cell and NKi-Huh7 cell expressing NK inhibitory molecule and with B2M being knocked out. B cell and Huh7 cell (NC cell), with only B2M gene being knocked out, served as negative control.

Figure 18:
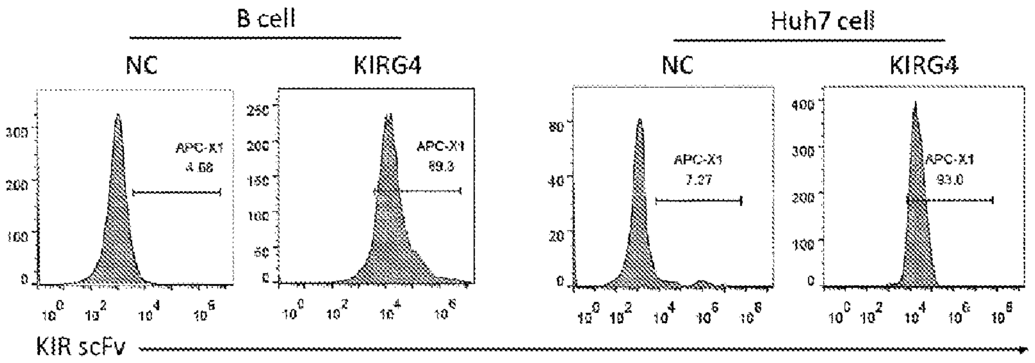
FIG. 18: Expression levels of KIR scFv in NKi-B cells and NKi-Huh7 cells are shown.

The scFv expression in NKi-B cell and NKi-Huh7 cell was detected with Biotin-SP (long spacer) AffiniPure Goat Anti-Human IgG, F(ab') fragment specific antibody (Jackson ImmunoResearch, Lot No. 109-065-097) and APC Streptavidin (BD, Lot No. 554067), and results are as shown in FIG. 18. It can be seen that the NK inhibitory molecules are effectively expressed in both B cell and Huh7 cell.

Figure 19:
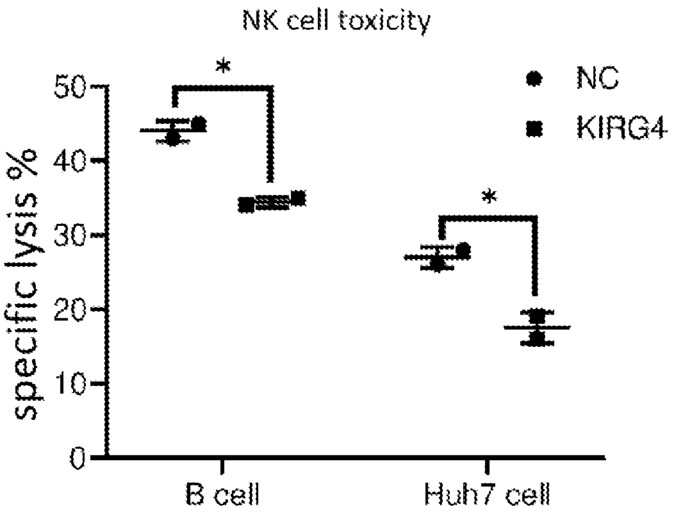
FIG. 19: Inhibitory effects of NKi-B cells and NKi-Huh7 cells on NK cell killing effect are shown.

The cells prepared in the above and NK cells were co-cultured according to the method of Example 2 to detect the inhibitory effect of the above cell on the killing effect of NK cell, and results are as shown in FIG. 19. It can be seen that compared with the NC cell, both NKi-B cell and NKi-Huh7 cell prepared in the present example can significantly reduce the killing effect of NK cell on them.

It should be noted that the above-mentioned are merely for preferred examples of the present disclosure and not used to limit the present disclosure. For one skilled in the art, various modifications and changes may be made to the present disclosure. Those skilled in the art should understand that any amendments, equivalent replacements, improvements, and so on, made within the spirit and principle of the present disclosure should be covered within the scope of protection of the present disclosure.

What is claimed is:

1. An NK inhibitory molecule comprising one or more NK inhibitory ligands, a transmembrane domain, and a co-stimulatory domain, wherein the one or more NK inhibitory ligands specifically bind to NK inhibitory receptors (NKIR) to inhibit killing of NK cells against an engineered immune cell expressing the NK inhibitory molecule, wherein the NK inhibitory molecule does not contain an intracellular signaling domain;

wherein the one or more NK inhibitory ligands are selected from the group consisting of:

(1) the extracellular region of E-cadherin comprising SEQ ID NO: 41;

(2) the extracellular region of HLA-E comprising SEQ ID NO: 33;

(3) the extracellular region of HLA-G comprising SEQ ID NO: 35:

(4) an anti-NKG2A antibody comprising: CDR-L1 comprising SEQ ID NO: 72, CDR-L2 comprising SEQ ID NO: 73, CDR-L3 comprising SEQ ID NO: 74, CDR-H1 comprising SEQ ID NO: 75, CDR-H2 comprising SEQ ID NO: 76, and CDR-H3 comprising SEQ ID NO: 77;

(5) an anti-KIR antibody comprising: CDR-L1 comprising SEQ ID NO: 84, CDR-L2 comprising SEQ ID NO: 85, CDR-L3 comprising SEQ ID NO: 86, CDR-HI comprising SEQ ID NO: 87, CDR-H2 comprising SEQ ID NO: 88, and CDR-H3 comprising SEQ ID NO: 89;

(6) an anti-SIGLEC7 antibody comprising: CDR-L1 comprising SEQ ID NO: 122, CDR-L2 comprising SEQ ID NO: 123, CDR-L3 comprising SEQ ID NO: 124, CDR-H1 comprising SEQ ID NO: 125, CDR-H2 comprising SEQ ID NO: 126 and CDR-H3 comprising SEQ ID NO: 127;

(7) an anti-SIGLEC7/9 antibody comprising: CDR-L1 comprising SEQ ID NO: 176, CDR-L2 comprising SEQ ID NO: 177, CDR-L3 comprising SEQ ID NO: 178, CDR-H1 comprising SEQ ID NO: 179, CDR-H2 comprising SEQ ID NO: 180 and CDR-H3 comprising SEQ ID NO: 181;

(8) an anti-KLRG1 antibody comprising: CDR-L1 comprising SEQ ID NO: 111, CDR-L2 comprising SEQ ID NO: 112, CDR-L3 comprising SEQ ID NO: 113, CDR-H1 comprising SEQ ID NO: 114, CDR-H2 comprising SEQ ID NO: 115, and CDR-H3 comprising SEQ ID NO: 116; and (9) the extracellular region of PDL1 comprising SEQ ID NO: 70.

2. The NK inhibitory molecule according to claim 1, wherein the transmembrane domain is a transmembrane domain of a protein selected from the group consisting of: TCR α chain, TCR β chain, TCR γ chain, TCR δ chain, CD3δ subunit, CD3 ε subunit, CD3 γ subunit, CD3 δ subunit, CD45, CD4, CD5, CD8 α, CD9, CD16, CD22, CD33, CD28, CD37, CD64, CD80, CD86, CD134, CD137, CD154, HLA-E, HLA-F, HLA-G, cadherin, collagen, and OCIL.

3. The NK inhibitory molecule according to claim 1, wherein the co-stimulatory domain is a co-stimulatory signaling domain of a protein selected from the group consisting of LTB, CD94, TLR1, TLR2, TLR3, TLR4, TLR5, TLR6, TLR7, TLR8, TLR9, TLR10, CARD11, CD2, CD7, CD8, CD18, CD27, CD28, CD30, CD40, CD54, CD83, CD134 (OX40), CD137 (4-1BB), CD270 (HVEM), CD272 (BTLA), CD276 (B7-H3), CD278 (ICOS), CD357 (GITR), DAP10, DAP12, LAT, NKG2C, SLP76, PD-1, LIGHT, TRIM, ZAP70, and a combination thereof.

4. The NK inhibitory molecule according to claim 1, wherein the intracellular signaling domain is a signaling domain of a protein selected from the group consisting of: FcR γ, FcR β, CD3 γ, CD3 δ, CD3 ε, CD3ζ, CD22, CD79a, CD79b, and CD66d.

5. An engineered immune cell, (1) expressing the NK inhibitory molecule according to claim 1, and (2) with the expression of at least one MHC-related gene being suppressed or silenced.

6. The engineered immune cell according to claim 5, wherein the engineered immune cell further expresses a chimeric antigen receptor, and the chimeric antigen receptor comprises a ligand binding domain, a transmembrane domain, a co-stimulatory domain, and an intracellular signaling domain.

7. The engineered immune cell according to claim 6, wherein the NK inhibitory molecule is in the form of a fusion protein with a chimeric antigen receptor, wherein the fusion protein comprises an NK inhibitory ligand, a ligand binding domain, a transmembrane domain, a co-stimulatory domain, and an intracellular signaling domain.

8. The engineered immune cell according to claim 5, wherein the at least one MHC-related gene is selected from the group consisting of HLA-A, HLA-B, HLA-C, B2M, HLA-DPA, HLA-DQ, HLA-DRA, TAP1, TAP2, LMP2, LMP7, RFX5, RFXAP, RFXANK, CIITA, and a combination thereof.

9. The engineered immune cell according to claim 8, wherein the at least one MHC-related gene is selected from the group consisting of B2M, RFX5, RFXAP, RFXANK, CIITA, and a combination thereof.

10. The engineered immune cell according to claim 9, wherein the MHC-related gene comprises B2M, wherein the NK inhibitory ligand is a fusion molecule of B2M and an extracellular region of non-classical HLA-class I molecule.

11. The engineered immune cell according to claim 10, wherein the non-classical HLA-class I molecule is HLA-E or HLA-G.

12. The engineered immune cell according to claim 5, wherein expression of at least one TCR/CD3 gene of the engineered immune cell is suppressed or silenced, and the TCR/CD3 gene is selected from the group consisting of TRAC, TRBC, CD3 γ, CD3 δ, CD3 ε, CD3 ζ, and a combination thereof.

13. The engineered immune cell according to claim 6, wherein the ligand binding domain binds to a target selected from the group consisting of: TSHR, CD2, CD3, CD4, CD5, CD7, CD8, CD14, CD15, CD19, CD20, CD21, CD23, CD24, CD25, CD37, CD38, CD40, CD40L, CD44, CD46, CD47, CD52, CD54, CD56, CD70, CD73, CD80, CD97, CD123, CD22, CD126, CD138, CD 179a, DR4, DR5, TAC, TEM1/CD248, VEGF, GUCY2C, EGP40, EGP-2, EGP-4, CD133, IFNAR1, DLL3, kappa light chain, TIM3, BAFF-R, CD30, CD171, CS-1, CLL-1, CD33, EGFRVIII, tEGFR, GD2, GD3, BCMA, GPRC5D, Tn antigen, PSMA, ROR1, FLT3, FAP, TAG72, CD38, CD44v6, CEA, EPCAM, B7H3, KIT, IL-13Ra2, IL-22Ra, IL-2, mesothelin, IL-11Ra, PSCA, PRSS21, VEGFR2, LewisY, CD24, PDGFR-β, SSEA-4, CD20, AFP, Folate receptor a, ERBB2 (Her2/neu), ErbB3, ErbB4, MUCI, MUC16, EGFR, CS1, CD138, NCAM, Claudin18.2, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor B, TEM1/CD248, TEM7R, CLDN6, GPRC5D, CXORF61, CD97, CD 179a, ALK, polysialic acid, PLAC1, GloboH, NY-BR-1, UPK2, HAVCRI, ADRB3, PANX3, GPR20, LY6K, OR51E2, TARP, WTI, NY-ESO-1, LAGE-1a, MAGE-A1, MAGE-A3, MAGE-A6, legumain, HPV E6, E7, MAGE-A4, MART-1, WT-1, ETV6-AML, sperm protein 17, XAGE1, Tie 2, MAD-CT-1, MAD-CT-2, Fos associated antigen 1, p53, p53 mutant, prostate specific protein, survivin and telomerase, PCTA-1/Galectin 8, MelanA/MART1, Ras mutant, hTERT, sarcoma translocation breakpoint, ML-IAP, ERG (TMPRSS2 ETS fusion gene), NA17, PAX3, androgen receptor, Cyclin B1, MYCN, RhoC, TRP-2, CYPIB 1, BORIS, SART3, PAX5, OY-TES 1, LCK, AKAP-4, SSX2, RAGE-1, human telomerase reverse transcriptase, RUI, RU2, intestinal tract carboxylesterase, mut hsp70-2, CD79a, CD79b, CD72, LAIR1, FCAR, LILRA2, CD300LF, CLEC12A, BST2, EMR2, LY75, GPC3, FCRL5, IGLL1, PD1, PDL1, PDL2, TGFB, APRIL, NKG2D, NKG2DL, and any combination thereof.

14. The engineered immune cell according to claim 5, wherein the engineered immune cell is a B cell, a T cell, a macrophage, a dendritic cell, a monocyte, an NK cell, or an NKT cell.

15. The engineered immune cell according to claim 14, wherein the engineered immune cell is a CD4+/CD8+ T cell, a CD4+ helper T cell, a CD8+ T cell, a tumor infiltrating cell, a memory T cell, a naive T cell, a γδ-T cell, or an αβ-T cell.

16. A pharmaceutical composition, which contains the NK inhibitory molecule according to claim 1 and one or more pharmaceutically acceptable excipients.

* * * * *